US007482325B2

(12) United States Patent
Yoshinaga et al.

(10) Patent No.: US 7,482,325 B2
(45) Date of Patent: Jan. 27, 2009

(54) DOWNREGULATION OF IMMUNE RESPONSE BY ADMINISTERING B7RP-2 FUSION PROTEIN

(75) Inventors: Steven Kiyoshi Yoshinaga, Thousand Oaks, CA (US); Woong-Kyung Suh, Toronto (CA); Tak Wah Mak, Toronto (CA)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/229,307

(22) Filed: Sep. 16, 2005

(65) Prior Publication Data

US 2006/0269565 A1 Nov. 30, 2006

Related U.S. Application Data

(63) Continuation of application No. 10/156,424, filed on May 28, 2002, now abandoned.

(60) Provisional application No. 60/293,629, filed on May 25, 2001.

(51) Int. Cl.
*A61K 38/16* (2006.01)
*A61K 39/395* (2006.01)
*C07K 14/705* (2006.01)
*C07K 16/46* (2006.01)

(52) U.S. Cl. ...................... 514/12; 424/134.1; 530/350; 530/387.3

(58) Field of Classification Search ....................... None
See application file for complete search history.

(56) References Cited

U.S. PATENT DOCUMENTS 6,630,575 B2 * 10/2003 Coyle et al. ................. 530/350
6,891,030 B2 * 5/2005 Chen ......................... 536/23.5
2002/0168762 A1 11/2002 Chen

FOREIGN PATENT DOCUMENTS

WO WO 99/46281 A2 9/1999
WO WO 99/63088 A2 12/1999
WO WO 9963088 A3 12/1999
WO WO 00/36107 A2 5/2000
WO WO 00/36107 A3 5/2000
WO WO 00/50405 A1 8/2000
WO WO 00/53758 A2 9/2000
WO WO 01/18021 A1 3/2001

OTHER PUBLICATIONS

Attwood T., Science 2000; 290:471-473.*
Skolnick et al., Trends in Biotech. 2000; 18(1):34-39.*
Blazar et al., J. Immunol., 1996, 157: 3250-3259.*
Attwood, T.K., “The Babel of Bioinformatics”, Science Magazine, vol. 290: p. 471-473 (2000).
Skolnick, et al., “From Genes to Protein Structure and Function: Novel Application of Computational Approaches in the Genomic Era”, Trends in Biotech, vol. 18(1): p. 34-39 (2000).
Metzler, et al., “Solution Structure of Human CTLA-4 and Delineation of a CD80/CD86 Binding Site Conserved in CD28”, Nature Structural Biology, vol. 4(7): p. 527-531 (1997).
Burgess, et al., “Possible Dissociation of the Heparin-binding and Mitogenic Activities of Heparin-binding and Mitogenic Activities of Heparin-binding (Acidic Fibroblast) Growth Factor-1 from Its Receptor-binding Activities by Site-directed Mutagenesis of a Single Lysine Residue”, vol. 111: p. 2129-2138, (1990.).
Lazar, et al., “Transforming Growth Factor α: Mutation of Aspartic Acid 47 and Leucine 48 Results in Different Biological Activities”, Mulecular and Cellular Biology, vol. 8(3): p. 1247-1252, (1998).
Bowie et al., “Deciphering the Message in Protein Sequences: Tolerance to Amino Acid Substitutions”, Science, vol. 247: p. 1306-1310, (1990).
Chapoval et al., “B7-H3: A Costumulatory Molecule for T Cell Activation and IFN-g production.”Nature Immunol. Mar. 2001, vol. 2, No. 3, pp. 269-274.
Database GenBank, Accession No. AF302102, Chapoval et al., Mar. 3, 2001.
Database GenBank Accession No. AAK15438, Chapoval et al., Mar. 3, 2001.

* cited by examiner

*Primary Examiner*—Ilia Ouspenski
(74) *Attorney, Agent, or Firm*—Patricia Anne Perkins

(57) ABSTRACT

The present invention provides B7 Related Protein-2 (B7RP-2) polypeptides and nucleic acid molecules encoding the same. The invention also provides selective binding agents, vectors, host cells, and methods for producing B7RP-2 polypeptides. The invention further provides pharmaceutical compositions and methods for the diagnosis, treatment, amelioration, and/or prevention of diseases, disorders, and conditions associated with B7RP-2 polypeptides.

8 Claims, 22 Drawing Sheets

FIG. 1A

```
ccgggtcgac ccacgcgtcc ggcggcggcg actgagccag gctgggccgc gtccctgagt 60

cccagagtcg gcgcggcgcg gcaggggcag ccttccacca cggggagccc agctgtcagc 120

cgcctcacag gaag atg ctg cgt cgg cgg ggc agc cct ggc atg ggt gtg   170
                Met Leu Arg Arg Arg Gly Ser Pro Gly Met Gly Val
                 1               5                   10

cat gtg ggt gca gcc ctg gga gca ctg tgg ttc tgc ctc aca gga gcc   218
His Val Gly Ala Ala Leu Gly Ala Leu Trp Phe Cys Leu Thr Gly Ala
        15                  20                  25

ctg gag gtc cag gtc cct gaa gac cca gtg gtg gca ctg gtg ggc acc   266
Leu Glu Val Gln Val Pro Glu Asp Pro Val Val Ala Leu Val Gly Thr
    30                  35                  40

gat gcc acc ctg tgc tgc tcc ttc tcc cct gag cct ggc ttc agc ctg   314
Asp Ala Thr Leu Cys Cys Ser Phe Ser Pro Glu Pro Gly Phe Ser Leu
 45                  50                  55                  60

gca cag ctc aac ctc atc tgg cag ctg aca gat acc aaa cag ctg gtg   362
Ala Gln Leu Asn Leu Ile Trp Gln Leu Thr Asp Thr Lys Gln Leu Val
                65                  70                  75

cac agc ttt gct gag ggc cag gac cag ggc agc gcc tat gcc aac cgc   410
His Ser Phe Ala Glu Gly Gln Asp Gln Gly Ser Ala Tyr Ala Asn Arg
            80                  85                  90

acg gcc ctc ttc ccg gac ctg ctg gca caa ggc aat gca tcc ctg agg   458
Thr Ala Leu Phe Pro Asp Leu Leu Ala Gln Gly Asn Ala Ser Leu Arg
        95                  100                 105

ctg cag cgc gtg cgt gtg gcg gac gag ggc agc ttc acc tgc ttc gtg   506
Leu Gln Arg Val Arg Val Ala Asp Glu Gly Ser Phe Thr Cys Phe Val
    110                 115                 120

agc atc cgg gat ttc ggc agc gct gcc gtc agc ctg cag gtg gcc gct   554
Ser Ile Arg Asp Phe Gly Ser Ala Ala Val Ser Leu Gln Val Ala Ala
125                 130                 135                 140

ccc tac tcg aag ccc agc atg acc ctg gag ccc aac aag gac ctg cgg   602
Pro Tyr Ser Lys Pro Ser Met Thr Leu Glu Pro Asn Lys Asp Leu Arg
                145                 150                 155

cca ggg gac acg gtg acc atc acg tgc tcc agc tac cgg ggc tac cct   650
Pro Gly Asp Thr Val Thr Ile Thr Cys Ser Ser Tyr Arg Gly Tyr Pro
            160                 165                 170

gag gct gag gtg ttc tgg cag gat ggg cag ggt gtg ccc ctg act ggc   698
Glu Ala Glu Val Phe Trp Gln Asp Gly Gln Gly Val Pro Leu Thr Gly
        175                 180                 185

aac gtg acc acg tcg cag atg gcc aac gag cag ggc ttg ttt gat gtg   746
Asn Val Thr Thr Ser Gln Met Ala Asn Glu Gln Gly Leu Phe Asp Val
    190                 195                 200
```

FIG. 1B

```
cac agc gtc ctg cgg gtg gtg ctg ggt gcg aat ggc acc tac agc tgc    794
His Ser Val Leu Arg Val Val Leu Gly Ala Asn Gly Thr Tyr Ser Cys
205                 210                 215                 220

ctg gtg cgc aac ccc gtg ctg cag cag gat gcg cac ggc tct gtc acc    842
Leu Val Arg Asn Pro Val Leu Gln Gln Asp Ala His Gly Ser Val Thr
                225                 230                 235

atc aca ggg cag cct atg aca ttc ccc cca gag gcc ctg tgg gtg acc    890
Ile Thr Gly Gln Pro Met Thr Phe Pro Pro Glu Ala Leu Trp Val Thr
            240                 245                 250

gtg ggg ctg tct gtc tgt ctc att gca ctg ctg gtg gcc ctg gct ttc    938
Val Gly Leu Ser Val Cys Leu Ile Ala Leu Leu Val Ala Leu Ala Phe
        255                 260                 265

gtg tgc tgg aga aag atc aaa cag agc tgt gag gag gag aat gca gga    986
Val Cys Trp Arg Lys Ile Lys Gln Ser Cys Glu Glu Glu Asn Ala Gly
    270                 275                 280

gct gag gac cag gat ggg gag gga gaa ggc tcc aag aca gcc ctg cag    1034
Ala Glu Asp Gln Asp Gly Glu Gly Glu Gly Ser Lys Thr Ala Leu Gln
285                 290                 295                 300

cct ctg aaa cac tct gac agc aaa gaa gat gat gga caa gaa ata gcc    1082
Pro Leu Lys His Ser Asp Ser Lys Glu Asp Asp Gly Gln Glu Ile Ala
                305                 310                 315

tgaccatgag gaccagggag ctgctacccc tccctacagc tcctaccctc tggctgcaat 1142

ggggctgcac tgtgagccct gcccccaaca gatgcatcct gctctgacag gtgggctcct 1202

tctccaaagg atgcgataca cagaccactg tgcagcctta tttctccaat ggacatgatt 1262

cccaagtcat cctgctgcct tttttcttat agacacaatg aacagaccac ccacaacctt 1322

agttctctaa gtcat                                                  1337
```

FIG. 2A

```
tggtaccgag ctcggatcca ctagtaacgg ccgccagtgt gctggaattc gcccttgctg 60

tctcacagga ag atg ctt cga gga tgg ggt ggc ccc agt gtg ggt gtg tgt 111
              Met Leu Arg Gly Trp Gly Gly Pro Ser Val Gly Val Cys
              1               5                   10

gtg cgc aca gca ctg ggg gtg ctg tgc ctc tgc ctc aca gga gct gtg   159
Val Arg Thr Ala Leu Gly Val Leu Cys Leu Cys Leu Thr Gly Ala Val
    15                  20                  25

gaa gtc cag gtc tct gaa gac ccc gtg gtg gcc ctg gtg gac acg gat   207
Glu Val Gln Val Ser Glu Asp Pro Val Val Ala Leu Val Asp Thr Asp
30                  35                  40                  45

gcc acc cta cgc tgc tcc ttt tcc cca gag cct ggc ttc agt ctg gca   255
Ala Thr Leu Arg Cys Ser Phe Ser Pro Glu Pro Gly Phe Ser Leu Ala
                50                  55                  60

cag ctc aac ctc atc tgg cag ctg aca gac acc aaa cag ctg gtg cac   303
Gln Leu Asn Leu Ile Trp Gln Leu Thr Asp Thr Lys Gln Leu Val His
            65                  70                  75

agc ttc acg gag ggc cgg gac caa ggc agt gcc tac tcc aac cgc aca   351
Ser Phe Thr Glu Gly Arg Asp Gln Gly Ser Ala Tyr Ser Asn Arg Thr
        80                  85                  90

gcg ctc ttc cct gac ctg ttg gtg caa ggc aat gcg tcc ttg agg ctg   399
Ala Leu Phe Pro Asp Leu Leu Val Gln Gly Asn Ala Ser Leu Arg Leu
    95                  100                 105

cag cgc gtc cga gta acc gac gag ggc agc tac acc tgc ttt gtg agc   447
Gln Arg Val Arg Val Thr Asp Glu Gly Ser Tyr Thr Cys Phe Val Ser
110                 115                 120                 125

atc cag gac ttt gac agc gct gct gtt agc ctg cag gtg gcc gcc ccc   495
Ile Gln Asp Phe Asp Ser Ala Ala Val Ser Leu Gln Val Ala Ala Pro
                130                 135                 140

tac tcg aag ccc agc atg acc ctg gag ccc aac aag gac cta cgt cca   543
Tyr Ser Lys Pro Ser Met Thr Leu Glu Pro Asn Lys Asp Leu Arg Pro
            145                 150                 155

ggg aac atg gtg acc atc acg tgc tct agc tac cag ggc tat ccg gag   591
Gly Asn Met Val Thr Ile Thr Cys Ser Ser Tyr Gln Gly Tyr Pro Glu
        160                 165                 170

gcc gag gtg ttc tgg aag gat gga cag gga gtg ccc ttg act ggc aat   639
Ala Glu Val Phe Trp Lys Asp Gly Gln Gly Val Pro Leu Thr Gly Asn
    175                 180                 185

gtg acc aca tcc cag atg gcc aac gag cgg ggc ttg ttc gat gtt cac   687
Val Thr Thr Ser Gln Met Ala Asn Glu Arg Gly Leu Phe Asp Val His
190                 195                 200                 205

agc gtg ctg agg gtg gtg ctg ggt gct aac ggc acc tac agc tgc ctg   735
Ser Val Leu Arg Val Val Leu Gly Ala Asn Gly Thr Tyr Ser Cys Leu
                210                 215                 220
```

FIG. 2B

```
gta cgc aac ccg gtg ttg cag caa gat gct cac ggc tca gtc acc atc    783
Val Arg Asn Pro Val Leu Gln Gln Asp Ala His Gly Ser Val Thr Ile
            225                     230                     235

aca ggg cag ccc ctg aca ttc ccc cct gag gct ctg tgg gta acc gtg    831
Thr Gly Gln Pro Leu Thr Phe Pro Pro Glu Ala Leu Trp Val Thr Val
        240                     245                     250

ggg ctc tct gtc tgt ctt gtg gta cta ctg gtg gcc ctg gct ttc gtg    879
Gly Leu Ser Val Cys Leu Val Val Leu Leu Val Ala Leu Ala Phe Val
    255                     260                     265

tgc tgg aga aag atc aag cag agc tgc gag gag gag aat gca ggt gcc    927
Cys Trp Arg Lys Ile Lys Gln Ser Cys Glu Glu Glu Asn Ala Gly Ala
270                     275                     280                     285

gag gac cag gat gga gat gga gaa gga tcc aag aca gct cta cgg cct    975
Glu Asp Gln Asp Gly Asp Gly Glu Gly Ser Lys Thr Ala Leu Arg Pro
                290                     295                     300

ctg aaa ccc tct gaa aac aaa gaa gat gac gga caa gaa att gct        1020
Leu Lys Pro Ser Glu Asn Lys Glu Asp Asp Gly Gln Glu Ile Ala
            305                     310                     315

tgattgggag ctgctgcaag ggcgaattct gcagatatcc atcacactgg cggccgctcg 1080

agcatgcatc tagag                                                   1095
```

FIG. 3A

```
cctcgcggct gctctaccga cggtggcggc gattgtgctg cgccccgccg cgtccccgag 60

tcccgggagt cggcgcggcg cggcaggagc agccatccgc cacggagagt ccagctgtca 120

gctgtctcac aggaag atg ctt cga gga tgg ggt ggc ccc agt gtg ggt gtg 172
                  Met Leu Arg Gly Trp Gly Gly Pro Ser Val Gly Val
                   1               5                  10

tct atg ggc acg gca ctg gga gtg ttg tgc ctc tgc ctt aca gga gct   220
Ser Met Gly Thr Ala Leu Gly Val Leu Cys Leu Cys Leu Thr Gly Ala
        15                  20                  25

gtg gag gtc caa gtc tct gaa gac cct gtg gtg gcc cta gtg gat acg   268
Val Glu Val Gln Val Ser Glu Asp Pro Val Val Ala Leu Val Asp Thr
    30                  35                  40

gat gcc acc cta cgc tgc tcc ttc tcc cca gag cct ggc ttc agc ctg   316
Asp Ala Thr Leu Arg Cys Ser Phe Ser Pro Glu Pro Gly Phe Ser Leu
45                  50                  55                  60

aga cag ctc aac ctc atc tgg cag ctg aca gac acc aaa cag ctg gtg   364
Arg Gln Leu Asn Leu Ile Trp Gln Leu Thr Asp Thr Lys Gln Leu Val
                65                  70                  75

cac agc ttc act gag ggc cgg gac caa ggc agt gcc tat gcc aac cgc   412
His Ser Phe Thr Glu Gly Arg Asp Gln Gly Ser Ala Tyr Ala Asn Arg
            80                  85                  90

acg gcg ctc ttc cct gac ttg ttg gtg cag ggc aat gca tcc ctg agg   460
Thr Ala Leu Phe Pro Asp Leu Leu Val Gln Gly Asn Ala Ser Leu Arg
        95                 100                 105

ctg cag cgt gtc cga gta acc gac gag ggc agc tac acc tgc ttt gtg   508
Leu Gln Arg Val Arg Val Thr Asp Glu Gly Ser Tyr Thr Cys Phe Val
    110                 115                 120

agc atc cag gac ttt gac agc gct gct gtt agc ctg cag gtg gcc gcc   556
Ser Ile Gln Asp Phe Asp Ser Ala Ala Val Ser Leu Gln Val Ala Ala
125                 130                 135                 140

ccc tac tca aag ccc agc atg acc ctg gag ccc aac aag gac ctg cgt   604
Pro Tyr Ser Lys Pro Ser Met Thr Leu Glu Pro Asn Lys Asp Leu Arg
                145                 150                 155

cca ggg gac atg gtg acc atc acg tgc tcc agc tac cag ggc tat ccc   652
Pro Gly Asp Met Val Thr Ile Thr Cys Ser Ser Tyr Gln Gly Tyr Pro
            160                 165                 170

gag gct gag gtg ttc tgg aag gac gga cag gga ttg ccc ttg act ggc   700
Glu Ala Glu Val Phe Trp Lys Asp Gly Gln Gly Leu Pro Leu Thr Gly
        175                 180                 185

aat gtg acc aca tcc cag atg gcc aac gag cgg ggc ctg ttc gat gtt   748
Asn Val Thr Thr Ser Gln Met Ala Asn Glu Arg Gly Leu Phe Asp Val
    190                 195                 200
```

FIG. 3B

```
cac agt gtg ctg agg gtg gtg ctg ggt gct aat ggc acc tac agc tgc    796
His Ser Val Leu Arg Val Val Leu Gly Ala Asn Gly Thr Tyr Ser Cys
205                 210                 215                 220

ctg gtc cgc aac ccg gtg ttg cag caa gat gct cat ggc tcg gtc acc    844
Leu Val Arg Asn Pro Val Leu Gln Gln Asp Ala His Gly Ser Val Thr
                225                 230                 235

atc aca ggg cag ccc atg aca ttc ccc cct gag gct cta tgg gtg act    892
Ile Thr Gly Gln Pro Met Thr Phe Pro Pro Glu Ala Leu Trp Val Thr
            240                 245                 250

gtg ggg ctc tct gtc tgt ctt gtg ata ctg ctg gtg gcc ctg gcc ttc    940
Val Gly Leu Ser Val Cys Leu Val Ile Leu Leu Val Ala Leu Ala Phe
        255                 260                 265

gtg tgc tgg aga aag atc aag cag agc tgt gaa gag gag aat gca ggt    988
Val Cys Trp Arg Lys Ile Lys Gln Ser Cys Glu Glu Glu Asn Ala Gly
    270                 275                 280

gct gag gac cag gat ggg gat gga gaa gga tcc aag aca gct ctt cgg    1036
Ala Glu Asp Gln Asp Gly Asp Gly Glu Gly Ser Lys Thr Ala Leu Arg
285                 290                 295                 300

cct ctg aaa cac tct gaa aac aaa gaa gat gac gga caa gaa ata gct    1084
Pro Leu Lys His Ser Glu Asn Lys Glu Asp Asp Gly Gln Glu Ile Ala
                305                 310                 315

tgactggaag ctgctgccct tccctggtgg gggggcccac cctctggctg tattgagcct 1144

caatgtgagc cctgcccccca atgaatgggt tttgttccac agatctaccc attctttaga 1204

ggacgtggtt tacaggctac ccacagcctt attttcccaa tggacttaat tcccatcatc 1264

ctgaagcctc ctttctccag tgacacgata cacgaaccat cctgcggcct tatttcttac 1324

ggactcgaca caaagagttc tccacctcag tgtccctcca gagtcatccg gtggccttgt 1384

gatactacac ggaccttcct tctgccttac tttaatagat atacacaaac catccccatg 1444

tccttgtgcc tccaaagcca tgcagagact gtattactgc tactattctc caaggcacat 1504

gctattcaga tgaacccctg ccttattcct ctgaagacag atgcttagtt acctcttggt 1564

tctttctccc atggccctga catatcttag tcacccatca acgatgggat cccatctctc 1624

agcaagtcct caacctgact ccctgccctc atctggccct ggctttggtt ttctccctcc 1684

ctaagtgaga tggggcacac tccccatcca cacacatggg tcacagctgt gcgtgctgga 1744

tcgcgtacat acttgccttg catggtctcc tctggctgcc ctgggctgtg ccctttctcg 1804

cctcaggaag caggtgctgg tcggcctggt tctcagggcc cctcagggag tcagccttca 1864

accctgtgct tcccgtgttg gaaatctttg ttacttttcc tttcttagta aattaacatc 1924
```

FIG. 3C

```
tgttgaacaa ccacagcgtc caacaggact ttcacagacc ctgccagcta gattaaataa 1984
tgatacagaa gtttattaat tattttaaag cttaggtttt tttgccggga ggtatcccaa 2044
atactctatc ccgactaatc ctggcactat gtcccaccac atggccaggc ctacctctgc 2104
tccactctga atcatccacc tctgtgtccg ccgacaaatc tcccatgatt cagttcttct 2164
cccagcgtcc ctatctctgc ccggaagtac gacctttgac ttcctgacca actattggcc 2224
gtcaactctt tgttaaaggt gatcagatat aattttgcct taggcacgtg aggaagaaac 2284
atatttataa aatacgagac cagagatggg ccatggaaat aacaccagat tctgacagcc 2344
tttagccctc tgctggtaca aattaacaat tgaatatata gagacacacc ttcacacagt 2404
gcaccccaac aacaggggtg agcattgtgc tgggtactag ggtcctgctg aaatcagaga 2464
ccttaactcc agctggggaa tggccttgct ccctgctgtg cccacagctt ccaacactgt 2524
ccctgacccc agggtagggg tggaaacctg gagaaggcac agccccttac cataccttga 2584
gaactgggta tttttcagag tctatatgtg tgcactggaa ggcaggtggc cacagccatg 2644
cagacctggg tagggtcaga agcctatgcc acgctgggac ctcctcaaca gctgaagtct 2704
gaggacaaga agggccttct tactgtggtg ctattctgga gctggggtat atacctggct 2764
tgtctctgac agccctggct tttggcagaa ctt                              2797
```

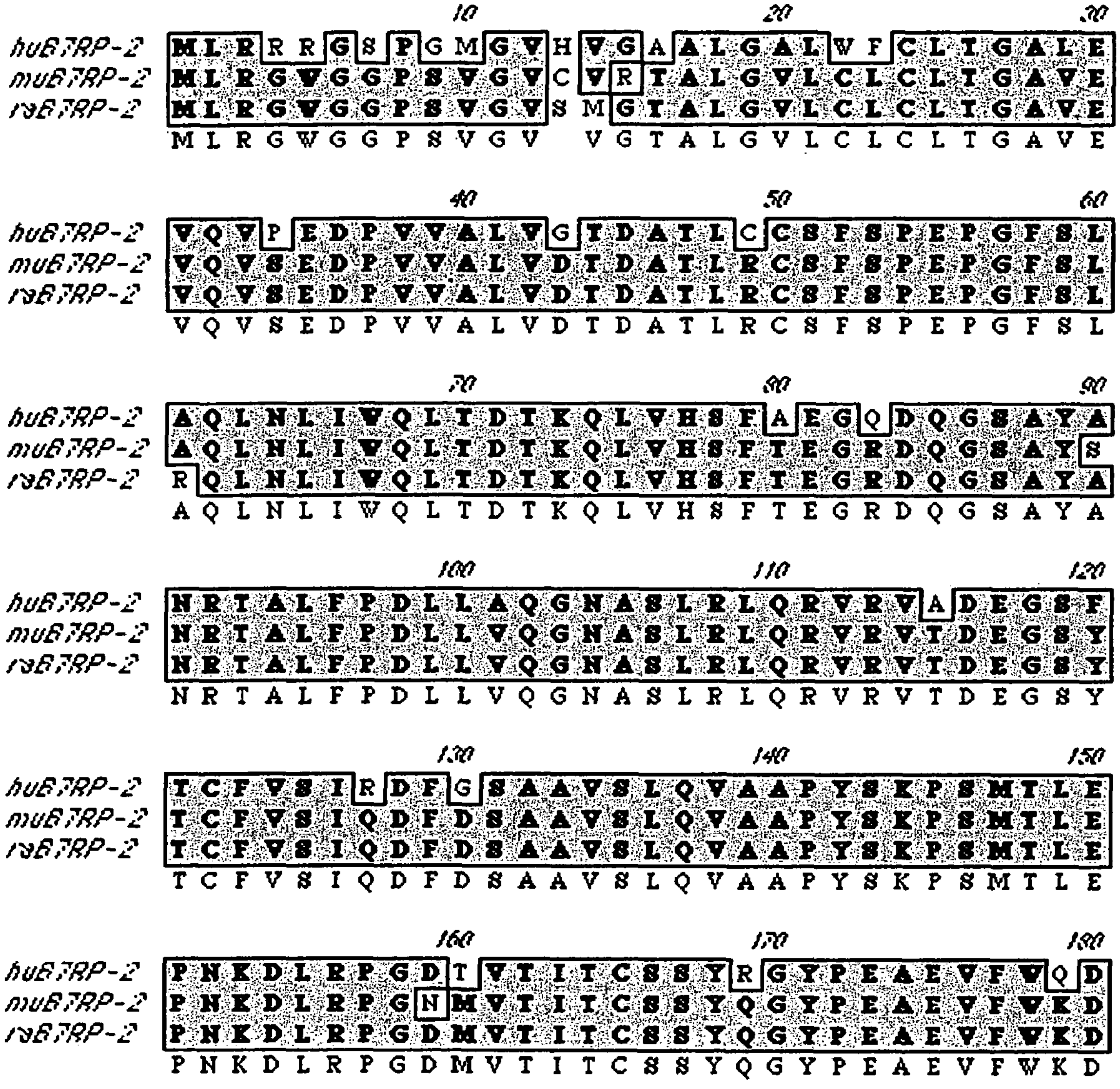

FIG. 4A

```
                        10                    20                    30
huBTRP-2   M L R R G S P G M G V H V G A A L G A L W F C L T G A L E
muBTRP-2   M L R G V G G P S V G V C V R T A L G V L C L C L T G A V E
rBTRP-2    M L R G V G G P S V G V S M G T A L G V L C L C L T G A V E
           M L R G W G P S V G V   V G T A L G V L C L C L T G A V E

                        40                    50                    60
huBTRP-2   V Q V P E D P V V A L V G T D A T L C C S F S P E P G F S L
muBTRP-2   V Q V S E D P V V A L V D T D A T L R C S F S P E P G F S L
rBTRP-2    V Q V S E D P V V A L V D T D A T L R C S F S P E P G F S L
           V Q V S E D P V V A L V D T D A T L R C S F S P E P G F S L

                        70                    80                    90
huBTRP-2   A Q L N L I W Q L T D T K Q L V H S F A E G Q D Q G S A Y A
muBTRP-2   A Q L N L I W Q L T D T K Q L V H S F T E G R D Q G S A Y S
rBTRP-2    R Q L N L I W Q L T D T K Q L V H S F T E G R D Q G S A Y A
           A Q L N L I W Q L T D T K Q L V H S F T E G R D Q G S A Y A

                       100                   110                   120
huBTRP-2   N R T A L F P D L L A Q G N A S L R L Q R V R V A D E G S F
muBTRP-2   N R T A L F P D L L V Q G N A S L R L Q R V R V T D E G S Y
rBTRP-2    N R T A L F P D L L V Q G N A S L R L Q R V R V T D E G S Y
           N R T A L F P D L L V Q G N A S L R L Q R V R V T D E G S Y

                       130                   140                   150
huBTRP-2   T C F V S I R D F G S A A V S L Q V A A P Y S K P S M T L E
muBTRP-2   T C F V S I Q D F D S A A V S L Q V A A P Y S K P S M T L E
rBTRP-2    T C F V S I Q D F D S A A V S L Q V A A P Y S K P S M T L E
           T C F V S I Q D F D S A A V S L Q V A A P Y S K P S M T L E

                       160                   170                   180
huBTRP-2   P N K D L R P G D T V T I T C S S Y R G Y P E A E V F W Q D
muBTRP-2   P N K D L R P G N M V T I T C S S Y Q G Y P E A E V F W K D
rBTRP-2    P N K D L R P G D M V T I T C S S Y Q G Y P E A E V F W K D
           P N K D L R P G D M V T I T C S S Y Q G Y P E A E V F W K D
```

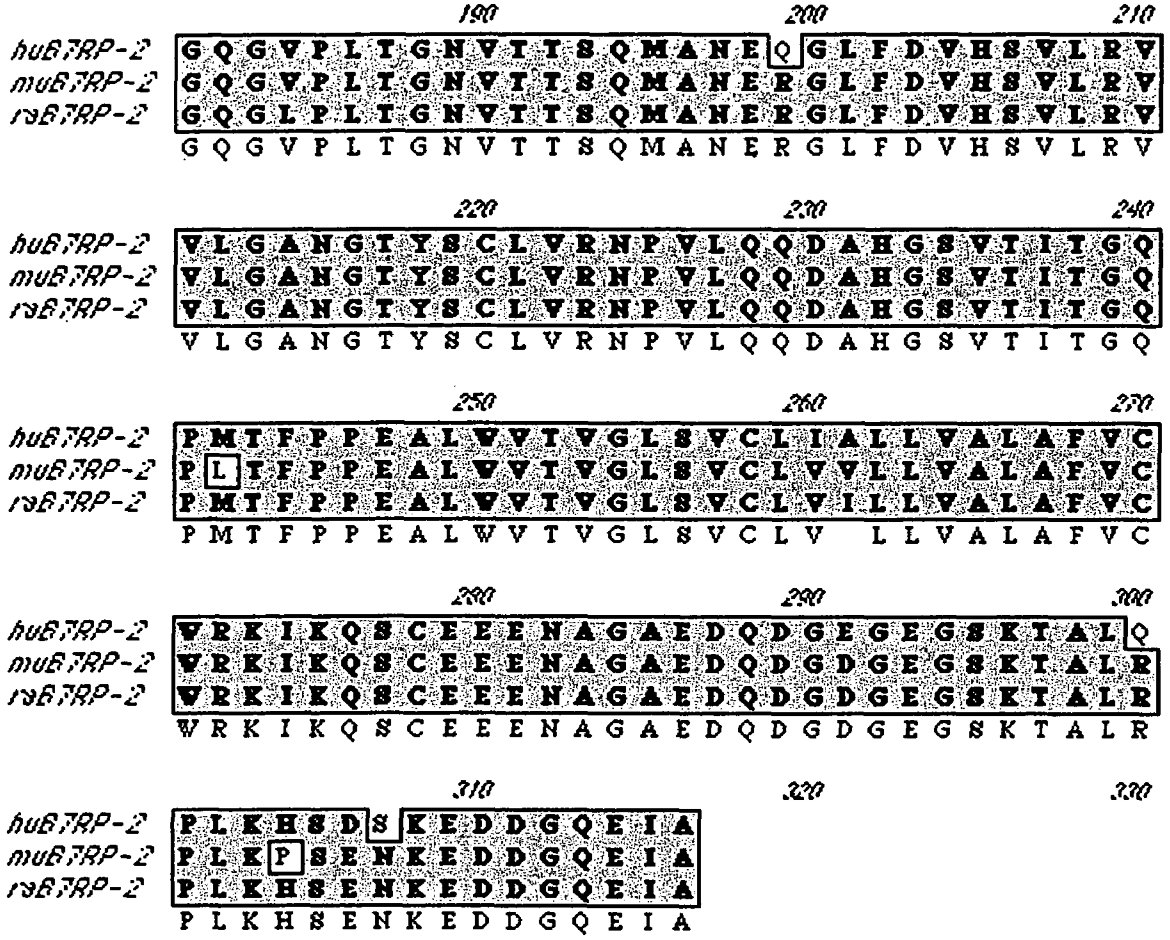

FIG. 4B

|         | 190 | 200 | 210 |
|---------|-----|-----|-----|
| huBTRP-2 | GQGVPLTGNVTTSQMANE|Q|GLFDVHSVLRV |
| muBTRP-2 | GQGVPLTGNVTTSQMANERGLFDVHSVLRV |
| rBTRP-2 | GQGLPLTGNVTTSQMANERGLFDVHSVLRV |
|         | GQGVPLTGNVTTSQMANERGLFDVHSVLRV |

|         | 220 | 230 | 240 |
|---------|-----|-----|-----|
| huBTRP-2 | VLGANGTYSCLVRNPVLQQDAHGSVTITGQ |
| muBTRP-2 | VLGANGTYSCLVRNPVLQQDAHGSVTITGQ |
| rBTRP-2 | VLGANGTYSCLVRNPVLQQDAHGSVTITGQ |
|         | VLGANGTYSCLVRNPVLQQDAHGSVTITGQ |

|         | 250 | 260 | 270 |
|---------|-----|-----|-----|
| huBTRP-2 | PMTFPPEALVVTVGLSVCLIALLVALAFVC |
| muBTRP-2 | P|L|TFPPEALVVTVGLSVCLVLLVALAFVC |
| rBTRP-2 | PMTFPPEALVVTVGLSVCLVILLVALAFVC |
|         | PMTFPPEALVVTVGLSVCLV LLVALAFVC |

|         | 280 | 290 | 300 |
|---------|-----|-----|-----|
| huBTRP-2 | WRKIKQSCEEENAGAEDQDGEGEGSKTAL|Q| |
| muBTRP-2 | WRKIKQSCEEENAGAEDQDGDGEGSKTALR |
| rBTRP-2 | WRKIKQSCEEENAGAEDQDGDGEGSKTALR |
|         | WRKIKQSCEEENAGAEDQDGDGEGSKTALR |

|         | 310 | 320 | 330 |
|---------|-----|-----|-----|
| huBTRP-2 | PLKHSDS|KEDDGQEIA |
| muBTRP-2 | PLK|P|SENKEDDGQEIA |
| rBTRP-2 | PLKHSENKEDDGQEIA |
|         | PLKHSENKEDDGQEIA |

FIG. 6A

```
             1                                                      50
hu_BTN1A1    --MAVFPSSG LPRCLLTLIL LQLPKLDS.A PFDVIGPPEP ILAVVGEDAE
bo_BTN       --MAVFPNSC LAGCLLIFIL LQLPKLDS.A PFDVIGPQEP ILAVVGEDAE
mu_BTN       --MAVPTNSC LLVCLLTLTV LQLPTLDSAA PFDVTAPQEP VLALVGSDAE
hu_BTN2A1    ~MESAAALHF SRPASLLLLL LSLCALVS.A QFIVVGPTDP ILATVGENTT
hu_BT3.2     MKMASSLAFL LLNFHVSLLL VQLLTPCS.A QFSVLGPSGP ILAMVGEDAD
hu_BTN3A2    MKMASSLAFL LLNFHVSLLL VQLLTPCS.A QFSVLGPSGP ILAMVGEDAD
gr_BG2       --MQMWLPAS PRGLLSYLVT LHVLRLGS.A NFSVVGPGHP LRVTVGQDVM
Hu_B7RP-2    --MLRRRGSP GMGVHVGAAL GALWFCLTGA .LEVQVPEDP VVALVGTDAT

             51                                                    100
hu_BTN1A1    LPCRLSPN.. ASAEHLELRW FRKKVSPAVL VHRDGREQEA EQMPEYRGRA
bo_BTN       LPCRLSPN.. VSAKGMELRW FREKVSPAVF VSREGQEQEG EEMAEYRGRV
mu_BTN       LTCGFSPN.. ASSEYMELLW FRQTRSTAVL LYRDGQEQEG QQMTEYRGRA
hu_BTN2A1    LRCHLSPE.. KNAEDMEVRW FRSQFSPAVF VYKGGRERTE EQMEEYRGRT
hu_BT3.2     LPCHLFPT.. MSAETMELKW VSSSLRQVVN VYADGKEVED RQSAPYRGRT
hu_BTN3A2    LPCHLFPT.. MSAETMELKW VSSSLRQVVN VYADGKEVED RQSAPYRGRT
gr_BG2       LPCHLSPS.. MEARSLDIRW IRHQVSEIVH RYRNGEDLYG DQMEEYVGRT
Hu_B7RP-2    LCCSFSPEPG FSLAQLNLIW QLTDTKQLVH SFAEGQD... .QGSAYANRT

             101                                                   150
hu_BTN1A1    TLVQDGIAKG RVALRIRGVR VSDDGEYTCF FREDGSYEEA LVHLKVAALG
bo_BTN       SLVEDHIAEG SVAVRIQEVK ASDDGEYRCF FRQDENYEEA IVHLKVAALG
mu_BTN       TLATAGLLDG RATLLIRDVR VSDQGEYRCL FKDNDDFEEA AVYLKVAAVG
hu_BTN2A1    TFVSKDISRG SVALVIHNIT AQENGTYRCY FQEGRSYDEA ILHLVVAGLG
hu_BT3.2     SILRDGITAG KAALRIHNVT ASDSGKYLCY FQDGDFYEKA LVELKVAALG
hu_BTN3A2    SILRDGITAG KAALRIHNVT ASDSGKYLCY FQDGDFYEKA LVELKVAALG
gr_BG2       ELVRDGLSRG RLDLRISGLR PSDDGQYVCT VRDGSSYGEA TVDLEVSATG
Hu_B7RP-2    ALFPDLLAQG NASLRLQRVR VADEGSFTCF VSIRD.FGSA AVSLQVAAPY

             151                                                   200
hu_BTN1A1    SDPHISMQVQ EN....GEIC LECTSVGWYP EPQVQWRTSK GEKFPS.TSE
bo_BTN       SDPHISMKVQ ES....GEIQ LECTSVGWYP EPQVQWRTHR GEEFPS.MSE
mu_BTN       SDPQISMTVQ EN....GEME LECTSSGWYP EPQVQWRTGN REMLPS.TSE
hu_BTN2A1    SKPLISMRGH ED....GGIR LECISRGWYP KPLTVWRDPY GGVAPA.LKE
hu_BT3.2     SNLHVEVKGY ED....GGIH LECRSTGWYP QPQIQWSNAK GENIPA.VEA
hu_BTN3A2    SNLHVEVKGY ED....GGIH LECRSTGWYP QPQIQWSNAK GENIPA.VEA
gr_BG2       SGPQLSLEAY ED....GGIR VVCRSAGWYP RPEVLWKDPG GQHLPS.VSQ
Hu_B7RP-2    SKPSMTLEPN KDLRPGDTVT ITCSSYRGYP EAEVFWQDGQ GVPLTGNVTT

             201                                                   250
hu_BTN1A1    SRNPDEEGLF TVAASVIIRD TSTKNV.SCY IQNLLLGQEK KVEISIPASS
bo_BTN       SRNPDEEGLF TVRASVIIRD SSMKNV.SCC IRNLLLGQEK EVEVSIPASF
mu_BTN       SKKHNEEGLF TVAVSMMIRD SSIKNM.SCC IQNILLGQGK EVEISLPAPF
hu_BTN2A1    VSMPDADGLF MVTTAVIIRD KSVRNM.SCS INNTLLGQKK ESVIFIPESF
hu_BT3.2     PVVADGVGLY EVAASVIMRG GSGEGV.SCI IRNSLLGLEK TASISIADPF
hu_BTN3A2    PVVADGVGLY EVAASVIMRG GSGEGV.SCI IRNSLLGLEK TASISIADPF
gr_BG2       RYSFDERGLF DTEDVIIVTD GNRDGKWSCV VRNSHLNQEQ ETSLHISAPF
Hu_B7RP-2    SQMANEQGLF DVH.SVLRVV LGANGTYSCL VRNPVLQQDA HGSVTITGQP

             251                                                   300
hu_BTN1A1    LPRLTPWIVA VAVILMVLGL LTIGSIFFTW RLYNERP... ..........
bo_BTN       FPRLTPWMVA VAVILVVLGL LTIGSIFFTW RLYKERS... ..........
mu_BTN       VPRLTPWIVA VAIILLALGF LTIGSIFFTW KLYKERS... ..........
hu_BTN2A1    MPSVSPCAVA LPIIVVILMI PIAVCIYWIN KLQKEKKILS GEKEFERETR
hu_BT3.2     FRSAQPWIAA LAGTLPILLL LLAGASYFLW RQQKEITALS SEIESEQEMK
hu_BTN3A2    FRSAQPWIAA LAGTLPILLL LLAGASYFLW RQQKEITALS SEIESEQEMK
gr_BG2       FHNARPWMVG VQ.VLLVLSG VLLGLGAYLW R.RKVLQSRE LE~~~~~~~~
Hu_B7RP-2    MTFPPEALWV TVGLSVCLIA LLVALAFVCW RKIKQSCEEE NAGAEDQDGE
```

FIG. 6B

```
            301                                                    350
hu_BTN1A1   .......... .RERRNEFSS KERLLEELKW KKATLHAVDV TLDPDTAHPH
bo_BTN      .......... .RQRRNEFSS KEKLLEELKW KRATLHAVDV TLDPDTAHPH
mu_BTN      .......... .SLRKKEFGS KERLLEELRC KKTVLHEVDV TLDPDTAHPH
hu_BTN2A1   EIALKELEKE RVQKEEELQV KEKLQEELRW RRTFLHAVDV VLDPDTAHPD
hu_BT3.2    EMGYAATERE ISLRESLQEE LKRKKIQYLT RGEESSSDTN KSALMLKWKK
hu_BTN3A2   EMGYAATERE ISLRESLQEE LKRKKSST-- ---------- ----------
gr_BG2      ~~~~~~~~~~ ~~~~~~~~~~ ~~~~~~~~~~ ~~~~~~~~~~ ~~~~~~~~~~
Hu_B7RP-2   GEGSKTALQP LKHSDSKEDD GQEIA*---- ---------- ----------

            351                                                    400
hu_BTN1A1   LFLYEDSKSV RLEDSR...Q KLPEKTERFD SWPCVLGRET FTSGRHYWEV
bo_BTN      LFLYEDSKSV RLEDSR...Q KLPEKPERFD SWPCVMGREA FTSGRHYWEV
mu_BTN      LFLYEDSKSV RLEDSR...Q ILPDRPERFD SWPCVLGRET FTSGRHYWEV
hu_BTN2A1   LFLSEDRRSV RRCPFRHLGE SVPDNPERFD SQPCVLGRES FASGKHYWEV
hu_BT3.2    ALLKPGEEML QMRLHLVK~~ ~~~~~~~~~~ ~~~~~~~~~~ ~~~~~~~~~~
hu_BTN3A2   ~~~~~~~~~~ ~~~~~~~~~~ ~~~~~~~~~~ ~~~~~~~~~~ ~~~~~~~~~~
gr_BG2      ~~~~~~~~~~ ~~~~~~~~~~ ~~~~~~~~~~ ~~~~~~~~~~ ~~~~~~~~~~
Hu_B7RP-2   ~~~~~~~~~~ ~~~~~~~~~~ ~~~~~~~~~~ ~~~~~~~~~~ ~~~~~~~~~~

            401                                                    450
hu_BTN1A1   EVGDRTDWAI GVCRENVMKK GFDPMTPENG FWAVELYGNG YWALTPLRTP
bo_BTN      EVGDRTDWAI GVCRENVMKK GFDPMTPENG FWAVELYGNG YWALTPLRTP
mu_BTN      EVGDRTDWAI GVCRENVVKK GFDPMTPDNG FWAVELYGNG YWALTPLRTS
hu_BTN2A1   EVENVIEWTV GVCRDSVERK GEVLLIPQNG FWTLEMHKGQ YRAVSSPDRI
hu_BT3.2    ~~~~~~~~~~ ~~~~~~~~~~ ~~~~~~~~~~ ~~~~~~~~~~ ~~~~~~~~~~
hu_BTN3A2   ~~~~~~~~~~ ~~~~~~~~~~ ~~~~~~~~~~ ~~~~~~~~~~ ~~~~~~~~~~
gr_BG2      ~~~~~~~~~~ ~~~~~~~~~~ ~~~~~~~~~~ ~~~~~~~~~~ ~~~~~~~~~~
Hu_B7RP-2   ~~~~~~~~~~ ~~~~~~~~~~ ~~~~~~~~~~ ~~~~~~~~~~ ~~~~~~~~~~

            451                                                    500
hu_BTN1A1   LPLAGPPRRV GIFLDYESGD ISFYNMNDGS DIYTFSNVTF SGPLRPFFCL
bo_BTN      LPLAGPPRRV GVFLDYESGD IFFYNMTDGS HIYTFSKASF SGPLRPFFCL
mu_BTN      LRLAGPPRRV GVFLDYDAGD ISFYNMSNGS LIYTFPSISF SGPLRPFFCL
hu_BTN2A1   LPLKESLCRV GVFLDYEAGD VSFYNMRDRS HIYTCPRSAF SVPVRPFFRL
hu_BT3.2    ~~~~~~~~~~ ~~~~~~~~~~ ~~~~~~~~~~ ~~~~~~~~~~ ~~~~~~~~~~
hu_BTN3A2   ~~~~~~~~~~ ~~~~~~~~~~ ~~~~~~~~~~ ~~~~~~~~~~ ~~~~~~~~~~
gr_BG2      ~~~~~~~~~~ ~~~~~~~~~~ ~~~~~~~~~~ ~~~~~~~~~~ ~~~~~~~~~~
Hu_B7RP-2   ~~~~~~~~~~ ~~~~~~~~~~ ~~~~~~~~~~ ~~~~~~~~~~ ~~~~~~~~~~

            501                                                    550
hu_BTN1A1   WSSGKKPLTI CPIADGPERV TVIANAQDLS KEIPLSPMGE ESAPRDADTL
bo_BTN      WSCGKKPLTI CPVTDGLEGV MVVADAKDIS KEIPLSPMGE DSASGDIETL
mu_BTN      WSCGKKPLTI CSTANGPEKV TVIANVQD.. .DIPLSPLGE GCTSGDKDTL
hu_BTN2A1   .GCEDSPIFI CPALTGANGV TVPEEGLTLH RVGTHQSL~~ ~~~~~~~~~~
hu_BT3.2    ~~~~~~~~~~ ~~~~~~~~~~ ~~~~~~~~~~ ~~~~~~~~~~ ~~~~~~~~~~
hu_BTN3A2   ~~~~~~~~~~ ~~~~~~~~~~ ~~~~~~~~~~ ~~~~~~~~~~ ~~~~~~~~~~
gr_BG2      ~~~~~~~~~~ ~~~~~~~~~~ ~~~~~~~~~~ ~~~~~~~~~~ ~~~~~~~~~~
Hu_B7RP-2   ~~~~~~~~~~ ~~~~~~~~~~ ~~~~~~~~~~ ~~~~~~~~~~ ~~~~~~~~~~

            551        564
hu_BTN1A1   HSKLIPTQPS QGAP
bo_BTN      HSKLIPLQPS QGVP
mu_BTN      HSKLIPFSPS QAAP
hu_BTN2A1   ~~~~~~~~~~ ~~~~
hu_BT3.2    ~~~~~~~~~~ ~~~~
hu_BTN3A2   ~~~~~~~~~~ ~~~~
gr_BG2      ~~~~~~~~~~ ~~~~
Hu_B7RP-2   ~~~~~~~~~~ ~~~~
```

DOWNREGULATION OF IMMUNE RESPONSE BY ADMINISTERING B7RP-2 FUSION PROTEIN

This is a continuation of application Ser. No. 10/156,424, filed May 28, 2002 now abandoned.

This application claims the benefit of priority from U.S. Provisional Patent Application No. 60/293,629, filed on May 25, 2001, the disclosure of which is explicitly incorporated by reference herein.

FIELD OF THE INVENTION

The present invention relates to B7 Related Protein-2 (B7RP-2) polypeptides and nucleic acid molecules encoding the same. The invention also relates to selective binding agents, vectors, host cells, and methods for producing B7RP-2 polypeptides. The invention further relates to pharmaceutical compositions and methods for the diagnosis, treatment, amelioration, and/or prevention of diseases, disorders, and conditions associated with B7RP-2 polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified. Accordingly, it is an object of the invention to identify novel polypeptides, and nucleic acid molecules encoding the same, which have diagnostic or therapeutic benefit.

SUMMARY OF THE INVENTION

The present invention relates to novel B7RP-2 nucleic acid molecules and encoded polypeptides.

The invention provides for an isolated nucleic acid molecule comprising:

(a) the nucleotide sequence as set forth in any of SEQ ID NO: 1, SEQ ID NO: 3, or SEQ ID NO: 5;

(b) a nucleotide sequence encoding the polypeptide as set forth in any of SEQ ID NO: 2, SEQ ID NO: 4, or SEQ ID NO: 6;

(c) a nucleotide sequence that hybridizes under at least moderately stringent conditions to the complement of the nucleotide sequence of either (a) or (b), wherein the encoded polypeptide has an activity of the polypeptide as set forth in any of SEQ ID NO: 2, SEQ ID NO: 4, or SEQ ID NO: 6; or (d) a nucleotide sequence complementary to the nucleotide sequence of any of (a)-(c).

The invention also provides for an isolated nucleic acid molecule comprising:

(a) a nucleotide sequence encoding a polypeptide that is at least about 70 percent identical to the polypeptide as set forth in any of SEQ ID NO: 2, SEQ ID NO: 4, or SEQ ID NO: 6, wherein the encoded polypeptide has an activity of the polypeptide set forth in any of SEQ ID NO: 2, SEQ ID NO: 4, or SEQ ID NO: 6;

(b) a nucleotide sequence encoding an allelic variant or splice variant of the nucleotide sequence as set forth in any of SEQ ID NO: 1, SEQ ID NO: 3, or SEQ ID NO: 5 or the nucleotide sequence of (a);

(c) a region of the nucleotide sequence of any of SEQ ID NO: 1, SEQ ID NO: 3, or SEQ ID NO: 5, or the nucleotide sequence of (a) or (b), encoding a polypeptide fragment of at least about 25 amino acid residues, wherein the polypeptide fragment has an activity of the encoded polypeptide as set forth in any of SEQ ID NO: 2, SEQ ID NO: 4, or SEQ ID NO: 6, or is antigenic;

(d) a region of the nucleotide sequence of any of SEQ ID NO: 1, SEQ ID NO: 3, or SEQ ID NO: 5 or the nucleotide sequence of any of (a)-(c) comprising a fragment of at least about 16 nucleotides;

(e) a nucleotide sequence that hybridizes under at least moderately stringent conditions to the complement of the nucleotide sequence of any of (a)-(d), wherein the encoded polypeptide has an activity of the polypeptide as set forth in any of SEQ ID NO: 2, SEQ ID NO: 4, or SEQ ID NO: 6; or (f) a nucleotide sequence complementary to the nucleotide sequence of any of (a)-(e).

The invention further provides for an isolated nucleic acid molecule comprising:

(a) a nucleotide sequence encoding a polypeptide as set forth in any of SEQ ID NO: 2, SEQ ID NO: 4, or SEQ ID NO: 6 with at least one conservative amino acid substitution, wherein the encoded polypeptide has an activity of the polypeptide set forth in any of SEQ ID NO: 2, SEQ ID NO: 4, or SEQ ID NO: 6;

(b) a nucleotide sequence encoding a polypeptide as set forth in any of SEQ ID NO: 2, SEQ ID NO: 4, or SEQ ID NO: 6 with at least one amino acid insertion, wherein the encoded polypeptide has an activity of the polypeptide set forth in any of SEQ ID NO: 2, SEQ ID NO: 4, or SEQ ID NO: 6;

(c) a nucleotide sequence encoding a polypeptide as set forth in any of SEQ ID NO: 2, SEQ ID NO: 4, or SEQ ID NO: 6 with at least one amino acid deletion, wherein the encoded polypeptide has an activity of the polypeptide set forth in any of SEQ ID NO: 2, SEQ ID NO: 4, or SEQ ID NO: 6;

(d) a nucleotide sequence encoding a polypeptide as set forth in any of SEQ ID NO: 2, SEQ ID NO: 4, or SEQ ID NO: 6 that has a C- and/or N-terminal truncation, wherein the encoded polypeptide has an activity of the polypeptide set forth in any of SEQ ID NO: 2, SEQ ID NO: 4, or SEQ ID NO: 6;

(e) a nucleotide sequence encoding a polypeptide as set forth in any of SEQ ID NO: 2, SEQ ID NO: 4, or SEQ ID NO: 6 with at least one modification that is an amino acid substitution, amino acid insertion, amino acid deletion, C-terminal truncation, or N-terminal truncation, wherein the encoded polypeptide has an activity of the polypeptide set forth in any of SEQ ID NO: 2, SEQ ID NO: 4, or SEQ ID NO: 6;

(f) a nucleotide sequence of any of (a)-(e) comprising a fragment of at least about 16 nucleotides;

(g) a nucleotide sequence that hybridizes under at least moderately stringent conditions to the complement of the nucleotide sequence of any of (a)-(f), wherein the encoded polypeptide has an activity of the polypeptide as set forth in any of SEQ ID NO: 2, SEQ ID NO: 4, or SEQ ID NO: 6; or (h) a nucleotide sequence complementary to the nucleotide sequence of any of (a)-(g).

The present invention provides for an isolated polypeptide comprising the amino acid sequence as set forth in any of SEQ ID NO: 2, SEQ ID NO: 4, or SEQ ID NO: 6.

The invention also provides for an isolated polypeptide comprising:

(a) an amino acid sequence for an ortholog of any of SEQ ID NO: 2, SEQ ID NO: 4, or SEQ ID NO: 6;

(b) an amino acid sequence which is at least about 70 percent identical to the amino acid sequence of any of SEQ ID NO: 2, SEQ ID NO: 4, or SEQ ID NO: 6, wherein the polypeptide has an activity of the polypeptide set forth in any of SEQ ID NO: 2, SEQ ID NO: 4, or SEQ ID NO: 6;

(c) a fragment of the amino acid sequence set forth in any of SEQ ID NO: 2, SEQ ID NO: 4, or SEQ ID NO: 6 comprising at least about 25 amino acid residues, wherein the fragment has an activity of the polypeptide set forth in any of SEQ ID NO: 2, SEQ ID NO: 4, or SEQ ID NO: 6, or is antigenic; or (d) an amino acid sequence for an allelic variant or splice variant of the amino acid sequence as set forth in any of SEQ ID NO: 2, SEQ ID NO: 4, or SEQ ID NO: 6, or the amino acid sequence of either (a) or (b).

The invention further provides for an isolated polypeptide comprising:

(a) the amino acid sequence as set forth in any of SEQ ID NO: 2, SEQ ID NO: 4, or SEQ ID NO: 6 with at least one conservative amino acid substitution, wherein the polypeptide has an activity of the polypeptide set forth in any of SEQ ID NO: 2, SEQ ID NO: 4, or SEQ ID NO: 6;

(b) the amino acid sequence as set forth in any of SEQ ID NO: 2, SEQ ID NO: 4, or SEQ ID NO: 6 with at least one amino acid insertion, wherein the polypeptide has an activity of the polypeptide set forth in any of SEQ ID NO: 2, SEQ ID NO: 4, or SEQ ID NO: 6;

(c) the amino acid sequence as set forth in any of SEQ ID NO: 2, SEQ ID NO: 4, or SEQ ID NO: 6 with at least one amino acid deletion, wherein the polypeptide has an activity of the polypeptide set forth in any of SEQ ID NO: 2, SEQ ID NO: 4, or SEQ ID NO: 6;

(d) the amino acid sequence as set forth in any of SEQ ID NO: 2, SEQ ID NO: 4, or SEQ ID NO: 6 that has a C- and/or N-terminal truncation, wherein the polypeptide has an activity of the polypeptide set forth in any of SEQ ID NO: 2, SEQ ID NO: 4, or SEQ ID NO: 6; or (e) the amino acid sequence as set forth in any of SEQ ID NO: 2, SEQ ID NO: 4, or SEQ ID NO: 6 with at least one modification that is an amino acid substitution, amino acid insertion, amino acid deletion, C-terminal truncation, or N-terminal truncation, wherein the polypeptide has an activity of the polypeptide set forth in any of SEQ ID NO: 2, SEQ ID NO: 4, or SEQ ID NO: 6.

The invention still further provides for an isolated polypeptide comprising the amino acid sequence as set forth in SEQ ID NO: 2 with at least one conservative amino acid substitution that is a valine at position 20; valine at position 29; valine at position 101; tyrosine at position 120; leucine at position 184; valine at position 260; valine or isoleucine at position 261; aspartic acid at position 291; or glutamic acid at position 306; wherein the polypeptide has an activity of the polypeptide set forth in SEQ ID NO: 2.

Also provided are fusion polypeptides comprising B7RP-2 amino acid sequences.

The present invention also provides for an expression vector comprising the isolated nucleic acid molecules as set forth herein, recombinant host cells comprising the recombinant nucleic acid molecules as set forth herein, and a method of producing a B7RP-2 polypeptide comprising culturing the host cells and optionally isolating the polypeptide so produced.

A transgenic non-human animal comprising a nucleic acid molecule encoding a B7RP-2 polypeptide is also encompassed by the invention. The B7RP-2 nucleic acid molecules are introduced into the animal in a manner that allows expression and increased levels of a B7RP-2 polypeptide, which may include increased circulating levels. Alternatively, the B7RP-2 nucleic acid molecules are introduced into the animal in a manner that prevents expression of endogenous B7RP-2 polypeptide (i.e., generates a transgenic animal possessing a B7RP-2 polypeptide gene knockout). The transgenic non-human animal is preferably a mammal, and more preferably a rodent, such as a rat or a mouse.

Also provided are derivatives of the B7RP-2 polypeptides of the present invention.

Additionally provided are selective binding agents such as antibodies and peptides capable of specifically binding the B7RP-2 polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The B7RP-2 polypeptides and nucleic acid molecules of the present invention may be used to treat, prevent, ameliorate, and/or detect diseases and disorders, including those recited herein.

The present invention also provides a method of assaying test molecules to identify a test molecule that binds to a B7RP-2 polypeptide. The method comprises contacting a B7RP-2 polypeptide with a test molecule to determine the extent of binding of the test molecule to the polypeptide. The method further comprises determining whether such test molecules are agonists or antagonists of a B7RP-2 polypeptide. The present invention further provides a method of testing the impact of molecules on the expression of B7RP-2 polypeptide or on the activity of B7RP-2 polypeptide.

Methods of regulating expression and modulating (i.e., increasing or decreasing) levels of a B7RP-2 polypeptide are also encompassed by the invention. One method comprises administering to an animal a nucleic acid molecule encoding a B7RP-2 polypeptide. In another method, a nucleic acid molecule comprising elements that regulate or modulate the expression of a B7RP-2 polypeptide may be administered. Examples of these methods include gene therapy, cell therapy, and anti-sense therapy as further described herein.

In another aspect of the present invention, the B7RP-2 polypeptides may be used for identifying receptors thereof ("B7RP-2 polypeptide receptors"). Various forms of "expression cloning" have been extensively used to clone receptors for protein ligands. See, e.g., Simonsen and Lodish, 1994, *Trends Pharmacol. Sci.* 15:437-41 and Tartaglia et al., 1995, *Cell* 83:1263-71. The isolation of a B7RP-2 polypeptide receptor is useful for identifying or developing novel agonists and antagonists of the B7RP-2 polypeptide signaling pathway. Such agonists and antagonists include soluble B7RP-2 polypeptide receptors, anti-B7RP-2 polypeptide receptor-selective binding agents (such as antibodies and derivatives thereof), small molecules, and antisense oligonucleotides, any of which can be used for treating one or more disease or disorder, including those disclosed herein.

BRIEF DESCRIPTION OF THE FIGURES

FIGS. 1A-1B illustrate the nucleotide sequence of the human B7RP-2 gene (SEQ ID NO: 1) and the deduced amino acid sequence of human B7RP-2 polypeptide (SEQ ID NO: 2);

FIGS. 2A-2B illustrate the nucleotide sequence of the murine B7RP-2 gene (SEQ ID NO: 3) and the deduced amino acid sequence of the murine B7RP-2 polypeptide (SEQ ID NO: 4);

FIGS. 3A-3C illustrate the nucleotide sequence of the rat B7RP-2 gene (SEQ ID NO: 5) and the deduced amino acid sequence of rat B7RP-2 polypeptide (SEQ ID NO: 6);

FIGS. 4A-4B illustrate the amino acid sequence alignment of human B7RP-2 polypeptide (huB7RP-2; SEQ ID NO: 2), murine B7RP-2 polypeptide (muB7RP-2; SEQ ID NO: 4), and rat B7RP-2 polypeptide (raB7RP-2; SEQ ID NO: 6), which was prepared using the ClustalW algorithm. The sequences were aligned using the application MacVector™ 7.1.1 (Accelrys, Inc., Cambridge, UK) at the default settings. Conserved residues are boxed;

FIGS. 6A-6B illustrate the amino acid sequence alignment of human butyrophilin, subfamily 1, member A1 (hu_BTN1A1; SEQ ID NO: 7; GenBank Accession No. NP__001723), bovine butyrophilin precursor (bo_BTN; SEQ ID NO: 8; GenBank Accession No. P18892), murine butyrophilin (mu_BTN; SEQ ID NO: 9; GenBank Accession No. NP__038511), human butyrophilin, subfamily 2, member A1 (hu_BTN2A1; SEQ ID NO: 10; Accession No. NP__008980), human butyrophilin-like protein (hu_BT3.2; SEQ ID NO: 11; GenBank Accession No. ACC02652), human butyrophilin, subfamily 3, member A2 (hu_BTN3A2; SEQ ID NO: 12; GenBank Accession No. NP__008978), *Grus americana* B-G-like protein (gr_BG2; SEQ ID NO: 13; GenBank Accession No. AF033107), and human B7RP-2 polypeptide (hu_B7RP-2; SEQ ID NO: 2);

DETAILED DESCRIPTION OF THE INVENTION

Figure 5:
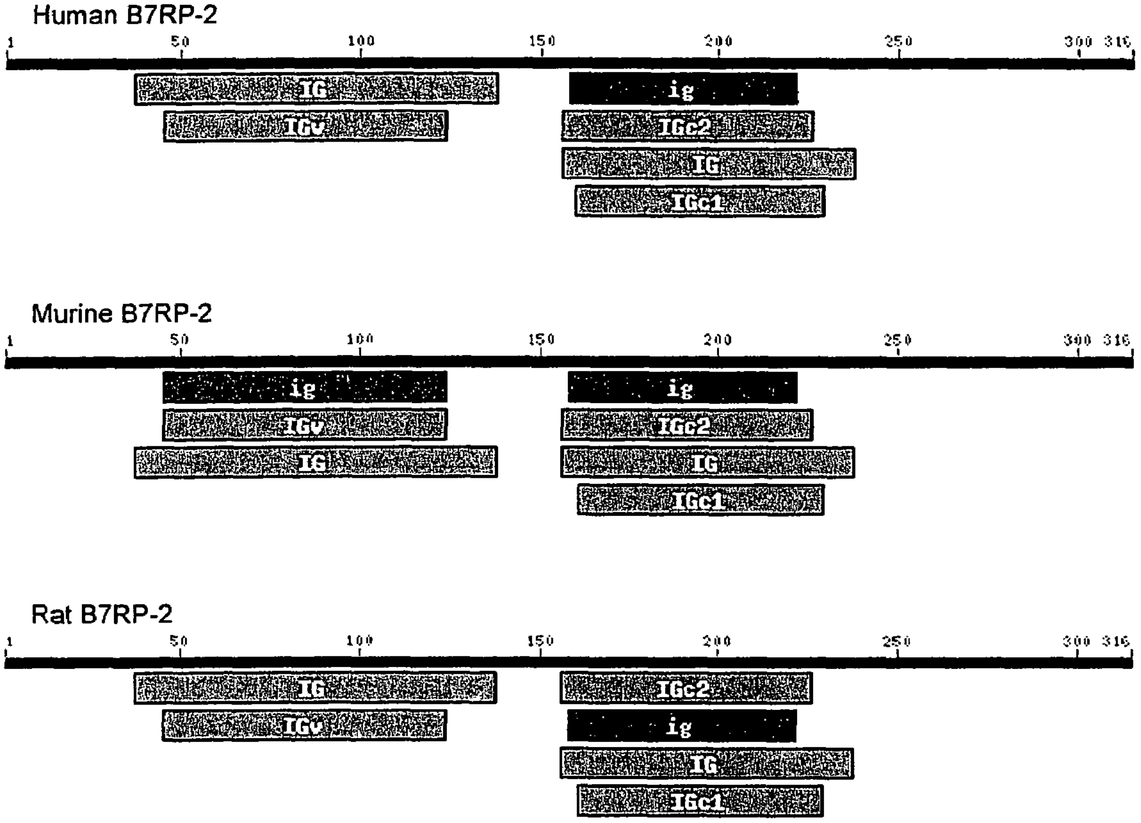
FIG. 5 illustrates the locations of several conserved domains possessed by human B7RP-2 polypeptide (SEQ ID NO: 2), murine B7RP-2 polypeptide (SEQ ID NO: 4), and rat B7RP-2 polypeptide (SEQ ID NO: 6), as indicated following a BLAST analysis of the amino acid sequences against the Conserved Domain Database.

The section headings used herein are for organizational purposes only and are not to be construed as limiting the subject matter described. All references cited in this application are expressly incorporated by reference herein.

Definitions

The terms "B7RP-2 gene" or "B7RP-2 nucleic acid molecule" or "B7RP-2 polynucleotide" refer to a nucleic acid molecule comprising or consisting of a nucleotide sequence as set forth in any of SEQ ID NO: 1, SEQ ID NO: 3, or SEQ ID NO: 5, a nucleotide sequence encoding the polypeptide as set forth in any of SEQ ID NO: 2, SEQ ID NO: 4, or SEQ ID NO: 6, and nucleic acid molecules as defined herein.

The term "B7RP-2 polypeptide allelic variant" refers to one of several possible naturally occurring alternate forms of a gene occupying a given locus on a chromosome of an organism or a population of organisms.

The term "B7RP-2 polypeptide splice variant" refers to a nucleic acid molecule, usually RNA, which is generated by alternative processing of intron sequences in an RNA transcript of B7RP-2 polypeptide amino acid sequence as set forth in any of SEQ ID NO: 2, SEQ ID NO: 4, or SEQ ID NO: 6.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "B7RP-2 polypeptide" refers to a polypeptide comprising the amino acid sequence of any of SEQ ID NO: 2, SEQ ID NO: 4, or SEQ ID NO: 6 and related polypeptides. Related polypeptides include B7RP-2 polypeptide fragments, B7RP-2 polypeptide orthologs, B7RP-2 polypeptide variants, and B7RP-2 polypeptide derivatives, which possess at least one activity of the polypeptide as set forth in any of SEQ ID NO: 2, SEQ ID NO: 4, or SEQ ID NO: 6. B7RP-2 polypeptides may be mature polypeptides, as defined herein, and may or may not have an amino-terminal methionine residue, depending on the method by which they are prepared.

The term "B7RP-2 polypeptide fragment" refers to a polypeptide that comprises a truncation at the amino-terminus (with or without a leader sequence) and/or a truncation at the carboxyl-terminus of the polypeptide as set forth in any of SEQ ID NO: 2, SEQ ID NO: 4, or SEQ ID NO: 6. The term "B7RP-2 polypeptide fragment" also refers to amino-terminal and/or carboxyl-terminal truncations of B7RP-2 polypeptide orthologs, B7RP-2 polypeptide derivatives, or B7RP-2 polypeptide variants, or to amino-terminal and/or carboxyl-terminal truncations of the polypeptides encoded by B7RP-2 polypeptide allelic variants or B7RP-2 polypeptide splice variants. B7RP-2 polypeptide fragments may result from alternative RNA splicing or from in vivo protease activity. Membrane-bound forms of a B7RP-2 polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or more than about 150 amino acids. Such B7RP-2 polypeptide fragments may optionally comprise an amino-terminal methionine residue. It will be appreciated that such fragments can be used, for example, to generate antibodies to B7RP-2 polypeptides.

The term "B7RP-2 polypeptide ortholog" refers to a polypeptide from another species that corresponds to B7RP-2 polypeptide amino acid sequence as set forth in any of SEQ ID NO: 2, SEQ ID NO: 4, or SEQ ID NO: 6. For example, mouse and human B7RP-2 polypeptides are considered orthologs of each other.

The term "B7RP-2 polypeptide variants" refers to B7RP-2 polypeptides comprising amino acid sequences having one or more amino acid sequence substitutions, deletions (such as internal deletions and/or B7RP-2 polypeptide fragments), and/or additions (such as internal additions and/or B7RP-2 fusion polypeptides) as compared to the B7RP-2 polypeptide amino acid sequence set forth in any of SEQ ID NO: 2, SEQ ID NO: 4, or SEQ ID NO: 6 (with or without a leader sequence). Variants may be naturally occurring (e.g., B7RP-2 polypeptide allelic variants, B7RP-2 polypeptide orthologs, and B7RP-2 polypeptide splice variants) or artificially constructed. Such B7RP-2 polypeptide variants may be prepared from the corresponding nucleic acid molecules having a DNA sequence that varies accordingly from the DNA sequence as set forth in any of SEQ ID NO: 1, SEQ ID NO: 3, or SEQ ID NO: 5. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "B7RP-2 polypeptide derivatives" refers to the polypeptide as set forth in any of SEQ ID NO: 2, SEQ ID NO: 4, or SEQ ID NO: 6, B7RP-2 polypeptide fragments, B7RP-2 polypeptide orthologs, or B7RP-2 polypeptide variants, as defined herein, that have been chemically modified. The term "B7RP-2 polypeptide derivatives" also refers to the polypeptides encoded by B7RP-2 polypeptide allelic variants or B7RP-2 polypeptide splice variants, as defined herein, that have been chemically modified.

The term "mature B7RP-2 polypeptide" refers to a B7RP-2 polypeptide lacking a leader sequence. A mature B7RP-2 polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like.

The term "B7RP-2 fusion polypeptide" refers to a fusion of one or more amino acids (such as a heterologous protein or peptide) at the amino- or carboxyl-terminus of the polypeptide as set forth in any of SEQ ID NO: 2, SEQ ID NO: 4, or SEQ ID NO: 6, B7RP-2 polypeptide fragments, B7RP-2 polypeptide orthologs, B7RP-2 polypeptide variants, or B7RP-2 derivatives, as defined herein. The term "B7RP-2 fusion polypeptide" also refers to a fusion of one or more amino acids at the amino- or carboxyl-terminus of the polypeptide encoded by B7RP-2 polypeptide allelic variants or B7RP-2 polypeptide splice variants, as defined herein.

The term "biologically active B7RP-2 polypeptides" refers to B7RP-2 polypeptides having at least one activity characteristic of the polypeptide comprising the amino acid sequence of any of SEQ ID NO: 2, SEQ ID NO: 4, or SEQ ID NO: 6. In addition, a B7RP-2 polypeptide may be active as an immunogen; that is, the B7RP-2 polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The terms "effective amount" and "therapeutically effective amount" each refer to the amount of a B7RP-2 polypeptide or B7RP-2 nucleic acid molecule used to support an observable level of one or more biological activities of the B7RP-2 polypeptides as set forth herein.

The term "pharmaceutically acceptable carrier" or "physiologically acceptable carrier" as used herein refers to one or more formulation materials suitable for accomplishing or enhancing the delivery of the B7RP-2 polypeptide, B7RP-2 nucleic acid molecule, or B7RP-2 selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for a B7RP-2 polypeptide. As used herein, the terms, "specific" and "specificity" refer to the ability of the selective binding agents to bind to human B7RP-2 polypeptides and not to bind to human non-B7RP-2 polypeptides. It will be appreciated, however, that the selective binding agents may also bind orthologs of the polypeptide as set forth in any of SEQ ID NO: 2, SEQ ID NO: 4, or SEQ ID NO: 6, that is, interspecies versions thereof, such as mouse and rat B7RP-2 polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of any of SEQ ID NO: 1, SEQ ID NO: 3, or SEQ ID NO: 5, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in any of SEQ ID NO: 2, SEQ ID NO: 4, or SEQ ID NO: 6. Such related B7RP-2 polypeptides may comprise, for example, an addition and/or a deletion of one or more N-linked or O-linked glycosylation sites or an addition and/or a deletion of one or more cysteine residues.

Related nucleic acid molecules also include fragments of B7RP-2 nucleic acid molecules which encode a polypeptide of at least about 25 contiguous amino acids, or about 50 amino acids, or about 75 amino acids, or about 100 amino acids, or about 150 amino acids, or more than about 150 amino acid residues of the B7RP-2 polypeptide of any of SEQ ID NO: 2, SEQ ID NO: 4, or SEQ ID NO: 6.

In addition, related B7RP-2 nucleic acid molecules also include those molecules which comprise nucleotide sequences which hybridize under moderately or highly stringent conditions as defined herein with the fully complementary sequence of the B7RP-2 nucleic acid molecule of any of SEQ ID NO: 1, SEQ ID NO: 3, or SEQ ID NO: 5, or of a molecule encoding a polypeptide, which polypeptide comprises the amino acid sequence as shown in any of SEQ ID NO: 2, SEQ ID NO: 4, or SEQ ID NO: 6, or of a nucleic acid fragment as defined herein, or of a nucleic acid fragment encoding a polypeptide as defined herein. Hybridization probes may be prepared using the B7RP-2 sequences provided herein to screen cDNA, genomic or synthetic DNA libraries for related sequences. Regions of the DNA and/or amino acid sequence of B7RP-2 polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°\ C.)=81.5+16.6(\log[Na+])+0.41(\%\ G+C)-600/N-0.72(\%\ formamide)$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm=2°\ C.\ \text{per}\ A\text{-}T\ \text{base pair}+4°\ C.\ \text{per}\ G\text{-}C\ \text{base pair}$$

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is at least about 70 percent identical to the nucleotide sequence as shown in any of SEQ ID NO: 1, SEQ ID NO: 3, or SEQ ID NO: 5, or comprise or consist essentially of a nucleotide sequence encoding a polypeptide that is at least about 70 percent identical to the polypeptide as set forth in any of SEQ ID NO: 2, SEQ ID NO: 4, or SEQ ID NO: 6. In preferred embodiments, the nucleotide sequences are about 75 percent, or about 80 percent, or about 85 percent, or about 90 percent, or about 95, 96, 97, 98, or 99 percent identical to the nucleotide sequence as shown in any of SEQ ID NO: 1, SEQ ID NO: 3, or SEQ ID NO: 5, or the nucleotide sequences encode a polypeptide that is about 75 percent, or about 80 percent, or about 85 percent, or about 90 percent, or about 95, 96, 97, 98, or 99 percent identical to the polypeptide sequence as set forth in any of SEQ ID NO: 2, SEQ ID NO: 4, or SEQ ID NO: 6. Related nucleic acid molecules encode polypeptides possessing at least one activity of the polypeptide set forth in any of SEQ ID NO: 2, SEQ ID NO: 4, or SEQ ID NO: 6.

Differences in the nucleic acid sequence may result in conservative and/or non-conservative modifications of the amino acid sequence relative to the amino acid sequence of any of SEQ ID NO: 2, SEQ ID NO: 4, or SEQ ID NO: 6.

Conservative modifications to the amino acid sequence of any of SEQ ID NO: 2, SEQ ID NO: 4, or SEQ ID NO: 6 (and the corresponding modifications to the encoding nucleotides) will produce a polypeptide having functional and chemical characteristics similar to those of B7RP-2 polypeptides. In contrast, substantial modifications in the functional and/or chemical characteristics of B7RP-2 polypeptides may be accomplished by selecting substitutions in the amino acid sequence of any of SEQ ID NO: 2, SEQ ID NO: 4, or SEQ ID NO: 6 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human B7RP-2 polypeptide that are homologous with non-human B7RP-2 polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the B7RP-2 polypeptide, or to increase or decrease the affinity of the B7RP-2 polypeptides described herein. Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NO: 2, SEQ ID NO: 4, or SEQ ID NO: 6 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a B7RP-2 polypeptide to such similar polypeptides. With such a comparison, one can identify residues and portions of the molecules that are conserved among similar polypeptides. It will be appreciated that changes in areas of the B7RP-2 molecule that are not conserved relative to such similar polypeptides would be less likely to adversely affect the biological activity and/or structure of a B7RP-2 polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a B7RP-2 polypeptide that correspond to amino acid residues that are important for activity or structure in similar polypeptides. One skilled in the art may opt for chemically similar amino acid substitutions for such predicted important amino acid residues of B7RP-2 polypeptides.

One skilled in the art can also analyze the three-dimensional structure and amino acid sequence in relation to that structure in similar polypeptides. In view of such information, one skilled in the art may predict the alignment of amino acid residues of B7RP-2 polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol. Relat. Areas Mol. Biol.* 47:45-48; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins which have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science,* 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred B7RP-2 polypeptide variants include glycosylation variants wherein the number and/or type of glycosylation sites have been altered compared to the amino acid sequence set forth in any of SEQ ID NO: 2, SEQ ID NO: 4, or SEQ ID NO: 6. In one embodiment, B7RP-2 polypeptide variants comprise a greater or a lesser number of N-linked glycosylation sites than the amino acid sequence set forth in any of SEQ ID NO: 2, SEQ ID NO: 4, or SEQ ID NO: 6. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred B7RP-2 variants include cysteine variants, wherein one or more cysteine residues are deleted or substituted with another amino acid (e.g., serine) as compared to the amino acid sequence set forth in any of SEQ ID NO: 2, SEQ ID NO: 4, or SEQ ID NO: 6. Cysteine variants are useful when B7RP-2 polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, related nucleic acid molecules comprise or consist of a nucleotide sequence encoding a polypeptide as set forth in any of SEQ ID NO: 2, SEQ ID NO: 4, or SEQ ID NO: 6 with at least one amino acid insertion and wherein the polypeptide has an activity of the polypeptide set forth in any of SEQ ID NO: 2, SEQ ID NO: 4, or SEQ ID NO: 6, or a nucleotide sequence encoding a polypeptide as set forth in any of SEQ ID NO: 2, SEQ ID NO: 4, or SEQ ID NO: 6 with at least one amino acid deletion and wherein the polypeptide has an activity of the polypeptide set forth in any of SEQ BD NO: 2, SEQ ID NO: 4, or SEQ ID NO: 6. Related nucleic acid molecules also comprise or consist of a nucleotide sequence encoding a polypeptide as set forth in any of SEQ ID NO: 2, SEQ ID NO: 4, or SEQ ID NO: 6 wherein the polypeptide has a carboxyl- and/or amino-terminal truncation and further wherein the polypeptide has an activity of the polypeptide set forth in any of SEQ ID NO: 2, SEQ ID NO: 4, or SEQ ID NO: 6. Related nucleic acid molecules also comprise or consist of a nucleotide sequence encoding a polypeptide as set forth in any of SEQ ID NO: 2, SEQ ID NO: 4, or SEQ ID NO: 6 with at least one modification selected from the group consisting of amino acid substitutions, amino acid insertions, amino acid deletions, carboxyl-terminal truncations, and amino-terminal truncations and wherein the polypeptide has an activity of the polypeptide set forth in any of SEQ ID NO: 2, SEQ ID NO: 4, or SEQ ID NO: 6.

In addition, the polypeptide comprising the amino acid sequence of any of SEQ ID NO: 2, SEQ ID NO: 4, or SEQ ID NO: 6, or other B7RP-2 polypeptide, may be fused to a homologous polypeptide to form a homodimer or to a heterologous polypeptide to form a heterodimer. Heterologous peptides and polypeptides include, but are not limited to: an epitope to allow for the detection and/or isolation of a B7RP-2 fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in any of SEQ ID NO: 2, SEQ ID NO: 4, or SEQ ID NO: 6, or other B7RP-2 polypeptide.

Fusions can be made either at the amino-terminus or at the carboxyl-terminus of the polypeptide comprising the amino acid sequence set forth in any of SEQ ID NO: 2, SEQ ID NO: 4, or SEQ ID NO: 6, or other B7RP-2 polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of any of SEQ ID NO: 2, SEQ ID NO: 4, or SEQ ID NO: 6, or other B7RP-2 polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, *Nature* 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154:5590-600 |
| IgG1 | TNF receptor | septic shock | Fisher et al., 1996, N. Engl. J. Med. 334: 1697-1702; Van Zee et al., 1996, J. Immunol. 156: 2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, Nature 337: 525-31 |
| IgG1, IgG3 | N-terminus of IL-2 | anti-cancer, antiviral | Harvill et al., 1995, Immunotech. 1:95-105 |
| IgG1 | C-terminus of OPG | osteoarthritis; bone density | WO 97/23614 |
| IgG1 | N-terminus of leptin | anti-obesity | PCT/US 97/23183, filed Dec. 11, 1997 |
| Human Ig Cγ1 | CTLA-4 | autoimmune disorders | Linsley, 1991, J. Exp. Med., 174:561-69 |

In one example, a human IgG hinge, CH2, and CH3 region may be fused at either the amino-terminus or carboxyl-terminus of the B7RP-2 polypeptides using methods known to the skilled artisan. In another example, a human IgG hinge, CH2, and CH3 region may be fused at either the amino-terminus or carboxyl-terminus of a B7RP-2 polypeptide fragment (e.g., the predicted extracellular portion of B7RP-2 polypeptide).

The resulting B7RP-2 fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heijne, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG™ program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978)(PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:

Algorithm: Needleman and Wunsch, 1970, *J. Mol. Biol.* 48:443-53;

Comparison matrix: BLOSUM 62 (Henikoff et al., supra);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:

Algorithm: Needleman and Wunsch, supra;

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, WISCONSIN PACKAGE™, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a B7RP-2 polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of a B7RP-2 polypeptide has been identified from one species, all or a portion of that gene may be used as a probe to identify orthologs or related genes from the same species. The probes or primers may be used to screen cDNA libraries from various tissue sources believed to express the B7RP-2 polypeptide. In addition, part or all of a nucleic acid molecule having the sequence as set forth in any of SEQ ID NO: 1, SEQ ID NO: 3, or SEQ ID NO: 5 may be used to screen a genomic library to identify and isolate a gene encoding the amino acid sequence of a B7RP-2 polypeptide. Typically, conditions of moderate or high stringency will be employed for screening to minimize the number of false positives obtained from the screening.

Nucleic acid molecules encoding the amino acid sequence of B7RP-2 polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a B7RP-2 polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a B7RP-2 polypeptide can be inserted into an expression vector. By introducing the expression vector into an appropriate host, the encoded B7RP-2 polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA encoding the amino acid sequence of a B7RP-2 polypeptide, are then added to the cDNA along with a polymerase such as Taq polymerase, and the polymerase amplifies the cDNA region between the two primers.

Another means of preparing a nucleic acid molecule encoding the amino acid sequence of a B7RP-2 polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a B7RP-2 polypeptide will be several hundred nucleotides in length. Nucleic acids larger than about 100 nucleotides can be synthesized as several fragments using these methods. The fragments can then be ligated together to form the full-length nucleotide sequence of a B7RP-2 gene. Usually, the DNA fragment encoding the amino-terminus of the polypeptide will have an ATG, which encodes a methionine residue. This methionine may or may not be present on the mature form of the B7RP-2 polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a B7RP-2 polypeptide in a given host cell. Particular codon alterations will depend upon the B7RP-2 polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "*Celegans*_high.cod," "*Celegans*_low.cod," "*Drosophila*_high.cod," "Human_high.cod," "Maize_high.cod," and "Yeast_high.cod."

In some cases, it may be desirable to prepare nucleic acid molecules encoding B7RP-2 polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of a B7RP-2 polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a B7RP-2 polypeptide may be amplified/expressed in prokaryotic, yeast, insect (baculovirus systems) and/or eukaryotic host cells. Selection of the host cell will depend in part on whether a B7RP-2 polypeptide is to be post-translationally modified (e.g., glycosylated and/or phosphorylated). If so, yeast, insect, or mammalian host cells are preferable. For a review of expression vectors, see *Meth. Enz*., vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the B7RP-2 polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the B7RP-2 polypeptide from the host cell. Affinity purification can be accomplished, for example, by column chromatography using antibodies against the tag as an affinity matrix. Optionally, the tag can subsequently be removed from the purified B7RP-2 polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate B7RP-2 polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the B7RP-2 gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a B7RP-2 polypeptide. If the vector of choice does not contain an origin of replication site, one may be chemically synthesized based on a known sequence, and ligated into the vector. For example, the origin of replication from the plasmid pBR322 (New England Biolabs®, Inc., Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells. Other selection genes may be used to amplify the gene that will be expressed.

Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a B7RP-2 polypeptide. As a result, increased quantities of B7RP-2 polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a B7RP-2 polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a B7RP-2 polypeptide out of the host cell. Typically, a nucleotide sequence encoding the signal sequence is positioned in the coding region of a B7RP-2 nucleic acid molecule, or directly at the 5' end of a B7RP-2 polypeptide coding region. Many signal sequences have been identified, and any of those that are functional in the selected host cell may be used in conjunction with a B7RP-2 nucleic acid molecule. Therefore, a signal sequence may be homologous (naturally occurring) or heterologous to the B7RP-2 nucleic acid molecule. Additionally, a signal sequence may be chemically synthesized using methods described herein. In most cases, the secretion of a B7RP-2 polypeptide from the host cell via the presence of a signal peptide will result in the removal of the signal peptide from the secreted B7RP-2 polypeptide. The signal sequence may be a component of the vector, or it may be a part of a B7RP-2 nucleic acid molecule that is inserted into the vector.

Included within the scope of this invention is the use of either a nucleotide sequence encoding a native B7RP-2 polypeptide signal sequence joined to a B7RP-2 polypeptide coding region or a nucleotide sequence encoding a heterologous signal sequence joined to a B7RP-2 polypeptide coding region. The heterologous signal sequence selected should be one that is recognized and processed, i.e., cleaved by a signal peptidase, by the host cell. For prokaryotic host cells that do not recognize and process the native B7RP-2 polypeptide signal sequence, the signal sequence is substituted by a prokaryotic signal sequence selected, for example, from the group of the alkaline phosphatase, penicillinase, or heat-stable enterotoxin II leaders. For yeast secretion, the native B7RP-2 polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired B7RP-2 polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the B7RP-2 gene especially where the gene used is a full-length genomic sequence or a fragment thereof. Where the intron is not naturally occurring within the gene (as for most cDNAs), the intron may be obtained from another source. The position of the intron with respect to flanking sequences and the B7RP-2 gene is generally important, as the intron must be transcribed to be effective. Thus, when a B7RP-2 cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the B7RP-2 polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding B7RP-2 polypeptide by removing the promoter from the source DNA by restriction enzyme digestion and inserting the desired promoter sequence into the vector. The native B7RP-2 promoter sequence may be used to direct amplification and/or expression of a B7RP-2 nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling B7RP-2 gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.,* 75:3727-31); or the tac promoter (DeBoer et al., 1983, *Proc. Natl. Acad. Sci. U.S.A.,* 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.,* 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-feto-protein gene control region which is active in liver (Krumlauf et al., 1985, *Mol. Cell. Biol.,* 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding a B7RP-2 polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a B7RP-2 nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule encoding a B7RP-2 polypeptide has been inserted into the proper site of the vector, the completed vector may be inserted into a suitable host cell for amplification and/or polypeptide expression. The transformation of an expression vector for a B7RP-2 polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a B7RP-2 polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques,* 14:810-17; Lucklow, 1993, *Curr. Opin. Biotechnol.* 4:564-72; and Lucklow et al., 1993, *J. Virol.,* 67:4566-79. Preferred insect cells are Sf-9 and Hi5 (Invitrogen).

One may also use transgenic animals to express glycosylated B7RP-2 polypeptides. For example, one may use a transgenic milk-producing animal (a cow or goat, for example) and obtain the present glycosylated polypeptide in the animal milk. One may also use plants to produce B7RP-2 polypeptides, however, in general, the glycosylation occurring in plants is different from that produced in mammalian cells, and may result in a glycosylated product which is not suitable for human therapeutic use.

Polypeptide Production

Host cells comprising a B7RP-2 polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a B7RP-2 polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a B7RP-2 polypeptide has been designed to be secreted from the host cells, the majority of polypeptide may be found in the cell culture medium. If however, the B7RP-2 polypeptide is not secreted from the host cells, it will be present in the cytoplasm and/or the nucleus (for eukaryotic host cells) or in the cytosol (for gram-negative bacteria host cells).

For a B7RP-2 polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a B7RP-2 polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized B7RP-2 polypeptide can then be analyzed using gel electrophoresis, immunoprecipitation, or the like. If it is desired to isolate the B7RP-2 polypeptide, isolation may be accomplished using standard methods such as those described herein and in Marston et al., 1990, *Meth. Enz.,* 182:264-75.

In some cases, a B7RP-2 polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-2-mercaptoethanol(bME)/dithio-b(ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a B7RP-2 polypeptide, then the polypeptide will be found primarily in the supernatant after centrifugation of the cell homogenate. The polypeptide may be further isolated from the supernatant using methods such as those described herein.

The purification of a B7RP-2 polypeptide from solution can be accomplished using a variety of techniques. If the polypeptide has been synthesized such that it contains a tag such as Hexahistidine (B7RP-2 polypeptide/hexaHis) or other small peptide such as FLAG (Eastman Kodak Co., New Haven, Conn.) or myc (Invitrogen, Carlsbad, Calif.) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of B7RP-2 polypeptide/polyHis. See, e.g., *Current Protocols in Molecular Biology* § 10.11.8 (Ausubel et al., eds., Green Publishers Inc. and Wiley and Sons 1993).

Additionally, B7RP-2 polypeptides may be purified through the use of a monoclonal antibody that is capable of specifically recognizing and binding to a B7RP-2 polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

B7RP-2 polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized B7RP-2 polypeptides may be oxidized using methods set forth in these references to form disulfide bridges. Chemically synthesized B7RP-2 polypeptides are expected to have comparable biological activity to the corresponding B7RP-2 polypeptides produced recombinantly or purified from natural sources, and thus may be used interchangeably with a recombinant or natural B7RP-2 polypeptide.

Another means of obtaining B7RP-2 polypeptide is via purification from biological samples such as source tissues and/or fluids in which the B7RP-2 polypeptide is naturally found. Such purification can be conducted using methods for protein purification as described herein. The presence of the B7RP-2 polypeptide during purification may be monitored, for example, using an antibody prepared against recombinantly produced B7RP-2 polypeptide or peptide fragments thereof.

A number of additional methods for producing nucleic acids and polypeptides are known in the art, and the methods can be used to produce polypeptides having specificity for B7RP-2 polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive B7RP-2 polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more B7RP-2 polypeptides. Suitable selective binding agents include, but are not limited to, antibodies and derivatives thereof, polypeptides, and small molecules. Suitable selective binding agents may be prepared using methods known in the art. An exemplary B7RP-2 polypeptide selective binding agent of the present invention is capable of binding a certain portion of the B7RP-2 polypeptide thereby inhibiting the binding of the polypeptide to a B7RP-2 polypeptide receptor.

Selective binding agents such as antibodies and antibody fragments that bind B7RP-2 polypeptides are within the scope of the present invention. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the B7RP-2 polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a B7RP-2 polypeptide generally are produced in animals (e.g., rabbits or mice) by means of multiple subcutaneous or intraperitoneal injections of B7RP-2 polypeptide and an adjuvant. It may be useful to conjugate a B7RP-2 polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-B7RP-2 antibody titer.

Monoclonal antibodies directed toward B7RP-2 polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with B7RP-2 polypeptides.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region for the corresponding regions of a human antibody.

Also encompassed by the invention are human antibodies that bind B7RP-2 polypeptides. Using transgenic animals (e.g., mice) that are capable of producing a repertoire of human antibodies in the absence of endogenous immunoglobulin production such antibodies are produced by immunization with a B7RP-2 polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than, e.g., murine) amino acid sequences, including variable regions which are immunospecific for these antigens. See PCT App. Nos. PCT/US96/05928 and PCT/US93/06926. Additional methods are described in U.S. Pat. No. 5,545,807, PCT App. Nos. PCT/US91/245 and PCT/GB89/01207, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-B7RP-2 antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of B7RP-2 polypeptides. The antibodies will bind B7RP-2 polypeptides with an affinity that is appropriate for the assay method being employed.

For diagnostic applications, in certain embodiments, anti-B7RP-2 antibodies may be labeled with a detectable moiety. The detectable moiety can be any one that is capable of producing, either directly or indirectly, a detectable signal. For example, the detectable moiety may be a radioisotope, such as $^{3}H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., a B7RP-2 polypeptide, or an immunologically reactive portion thereof) to compete with the test sample analyte (an B7RP-2 polypeptide) for binding with a limited amount of anti-B7RP-2 antibody. The amount of a B7RP-2 polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-B7RP-2 antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a B7RP-2 polypeptide. In one embodiment, antagonist antibodies of the invention are antibodies or binding fragments thereof which are capable of specifically binding to a B7RP-2 polypeptide and which are capable of inhibiting or eliminating the functional activity of a B7RP-2 polypeptide in vivo or in vitro. In preferred embodiments, the selective binding agent, e.g., an antagonist antibody, will inhibit the functional activity of a B7RP-2 polypeptide by at least about 50%, and preferably by at least about 80%. In another embodiment, the selective binding agent may be an anti-B7RP-2 polypeptide antibody that is capable of interacting with a B7RP-2 polypeptide binding partner (a ligand or receptor) thereby inhibiting or eliminating B7RP-2 polypeptide activity in vitro or in vivo. Selective binding agents, including agonist and antagonist anti-B7RP-2 polypeptide antibodies, are identified by screening assays that are well known in the art.

The invention also relates to a kit comprising B7RP-2 selective binding agents (such as antibodies) and other reagents useful for detecting B7RP-2 polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the B7RP-2 molecules of the invention, including, but not limited to: the identification and validation of B7RP-2 disease-related genes as targets for therapeutics; molecular toxicology of related B7RP-2 molecules and inhibitors thereof; stratification of populations and generation of surrogate markers for clinical trials; and enhancing related B7RP-2 polypeptide small molecule drug discovery by aiding in the identification of selective compounds in high throughput screens.

Chemical Derivatives

Chemically modified derivatives of B7RP-2 polypeptides may be prepared by one skilled in the art, given the disclosures described herein. B7RP-2 polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of any of SEQ ID NO: 2, SEQ ID NO: 4, or SEQ ID NO: 6, or other B7RP-2 polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached B7RP-2 polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of any of SEQ ID NO: 2, SEQ ID NO: 4, or SEQ ID NO: 6, or other B7RP-2 polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the B7RP-2 polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, B7RP-2 polypeptides may be chemically coupled to biotin. The biotin/B7RP-2 polypeptide molecules are then allowed to bind to avidin, resulting in tetravalent avidin/biotin/B7RP-2 polypeptide molecules. B7RP-2 polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present B7RP-2 polypeptide derivatives include those described herein for B7RP-2 polypeptides. However, the B7RP-2 polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native B7RP-2 polypeptide have been disrupted (i.e., "knocked out") such that the level of expression of B7RP-2 polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a B7RP-2 gene for that animal or a heterologous B7RP-2 gene is over-expressed by the animal, thereby creating a "transgenic" animal. Such transgenic animals may be prepared using well known methods such as those described in U.S. Pat. No. 5,489,743 and PCT Pub. No. WO 94/28122.

The present invention further includes non-human animals in which the promoter for one or more of the B7RP-2 polypeptides of the present invention is either activated or inactivated (e.g., by using homologous recombination methods) to alter the level of expression of one or more of the native B7RP-2 polypeptides.

These non-human animals may be used for drug candidate screening. In such screening, the impact of a drug candidate on the animal may be measured. For example, drug candidates may decrease or increase the expression of the B7RP-2 gene. In certain embodiments, the amount of B7RP-2 polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for other Modulators of B7RP-2 Polypeptide Activity

In some situations, it may be desirable to identify molecules that are modulators, i.e., agonists or antagonists, of the activity of B7RP-2 polypeptide. Natural or synthetic molecules that modulate B7RP-2 polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a B7RP-2 polypeptide. Most commonly, a test molecule will interact directly with a B7RP-2 polypeptide. However, it is also contemplated that a test molecule may also modulate B7RP-2 polypeptide activity indirectly, such as by affecting B7RP-2 gene expression, or by binding to a B7RP-2 polypeptide binding partner (e.g., receptor or ligand). In one embodiment, a test molecule will bind to a B7RP-2 polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with B7RP-2 polypeptides are encompassed by the present invention. In certain embodiments, a B7RP-2 polypeptide is incubated with a test molecule under conditions that permit the interaction of the test molecule with a B7RP-2 polypeptide, and the extent of the interaction is measured. The test molecule can be screened in a substantially purified form or in a crude mixture.

In certain embodiments, a B7RP-2 polypeptide agonist or antagonist may be a protein, peptide, carbohydrate, lipid, or small molecular weight molecule that interacts with B7RP-2 polypeptide to regulate its activity. Molecules which regulate B7RP-2 polypeptide expression include nucleic acids which are complementary to nucleic acids encoding a B7RP-2 polypeptide, or are complementary to nucleic acids sequences which direct or control the expression of B7RP-2 polypeptide, and which act as anti-sense regulators of expression.

Once a test molecule has been identified as interacting with a B7RP-2 polypeptide, the molecule may be further evaluated for its ability to increase or decrease B7RP-2 polypeptide activity. The measurement of the interaction of a test molecule with B7RP-2 polypeptide may be carried out in several formats, including cell-based binding assays, membrane binding assays, solution-phase assays, and immunoassays. In general, a test molecule is incubated with a B7RP-2 polypeptide for a specified period of time, and B7RP-2 polypeptide activity is determined by one or more assays for measuring biological activity.

The interaction of test molecules with B7RP-2 polypeptides may also be assayed directly using polyclonal or monoclonal antibodies in an immunoassay. Alternatively, modified forms of B7RP-2 polypeptides containing epitope tags as described herein may be used in solution and immunoassays.

In the event that B7RP-2 polypeptides display biological activity through an interaction with a binding partner (e.g., a receptor or a ligand), a variety of in vitro assays may be used to measure the binding of a B7RP-2 polypeptide to the corresponding binding partner (such as a selective binding agent, receptor, or ligand). These assays may be used to screen test molecules for their ability to increase or decrease the rate and/or the extent of binding of a B7RP-2 polypeptide to its binding partner. In one assay, a B7RP-2 polypeptide is immobilized in the wells of a microtiter plate. Radiolabeled B7RP-2 polypeptide binding partner (for example, iodinated B7RP-2 polypeptide binding partner) and a test molecule can then be added either one at a time (in either order) or simultaneously to the wells. After incubation, the wells can be washed and counted for radioactivity, using a scintillation counter, to determine the extent to which the binding partner bound to the B7RP-2 polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing B7RP-2 polypeptide binding partner to the microtiter plate wells, incubating with the test molecule and radiolabeled B7RP-2 polypeptide, and determining the extent of B7RP-2 polypeptide binding. See, e.g., *Current Protocols in Molecular Biology*, chap. 18 (Ausubel et al., eds., Green Publishers Inc. and Wiley and Sons 1995).

As an alternative to radiolabeling, a B7RP-2 polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a B7RP-2 polypeptide or to a B7RP-2 polypeptide binding partner, and which is conjugated to biotin, may also be used for purposes of detection following incubation of the complex with enzyme-linked streptavidin linked to AP or HRP.

A B7RP-2 polypeptide or a B7RP-2 polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a B7RP-2 polypeptide and its binding partner can be assessed using the methods described herein. Alternatively, the substrate-protein complex can be immobilized in a column with the test molecule and complementary protein passing through the column. The formation of a complex between a B7RP-2 polypeptide and its binding partner can then be assessed using any of the techniques described herein (e.g., radiolabelling or antibody binding).

Another in vitro assay that is useful for identifying a test molecule which increases or decreases the formation of a complex between a B7RP-2 polypeptide binding protein and a B7RP-2 polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either B7RP-2 polypeptide or a B7RP-2 polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a B7RP-2 polypeptide and a B7RP-2 polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a B7RP-2 polypeptide and B7RP-2 polypeptide binding partner. The assays may be automated to screen compounds generated in phage display, synthetic peptide, and chemical synthesis libraries.

Compounds which increase or decrease the formation of a complex between a B7RP-2 polypeptide and a B7RP-2 polypeptide binding partner may also be screened in cell culture using cells and cell lines expressing either B7RP-2 polypeptide or B7RP-2 polypeptide binding partner. Cells and cell lines may be obtained from any mammal, but preferably will be from human or other primate, canine, or rodent sources. The binding of a B7RP-2 polypeptide to cells expressing B7RP-2 polypeptide binding partner at the surface is evaluated in the presence or absence of test molecules, and the extent of binding may be determined by, for example, flow cytometry using a biotinylated antibody to a B7RP-2 polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the B7RP-2 gene. In certain embodiments, the amount of B7RP-2 polypeptide or a B7RP-2 polypeptide fragment that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. USA.* 91:664-68. For example, an 11 amino acid sequence (Y-G-R-K-K-R-R-Q-R-R-R; SEQ ID NO: 14) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 15), which penetrate tissues following intraperitoneal administration, are prepared, and the binding of such constructs to cells is detected by fluorescence-activated cell sorting (FACS) analysis. Cells treated with a tat-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a B7RP-2 antagonist (such as an anti-B7RP-2 selective binding agent, small molecule, soluble receptor, or antisense oligonucleotide) can be administered intracellularly to inhibit the activity of a B7RP-2 molecule. As used herein, the term "B7RP-2 molecule" refers to both B7RP-2 nucleic acid molecules and B7RP-2 polypeptides as defined herein. Where desired, the B7RP-2 protein itself may also be internally administered to a cell using these procedures. See also, Straus, 1999, *Science* 285:1466-67.

Cell Source Identification Using B7RP-2 Polypeptide

In accordance with certain embodiments of the invention, it may be useful to be able to determine the source of a certain cell type associated with a B7RP-2 polypeptide. For example, it may be useful to determine the origin of a disease or pathological condition as an aid in selecting an appropriate therapy. In certain embodiments, nucleic acids encoding a B7RP-2 polypeptide can be used as a probe to identify cells described herein by screening the nucleic acids of the cells with such a probe. In other embodiments, one may use anti-B7RP-2 polypeptide antibodies to test for the presence of B7RP-2 polypeptide in cells, and thus, determine if such cells are of the types described herein.

B7RP-2 Polypeptide Compositions and Administration

Therapeutic compositions are within the scope of the present invention. Such B7RP-2 polypeptide pharmaceutical compositions may comprise a therapeutically effective amount of a B7RP-2 polypeptide or a B7RP-2 nucleic acid molecule in admixture with a pharmaceutically or physiologically acceptable formulation agent selected for suitability with the mode of administration. Pharmaceutical compositions may comprise a therapeutically effective amount of one or more B7RP-2 polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, B7RP-2orhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. *See Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the B7RP-2 molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, B7RP-2 polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the B7RP-2 polypeptide product may be formulated as a lyophilizate using appropriate excipients such as sucrose.

The B7RP-2 polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired B7RP-2 molecule in a pharmaceutically acceptable vehicle. A particularly suitable vehicle for parenteral injection is sterile distilled water in which a B7RP-2 molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, B7RP-2 polypeptide may be formulated as a dry powder for inhalation. B7RP-2 polypeptide or nucleic acid molecule inhalation solutions may also be formulated with a propellant for aerosol delivery. In yet another embodiment, solutions may be nebulized. Pulmonary administration is further described in PCT Pub. No. WO 94/20069, which describes the pulmonary delivery of chemically modified proteins.

It is also contemplated that certain formulations may be administered orally. In one embodiment of the present invention, B7RP-2 polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the B7RP-2 polypeptide. Diluents, flavorings, low melting point waxes, vegetable oils, lubricants, suspending agents, tablet disintegrating agents, and binders may also be employed.

Another pharmaceutical composition may involve an effective quantity of B7RP-2 polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional B7RP-2 polypeptide pharmaceutical compositions will be evident to those skilled in the art, including formulations involving B7RP-2 polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The B7RP-2 pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a B7RP-2 pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the B7RP-2 molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 μg/kg to up to about 100 mg/kg or more, depending on the factors mentioned above. In other embodiments, the dosage may range from 0.1 μg/kg up to about 100 mg/kg; or 1 μg/kg up to about 100 mg/kg; or 5 μg/kg up to about 100 mg/kg.

The frequency of dosing will depend upon the pharmacokinetic parameters of the B7RP-2 molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intra-parenchymal), intracerebroventricular, intramuscular, intraocular, intraarterial, intraportal, or intralesional routes;

by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use B7RP-2 polypeptide pharmaceutical compositions in an ex vivo manner. In such instances, cells, tissues, or organs that have been removed from the patient are exposed to B7RP-2 polypeptide pharmaceutical compositions after which the cells, tissues, or organs are subsequently implanted back into the patient.

In other cases, a B7RP-2 polypeptide can be delivered by implanting certain cells that have been genetically engineered, using methods such as those described herein, to express and secrete the B7RP-2 polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more B7RP-2 polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent B7RP-2 gene, or an under-expressed gene, and thereby produce a cell which expresses therapeutically efficacious amounts of B7RP-2 polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; PCT/US90/07642, and PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a B7RP-2 polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired B7RP-2 polypeptide. The control element controls a portion of the DNA present in the host cell genome. Thus, the expression of the desired B7RP-2 polypeptide may be achieved not by transfection of DNA that encodes the B7RP-2 gene itself, but rather by the use of targeting DNA (containing regions of homology with the endogenous gene of interest) coupled with DNA regulatory segments that provide the endogenous gene sequence with recognizable signals for transcription of a B7RP-2 gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, B7RP-2 polypeptide production from a cell's endogenous B7RP-2 gene involves first using homologous recombination to place a recombination sequence from a site-specific recombination system (e.g., Cre/loxP, FLP/FRT) (Sauer, 1994, *Curr. Opin. Biotechnol.,* 5:521-27; Sauer, 1993, *Methods Enzymol.,* 225:890-900) upstream of (i.e., 5' to) the cell's endogenous genomic B7RP-2 polypeptide coding region. A plasmid containing a recombination site homologous to the site that was placed just upstream of the genomic B7RP-2 polypeptide coding region is introduced into the modified cell line along with the appropriate recombinase enzyme. This recombinase causes the plasmid to integrate, via the plasmid's recombination site, into the recombination site located just upstream of the genomic B7RP-2 polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased B7RP-2 polypeptide production from the cell's endogenous B7RP-2 gene.

A further method to use the cell line in which the site specific recombination sequence had been placed just upstream of the cell's endogenous genomic B7RP-2 polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.,* 5:521-27; Sauer, 1993, *Methods Enzymol.,* 225:890-900) that would create a new or modified transcriptional unit resulting in de novo or increased B7RP-2 polypeptide production from the cell's endogenous B7RP-2 gene.

An additional approach for increasing, or causing, the expression of B7RP-2 polypeptide from a cell's endogenous B7RP-2 gene involves increasing, or causing, the expression of a gene or genes (e.g., transcription factors) and/or decreasing the expression of a gene or genes (e.g., transcriptional repressors) in a manner which results in de novo or increased B7RP-2 polypeptide production from the cell's endogenous B7RP-2 gene. This method includes the introduction of a non-naturally occurring polypeptide (e.g., a polypeptide comprising a site specific DNA binding domain fused to a transcriptional factor domain) into the cell such that de novo or increased B7RP-2 polypeptide production from the cell's endogenous B7RP-2 gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of B7RP-2 polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a B7RP-2 polypeptide, which nucleotides may be used as targeting sequences.

B7RP-2 polypeptide cell therapy, e.g., the implantation of cells producing B7RP-2 polypeptides, is also contemplated. This embodiment involves implanting cells capable of synthesizing and secreting a biologically active form of B7RP-2 polypeptide. Such B7RP-2 polypeptide-producing cells can be cells that are natural producers of B7RP-2 polypeptides or may be recombinant cells whose ability to produce B7RP-2 polypeptides has been augmented by transformation with a gene encoding the desired B7RP-2 polypeptide or with a gene augmenting the expression of B7RP-2 polypeptide. Such a modification may be accomplished by means of a vector suitable for delivering the gene as well as promoting its expression and secretion. In order to minimize a potential immunological reaction in patients being administered a B7RP-2 polypeptide, as may occur with the administration of a polypeptide of a foreign species, it is preferred that the natural cells producing B7RP-2 polypeptide be of human origin and produce human B7RP-2 polypeptide. Likewise, it is preferred that the recombinant cells producing B7RP-2 polypeptide be transformed with an expression vector containing a gene encoding a human B7RP-2 polypeptide.

Implanted cells may be encapsulated to avoid the infiltration of surrounding tissue. Human or non-human animal cells may be implanted in patients in biocompatible, semipermeable polymeric enclosures or membranes that allow the release of B7RP-2 polypeptide, but that prevent the destruction of the cells by the patient's immune system or by other detrimental factors from the surrounding tissue. Alternatively, the patient's own cells, transformed to produce B7RP-2 polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of B7RP-2 polypeptides is also envisioned. One example of a gene therapy technique is to use the B7RP-2 gene (either genomic DNA, cDNA, and/or synthetic DNA) encoding a B7RP-2 polypeptide which may be operably linked to a constitutive or inducible promoter to form a "gene therapy DNA construct." The promoter may be homologous or heterologous to the endogenous B7RP-2 gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the B7RP-2 gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and PCT Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and PCT Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding B7RP-2 polypeptide into cells via local injection of a B7RP-2 nucleic acid molecule or by other appropriate viral or non-viral delivery vectors. Hefti 1994, *Neurobiology* 25:1418-35. For example, a nucleic acid molecule encoding a B7RP-2 polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding a B7RP-2 polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that B7RP-2 gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous B7RP-2 polypeptide expression in a cell via gene therapy is to insert one or more enhancer elements into the B7RP-2 polypeptide promoter, where the enhancer elements can serve to increase transcriptional activity of the B7RP-2 gene. The enhancer elements used will be selected based on the tissue in which one desires to activate the gene—enhancer elements known to confer promoter activation in that tissue will be selected. For example, if a gene encoding a B7RP-2 polypeptide is to be "turned on" in T-cells, the lck promoter enhancer element may be used. Here, the functional portion of the transcriptional element to be added may be inserted into a fragment of DNA containing the B7RP-2 polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease B7RP-2 polypeptide expression by modifying the nucleotide sequence of the endogenous promoter. Such modification is typically accomplished via homologous recombination methods. For example, a DNA molecule containing all or a portion of the promoter of the B7RP-2 gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding B7RP-2 gene. The deletion of the TATA box or the transcription activator binding site in the promoter may be accomplished by generating a DNA construct comprising all or the relevant portion of the B7RP-2 polypeptide promoter (from the same or a related species as the B7RP-2 gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

B7RP-2 nucleic acid molecules, polypeptides, and agonists and antagonists thereof can be used to treat, diagnose, ameliorate, or prevent a number of diseases, disorders, or conditions, including those recited herein.

B7RP-2 polypeptide agonists and antagonists include those molecules which regulate B7RP-2 polypeptide activity and either increase or decrease at least one activity of the mature form of the B7RP-2 polypeptide. Agonists or antagonists may be co-factors, such as a protein, peptide, carbohydrate, lipid, or small molecular weight molecule, which interact with B7RP-2 polypeptide and thereby regulate its activity. Potential polypeptide agonists or antagonists include antibodies that react with either soluble or membrane-bound forms of B7RP-2 polypeptides that comprise part or all of the extracellular domains of the said proteins. Molecules that regulate B7RP-2 polypeptide expression typically include nucleic acids encoding B7RP-2 polypeptide that can act as anti-sense regulators of expression.

Bone tissue consists of a matrix of collagenous and non-collagenous proteins, minerals (largely calcium and phosphorous), and cells. Three types of cells are involved in the dynamic process by which bone is continually formed and resorbed: osteocytes, osteoblasts, and osteoclasts. Osteoblasts promote formation of bone tissue whereas osteoclasts are associated with resorption. Resorption, or the dissolution of bone matrix and mineral, is a fast and efficient process compared to bone formation and can release large amounts of mineral from bone. Osteoclasts are involved in the regulation of the normal remodeling of skeletal tissue and in resorption induced by hormones. For instance, resorption is stimulated by the secretion of parathyroid hormone in response to decreasing concentrations of calcium ion in extracellular fluids. In contrast, inhibition of resorption is the principal function of calcitonin. In addition, metabolites of vitamin D alter the responsiveness of bone to parathyroid hormone and calcitonin.

Following skeletal maturity, the amount of bone in the skeleton reflects the balance (or imbalance) of bone formation and bone resorption. Peak bone mass occurs after skeletal maturity prior to the fourth decade. Between the fourth and fifth decades, the equilibrium shifts and bone resorption dominates. The inevitable decrease in bone mass with advancing years starts earlier in females than males and is distinctly accelerated after menopause in some females (principally those of Caucasian and Asian descent).

Osteopenia is a condition relating generally to any decrease in bone mass to below normal levels. Such a condition may arise from a decrease in the rate of bone synthesis or an increase in the rate of bone destruction or both. The most common form of osteopenia is primary osteoporosis, also referred to as postmenopausal and senile osteoporosis. This form of osteoporosis is a consequence of the universal loss of bone with age and is usually a result of increase in bone resorption with a normal rate of bone formation. About 25 to 30 percent of all white females in the United States develop symptomatic osteoporosis. A direct relationship exists between osteoporosis and the incidence of hip, femoral, neck, and inter-trochanteric fracture in women 45 years and older. Elderly males develop symptomatic osteoporosis between the ages of 50 and 70, but the disease primarily affects females.

The cause of postmenopausal and senile osteoporosis is unknown. Several factors have been identified which may contribute to the condition. They include alteration in hormone levels accompanying aging, and inadequate calcium consumption attributed to decreased intestinal absorption of calcium and other minerals. Treatments have usually included hormone therapy or dietary supplements in an attempt to retard the process. To date, however, an effective treatment for bone loss does not exist.

The B7RP-2 nucleic acid molecules, polypeptides, and agonists and antagonists of the present invention may be used to treat, diagnose, ameliorate, or prevent diseases and disorders of the bones, such as diseases or disorders characterized by a net bone loss (such as osteopenia or osteolysis). For example, B7RP-2 polypeptides may be used to suppress the rate of bone resorption. In this manner, an individual may be treated with B7RP-2 polypeptides in order to reduce the rate of bone resorption where the resorption rate is above normal or to reduce bone resorption to below normal levels in order to compensate for below normal levels of bone formation.

Conditions which may be treatable with the B7RP-2 nucleic acid molecules, polypeptides, and agonists and antagonists of the present invention include the following: osteoporosis, such as primary osteoporosis, endocrine osteoporosis (hyperthyroidism, hyperparathryoidism, Cushing's syndrome, and acromegaly), hereditary and congenital forms of osteoporosis (osteogenesis imperfecta, homocystinuria, Menkes' syndrome, and Riley-Day syndrome), and osteoporosis due to immobilization of extremities; Paget's disease of bone (osteitis deformans) in adults and juveniles; osteomyelitis, or an infectious lesion in bone, leading to bone loss; hypercalcemia resulting from solid tumors (breast, lung, and kidney) and hematologic malignacies (multiple myeloma, lymphoma, and leukemia), idiopathic hypercalcemia, and hypercalcemia associated with hyperthryoidism and renal function disorders; osteopenia following surgery, induced by steroid administration, and associated with disorders of the small and large intestine and with chronic hepatic and renal diseases; osteonecrosis, or bone cell death, associated with traumatic injury or nontraumatic necrosis associated with Gaucher's disease, sickle cell anemia, systemic lupus erythematosus, rheumatoid arthritis, periodontal disease, osteolytic metastasis, and other conditions. Other bone diseases and disorders are encompassed within the scope of the invention.

The B7RP-2 nucleic acid molecules, polypeptides, and agonists and antagonists of the present invention may be used to treat, diagnose, ameliorate, or prevent diseases associated with T-cell function (e.g., functioning as a T-cell receptor decoy). For example, antibodies, soluble proteins comprising extracellular domains, or other regulators of B7RP-2 polypeptide that result in prolonged or enhanced T-cell activation can be used to increase the immune response to tumors.

The B7RP-2 nucleic acid molecules, polypeptides, and agonists and antagonists of the present invention may be used in the treatment of autoimmune disease, graft survival, immune cell activation for inhibiting tumor cell growth, T-cell dependent B-cell mediated diseases, and cancer gene immunotherapy. In one embodiment, agonists or antagonists of B7RP-2 polypeptide function, soluble B7RP-2 polypeptides, or B7RP-2 polypeptide derivatives may be beneficial to alleviate symptoms in diseases with chronic immune cell dysfunction. Autoimmune diseases, such as systemic lupus erythematosis, rheumatoid arthritis, osteoarthritis, immune thrombocytopenic purpura (ITP), and psoriasis, may be treated with agonists or antagonists of B7RP-2 polypeptide function, soluble B7RP-2 polypeptides, or B7RP-2 polypeptide derivatives. In addition, chronic inflammatory diseases, such as inflammatory bowel disease (Crohn's disease and ulcerative colitis), Grave's disease, Hashimoto's thyroiditis, and diabetes mellitis, may also be treated with agonists or antagonists of B7RP-2 polypeptide function, soluble B7RP-2 polypeptides, or B7RP-2 polypeptide derivatives.

Agonists or antagonists of B7RP-2 polypeptide function, soluble B7RP-2 polypeptides, or B7RP-2 polypeptide derivatives may be used as immunosuppressive agents for bone marrow and organ transplantation and may be used to prolong graft survival. Such agonists or antagonists of B7RP-2 polypeptide function, soluble B7RP-2 polypeptides, or B7RP-2 polypeptide derivatives may provide significant advantages over existing treatments. Bone marrow and organ transplantation therapy must contend with T-cell mediated rejection of the foreign cells or tissue by the host. Present therapeutic regimens for inhibiting T-cell mediated rejection involve treatment with the drugs cyclosporine or FK506. While drugs are effective, patients suffer from serious side effects, including hepatotoxicity, nephrotoxicity, and neurotoxicity. The target for the cyclosporin/FK506 class of therapeutics is calcineurin, a phosphatase with ubiquitous expression. Agonists or antagonists of B7RP-2 polypeptide function, soluble B7RP-2 polypeptides, or B7RP-2 polypeptide derivatives may lack the severe side effects observed with the use of the present immunotherapeutic agents. Agonists or antagonists of B7RP-2 polypeptide function, soluble B7RP-2 polypeptides, or B7RP-2 polypeptide derivatives may be used as immunosuppressive agents for autoimmune disorders, such as rheumatoid arthritis, osteoarthritis psoriasis, multiple sclerosis, diabetes, and systemic lupus erythematosus. Agonists or antagonists of B7RP-2 polypeptide function, soluble B7RP-2 polypeptides, or B7RP-2 polypeptide derivatives may also be used to alleviate toxic shock syndrome, inflammatory bowel disease, allosensitization due to blood transfusions, T-cell dependent B-cell mediated diseases, and the treatment of graft versus host disease.

Gene therapy using B7RP-2 genes of the invention may be used in cancer immunotherapy. B7RP-2 genes introduced into cancer cells can transform them into antigen presenting cells that can be recognized by the T-cells of the immune system when introduced back into an animal. Recognition of the transfected tumor cells by the T-cells results in the eradication of tumors expressing and tumors not expressing the B7RP-2 gene. This immunotherapy approach may be used for various leukemias, sarcomas, melanomas, adenocarcinomas, breast carcinomas, prostate tumors, lung carcinomas, colon carcinomas, and other tumors. This invention encompasses using the B7RP-2 gene in a similar manner to enhance T-cell activation in response to variety of tumors.

For instance, many vaccines act by eliciting an effective and specific antibody response. Some vaccines, especially those against intestinal microorganisms (e.g., Hepatitis A virus and *Salmonella*), elicit a short-lived antibody response. It is desirable to potentiate and prolong this response in order to increase the effectiveness of the vaccine. Therefore, soluble B7RP-2 polypeptides may serve as vaccine adjuvants.

Conversely, since B7RP-2 may have negative immune regulatory functions, inhibition of B7RP-2 activity using antibodies, small molecules, peptibodies, or other antagonists of B7RP-2 function may result in immune enhancement and anti-tumor activity.

Anti-viral responses may also be enhanced by activators or agonists of the B7RP-2 polypeptide pathway. The enhancement of cellular immune functions by B7RP-2 polypeptide antagonists may also be beneficial in eliminating virus-infected cells. In a complementary fashion, B7RP-2 polypeptide antagonists may also have effects on humoral immune functions that may enhance antibody mediated responses and that may function to help clear free virus from the body.

Conversely, there are a number of clinical conditions that would be ameliorated by the inhibition of antibody production. Hypersensitivity is a normally beneficial immune response that is exaggerated or inappropriate, and leads to inflammatory reactions and tissue damage. Hypersensitivity reactions that are antibody-mediated may be particularly susceptible to antagonism by agonists of B7RP-2 polypeptide function, soluble B7RP-2 polypeptides, or B7RP-2 polypeptide derivatives. Allergies, hay fever, asthma, and acute edema cause type I hypersensitivity reactions, and these reactions may be suppressed by agonists of B7RP-2 polypeptide function, soluble B7RP-2 polypeptides, or B7RP-2 polypeptide derivatives.

Diseases that cause antibody-mediated hypersensitivity reactions, including systemic lupus erythematosis, arthritis (rheumatoid arthritis, reactive arthritis, and psoriatic arthritis), nephropathies (glomerulo-nephritis, membranous, mesangiocapillary, focal segmental, focal necrotizing, crescentic, and proliferative tubulopathies), skin disorders (pemphigus, pemphigoid, and erythema nodosum), endocrinopathies (thyroiditis, Grave's, Hashimoto's, insulin-dependent diabetes mellitus), various pneumopathies (especially extrinsic alveolitis), various vasculopathies, coeliac disease, with aberrant production of IgA, many anemias and thrombocytopenias, Guillain-Barre Syndrome, and myasthenia gravis, may be treated with agonists of B7RP-2 polypeptide function, soluble B7RP-2 polypeptides, or B7RP-2 polypeptide derivatives.

In addition, lymphoproliferative disorders, such as multiple myeloma, Waldenstrom's macroglobulinemia, and crioglobulinemias, may be inhibited by agonists of B7RP-2 polypeptide function, soluble B7RP-2 polypeptides, or B7RP-2 polypeptide derivatives. Finally, graft versus host disease, an "artificial" immune disorder, may benefit from the inhibition of antibody production by agonists of B7RP-2 polypeptide function, soluble B7RP-2 polypeptides, or B7RP-2 polypeptide derivatives.

Agonists or antagonists of B7RP-2 polypeptide function may be used (simultaneously or sequentially) in combination with one or more cytokines, growth factors, antibiotics, anti-inflammatories, and/or chemotherapeutic agents as is appropriate for the condition being treated.

Other diseases caused by or mediated by undesirable levels of B7RP-2 polypeptides are encompassed within the scope of the invention. Undesirable levels include excessive levels of B7RP-2 polypeptides and sub-normal levels of B7RP-2 polypeptides.

Uses of B7RP-2 Nucleic Acids and Polypeptides

Nucleic acid molecules of the invention (including those that do not themselves encode biologically active polypeptides) may be used to map the locations of the B7RP-2 gene and related genes on chromosomes. Mapping may be done by techniques known in the art, such as PCR amplification and in situ hybridization.

B7RP-2 nucleic acid molecules (including those that do not themselves encode biologically active polypeptides), may be useful as hybridization probes in diagnostic assays to test, either qualitatively or quantitatively, for the presence of a B7RP-2 nucleic acid molecule in mammalian tissue or bodily fluid samples.

Other methods may also be employed where it is desirable to inhibit the activity of one or more B7RP-2 polypeptides. Such inhibition may be effected by nucleic acid molecules that are complementary to and hybridize to expression control sequences (triple helix formation) or to B7RP-2 mRNA. For example, antisense DNA or RNA molecules, which have a sequence that is complementary to at least a portion of a B7RP-2 gene can be introduced into the cell. Anti-sense probes may be designed by available techniques using the sequence of the B7RP-2 gene disclosed herein. Typically, each such antisense molecule will be complementary to the start site (5' end) of each selected B7RP-2 gene. When the antisense molecule then hybridizes to the corresponding B7RP-2 mRNA, translation of this mRNA is prevented or reduced. Anti-sense inhibitors provide information relating to the decrease or absence of a B7RP-2 polypeptide in a cell or organism.

Alternatively, gene therapy may be employed to create a dominant-negative inhibitor of one or more B7RP-2 polypeptides. In this situation, the DNA encoding a mutant polypeptide of each selected B7RP-2 polypeptide can be prepared and introduced into the cells of a patient using either viral or non-viral methods as described herein. Each such mutant is typically designed to compete with endogenous polypeptide in its biological role.

In addition, a B7RP-2 polypeptide, whether biologically active or not, may be used as an immunogen, that is, the polypeptide contains at least one epitope to which antibodies may be raised. Selective binding agents that bind to a B7RP-2 polypeptide (as described herein) may be used for in vivo and in vitro diagnostic purposes, including, but not limited to, use in labeled form to detect the presence of B7RP-2 polypeptide in a body fluid or cell sample. The antibodies may also be used to prevent, treat, or diagnose a number of diseases and disorders, including those recited herein. The antibodies may bind to a B7RP-2 polypeptide so as to diminish or block at least one activity characteristic of a B7RP-2 polypeptide, or may bind to a polypeptide to increase at least one activity characteristic of a B7RP-2 polypeptide (including by increasing the pharmacokinetics of the B7RP-2 polypeptide).

The B7RP-2 polypeptides of the present invention can be used to clone B7RP-2 polypeptide receptors, using an expression cloning strategy. Radiolabeled ($^{125}$Iodine) B7RP-2 polypeptide or affinity/activity-tagged B7RP-2 polypeptide (such as an Fc fusion or an alkaline phosphatase fusion) can be used in binding assays to identify a cell type or cell line or tissue that expresses B7RP-2 polypeptide receptors. RNA isolated from such cells or tissues can be converted to cDNA, cloned into a mammalian expression vector, and transfected into mammalian cells (such as COS or 293 cells) to create an expression library. A radiolabeled or tagged B7RP-2 polypeptide can then be used as an affinity ligand to identify and isolate from this library the subset of cells that express the B7RP-2 polypeptide receptors on their surface. DNA can then be isolated from these cells and transfected into mammalian cells to create a secondary expression library in which the fraction of cells expressing B7RP-2 polypeptide receptors is many-fold higher than in the original library. This enrichment process can be repeated iteratively until a single recombinant clone containing a B7RP-2 polypeptide receptor is isolated. Isolation of the B7RP-2 polypeptide receptors is useful for identifying or developing novel agonists and antagonists of the B7RP-2 polypeptide signaling pathway. Such agonists and antagonists include soluble B7RP-2 polypeptide receptors, anti-B7RP-2 polypeptide receptor antibodies, small molecules, or antisense oligonucleotides, and they may be used for treating, preventing, or diagnosing one or more of the diseases or disorders described herein.

The murine and human B7RP-2 nucleic acids of the present invention are also useful tools for isolating the corresponding chromosomal B7RP-2 polypeptide genes. For example, mouse chromosomal DNA containing B7RP-2 sequences can be used to construct knockout mice, thereby permitting an examination of the in vivo role for B7RP-2 polypeptide. The human B7RP-2 genomic DNA can be used to identify heritable tissue-degenerating diseases.

The following examples are intended for illustration purposes only, and should not be construed as limiting the scope of the invention in any way.

EXAMPLE 1

Cloning of the Human B7RP-2 Polypeptide Gene

Generally, materials and methods as described in Sambrook et al. supra were used to clone and analyze the gene encoding human B7RP-2 polypeptide.

A search of a proprietary database was performed using the rat B7RP-2 ortholog (SEQ ID NO: 5) as the query sequence. A 342 bp clone was identifying as containing nucleic acid sequences encoding a portion of human B7RP-2 polypeptide. This sequence was expanded to 792 bp (SEQ ID NO: 16) by examination of related contigs.

Due to the high level of B7RP-2 expression detected in bone calveria by in situ hybridization, cDNA sequences encoding human B7RP-2 polypeptide were isolated in amplification reactions performed using a human bone calveria cDNA library and the amplimers 2245-71 (5'-C-A-A-C-G-A-G-C-A-G-G-G-C-T-T-G-T-T-T-G-3'; SEQ ID NO: 17) and 2245-72 (5'-G-G-T-C-T-G-T-G-T-A-T-C-G-C-A-T-C-C-T-T-T-G-G-3'; SEQ ID NO: 18). A PCR product of the expected size was isolated and subcloned into the TOPO® II vector. The resulting ligation reactions were used to transform competent bacteria and the clones obtained in this manner were then analyzed by sequencing.

Both 5'RACE and 3'RACE reactions were performed in order to generate the full-length cDNA sequence for human B7RP-2 polypeptide. To isolate cDNA sequences corresponding to the 3' end of the cDNA sequence, 3'RACE was performed using a human fetal calveria cDNA library in the pSPORT1 vector and the primers 2245-72 and 1071-80 (5'-T-G-C-A-G-G-T-A-C-C-G-G-T-C-C-G-G-A-A-T-3'; SEQ ID NO: 19). Nested PCR was performed using a portion of the 3'RACE amplification product and the primers 2279-24 (5'-T-G-T-C-A-G-A-G-C-A-G-G-A-T-G-C-A-T-C-T-G-T-3'; SEQ ID NO: 20) and 1071-80. A PCR product of 800 bp was isolated and subcloned into the TOPO® II vector. The resulting ligation reactions were used to transform competent bacteria and the clones obtained in this manner were then analyzed by sequencing.

To isolate cDNA sequences corresponding to the 5' end of the cDNA sequence, 5'RACE was performed using the human fetal calveria cDNA library described above and the primers 2279-22 (5'-T-G-C-A-T-T-G-C-C-T-T-G-T-G-C-C-A-G-C-A-G-G-T-3'; SEQ ID NO: 21) and 1071-80. Nested PCR was performed using a portion of the 5'RACE amplification product and the primers 2279-21 (5'-C-T-G-T-C-A-G-C-T-G-C-C-A-G-A-T-G-A-G-G-T-T-G-3'; SEQ ID NO: 22) and 1071-80. A PCR product of 400 bp was isolated and subcloned into the TOPO® II vector. The resulting ligation reactions were used to transform competent bacteria and the clones obtained in this manner were then analyzed by sequencing.

To isolate the full-length cDNA sequence encoding B7RP-2 polypeptide, amplification reactions were performed using the human fetal calveria cDNA library described above and the primers 2318-34 (5'-G-C-G-T-C-C-C-T-G-A-G-T-C-C-C-A-G-A-G-3'; SEQ ID NO: 23) and 2318-35 (5'-G-T-G-T-A-T-C-G-C-A-T-C-C-T-T-T-G-G-A-G-A-A-G-3'; SEQ ID NO: 24). A PCR product of approximately 1.6 kb was isolated and subcloned into the TOPO® II vector. The resulting ligation reactions were used to transform competent bacteria and the clones obtained in this manner were then analyzed by sequencing. Sequence analysis indicated that the human B7RP-2 gene comprises a 948 bp open reading frame encoding a protein of 316 amino acids (FIGS. 1A-1B).

Isolation of the cDNA sequences encoding murine and rat B7RP-2 polypeptide, indicate that both the murine B7RP-2 gene (FIGS. 2A-2B) and the rat B7RP-2 gene (FIGS. 3A-3C) also comprise open reading frames of 948 bp, each encoding a protein of 316 amino acids. The amino acid sequences for human B7RP-2 polypeptide (SEQ ID NO: 2), murine B7RP-2 polypeptide (SEQ ID NO: 4), and rat B7RP-2 polypeptide (SEQ ID NO: 6) were aligned using the ClustalW algorithm (Thompson et al., 1994, *Nucleic Acids Res.* 22:4673-80). The ClustalW alignment of the human, murine, and rat B7RP-2 orthologs (FIGS. 4A-4B) suggests that human B7RP-2 polypeptide will tolerate nonconservative amino acid substitutions at a number of positions (see SEQ ID NO: 32), and further, that conservative amino acid substitutions may be made at several other positions in the human B7RP-2 amino acid sequence (e.g., at positions 20, 29, 101, 120, 184, 260, 261, 291, and 306). A BLAST analysis of the human, murine, and rat B7RP-2 orthologs against the Conserved Domain Database (a collection of functional and structural domains derived primarily from the Smart and Pfam databases) indicated that the three proteins also share at least two conserved protein domains, namely an immunoglobulin V-type domain and an immunoglobulin C-type or C-2 type domain (FIG. 5).

Sequence analysis also revealed that B7RP-2 polypeptide shares homology with the B7 family of proteins. FIGS. 6A-6B illustrate the amino acid sequence alignment of human butyrophilin, subfamily 1, member A1 (hu_BTN1A1; SEQ ID NO: 7), bovine butyrophilin precursor (bo_BTN; SEQ ID NO: 8), murine butyrophilin (mu_BTN; SEQ ID NO: 9), human butyrophilin, subfamily 2, member A1 (hu_BTN2A1; SEQ ID NO: 10), human butyrophilin-like protein (hu_BT3.2; SEQ ID NO: 11), human butyrophilin, subfamily 3, member A2 (hu_BTN3A2; SEQ ID NO: 12), *Grus americana* B-G-like protein (gr_BG2; SEQ ID NO: 13), and human B7RP-2 polypeptide (hu_B7RP-2; SEQ ID NO: 2).

The predicted protein product of the B7RP-2 gene is related to the B7 family of proteins. These proteins are members of the immunoglobulin superfamily and function as regulators of the T-cell mediated immune response. Members of the B7 family of proteins are Type-1 membrane proteins with a small cytoplasmic domain and extracellular regions that contain immunoglobulin V (variable) and C (constant) domains. The known members of the B7 family include CD80 (B7-1), CD86 (B7-2), B7RP-1, and B7-H1. B7-1 and B7-2 interact with CD28 and CTLA-4 and are mediators of the T-cell costimulatory pathway. B7RP-1 binds to a distinct receptor (ICOS; inducible co-stimulator) and is also a stimulator of T-cell proliferation. B7-H1 also co-stimulates T-cell proliferation, but does not bind CD28, CTLA-4, or ICOS. The protein sequences of this family are poorly conserved and consequently, are difficult to distinguish from other related molecules using computational methods, especially when only a portion of the full-length coding region sequence is compared. Other proteins exhibiting sequence homology to the B7 family include the butyrophilins and PRO352. Still more distantly related are the myelin oligodendrocyte proteins (MOGs).

Baker et al. (PCT Publication No. WO 99/46281) disclose a nucleic acid sequence of 1998 bp (SEQ ID NO: 25) encoding a polypeptide of 316 amino acids (SEQ ID NO: 26) that they designate as PRO352. Chapoval et al, 2001, *Nat. Immun.* 2:269-274, disclose a nucleic acid sequence of 951 bp (SEQ ID NO: 27) encoding a polypeptide of 316 amino acids (SEQ ID NO: 28) which they designate B7-H3. The nucleic acid sequence disclosed by Chapoval et al. is identical to the nucleic acid sequence that encodes B7RP-2 polypeptide.

EXAMPLE 2

B7RP-2 mRNA Expression

Figure 7:
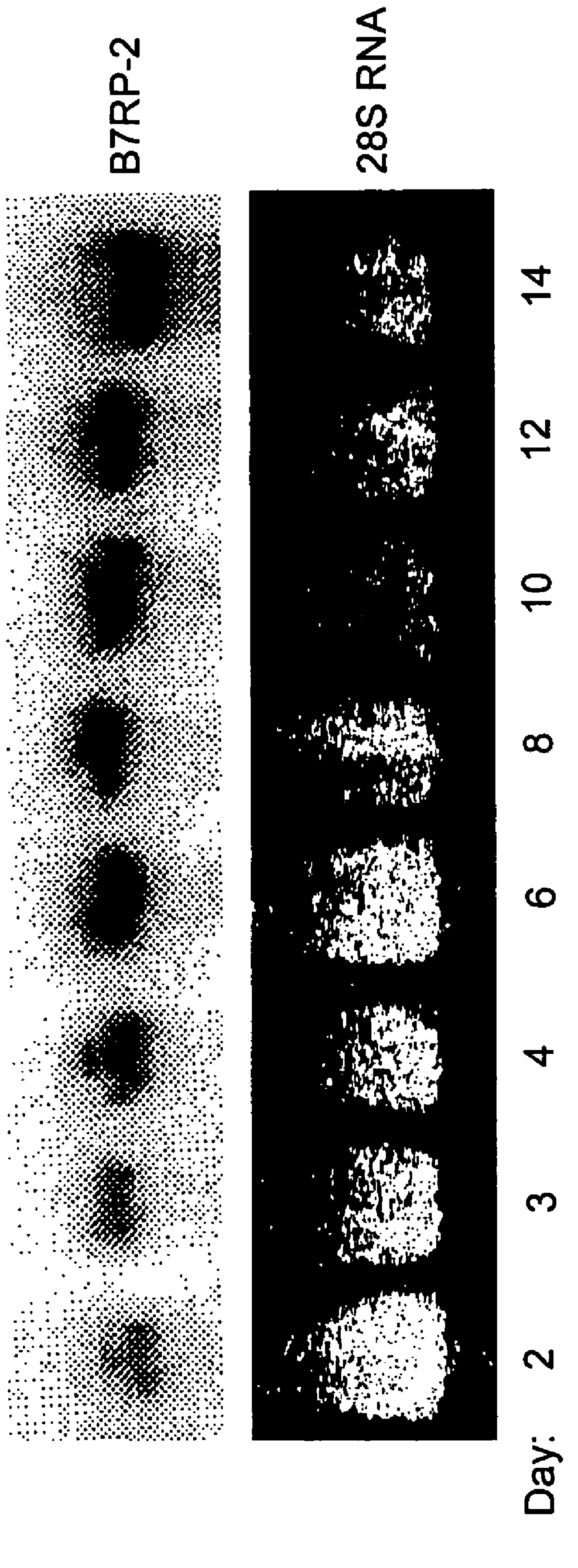
FIG. 7 illustrates the expression of B7RP-2 mRNA as detected by Northern blot analysis of osteoblast cells following treatment with dexamethasone, vitamin C, and □-glycerophosphate.

The kinetics of B7RP-2 mRNA expression during bone formation was examined in osteoblast cells following treatment with dexamethasone, vitamin C, and β-glycerophosphate. Osteoblasts were isolated from rat bone marrow and cultured in α-Minimal Essential Media containing 10% fetal calf serum, 3 ng/ml β-FGF, 50 μM β-mercaptoethanol, and antibiotics. Dexamethasone (10 nM) and vitamin C (50 μg/ml) were added to the media when the cells reached confluency, and the media was then renewed every other day until day 14. At day 8, β-glycerophosphate (50 μg/ml) was also added. Total RNA was prepared at days 2, 3, 4, 6, 8, 10, 12, and 14 and analysed by Northern blot analysis using the full-length rat B7RP-2 cDNA sequence as a probe. Each lane was loaded with an equal amount of RNA (20 μg/lane) as assessed by 28S and 18S rRNA. The increase in the expression of B7RP-2 mRNA following the addition of dexamethasone, vitamin C, and β-glycerophosphate (FIG. 7) indicates that B7RP-2 polypeptide might be involved in osteoblast growth or differentiation.

Figure 8:
FIG. 8 illustrates the expression of B7RP-2 mRNA in an E18.5 mouse embryo as detected by in situ hybridization.

The expression of B7RP-2 mRNA was localized by in situ hybridization. Normal mouse embryos (E18.5) were fixed in 4% paraformaldehyde, embedded in paraffin, and sectioned at 5 μm. Prior to hybridization, sections were permeabilized with 0.2 M HCl, digested with Proteinase K, and acetylated with triethanolamine and acetic anhydride. Sections were hybridized overnight at 55° C. with a $^{33}P$-labeled riboprobe corresponding to 5' and 3' sequences of the mouse B7RP-2 protein coding sequence. Following hybridization, sections were treated with RNaseA to digest unhybridized probe, and then washed with a series of buffers containing decreasing salt concentrations to a high stringency of 0.1×SSC at 55° C. Sections were then immersed in NTB2 emulsion (Kodak, Rochester, N.Y.), exposed for 2-3 weeks at 4° C., developed, and counterstained with hematoxilyn and eosin. Sections were examined with darkfield and transmitted light illumination to allow simultaneous evaluation of tissue morphology and hybridization signal. B7RP-2 mRNA expression was detected in the developing bones of an E18.5 mouse embryo (FIG. 8).

EXAMPLE 3

Production of B7RP-2 Polypeptides

A. Expression of B7RP-2 Polypeptides in Bacteria

PCR is used to amplify template DNA sequences encoding a B7RP-2 polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC no. 98113) containing the lux promoter and a gene encoding kanamycin resistance is digested with Bam HI and Nde I for directional cloning of inserted DNA. The ligated mixture is transformed into an *E. coli* host strain by electroporation and transformants are selected for kanamycin resistance. Plasmid DNA from selected colonies is isolated and subjected to DNA sequencing to confirm the presence of the insert.

Transformed host cells are incubated in 2×YT medium containing 30 μg/mL kanamycin at 30° C. prior to induction. Gene expression is induced by the addition of N-(3-oxohexanoyl)-dl-homoserine lactone to a final concentration of 30 ng/mL followed by incubation at either 30° C. or 37° C. for six hours. The expression of B7RP-2 polypeptide is evaluated by centrifugation of the culture, resuspension and lysis of the bacterial pellets, and analysis of host cell proteins by SDS-polyacrylamide gel electrophoresis.

Inclusion bodies containing B7RP-2 polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 mL of a Percoll solution (75% liquid Percoll and 0.15 M NaCl) until uniformly suspended and then diluted and centriftiged at 21,600×g for 30 minutes. Gradient fractions containing the inclusion bodies are recovered and pooled. The isolated inclusion bodies are analyzed by SDS-PAGE.

A single band on an SDS polyacrylamide gel corresponding to *E. coli*-produced B7RP-2 polypeptide is excised from the gel, and the N-terminal amino acid sequence is determined essentially as described by Matsudaira et al., 1987, *J. Biol. Chem.* 262:10-35.

B. Expression of B7RP-2 Polypeptide in Mammalian Cells

PCR is used to amplify template DNA sequences encoding a B7RP-2 polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary expression vector, pCEP4 (Invitrogen, Carlsbad, Calif.), that contains an Epstein-Barr virus origin of replication, may be used for the expression of B7RP-2 polypeptides in 293-EBNA-1 cells. Amplified and gel purified PCR products are ligated into pCEP4 vector and introduced into 293-EBNA cells by lipofection. The transfected cells are selected in 100 μg/mL hygromycin and the resulting drug-resistant cultures are grown to confluence. The cells are then cultured in serum-free media for 72 hours. The conditioned media is removed and B7RP-2 polypeptide expression is analyzed by SDS-PAGE.

B7RP-2 polypeptide expression may be detected by silver staining. Alternatively, B7RP-2 polypeptide is produced as a fusion protein with an epitope tag, such as an IgG constant domain or a FLAG epitope, which may be detected by Western blot analysis using antibodies to the peptide tag.

B7RP-2 polypeptides may be excised from an SDS-polyacrylamide gel, or B7RP-2 fusion proteins are purified by affinity chromatography to the epitope tag, and subjected to N-terminal amino acid sequence analysis as described herein.

C. Expression and Purification of B7RP-2 Polypeptide in Mammalian Cells

B7RP-2 polypeptide expression constructs are introduced into 293 EBNA or CHO cells using either a lipofection or calcium phosphate protocol.

To conduct functional studies on the B7RP-2 polypeptides that are produced, large quantities of conditioned media are generated from a pool of hygromycin selected 293 EBNA clones. The cells are cultured in 500 cm Nunc Triple Flasks to 80% confluence before switching to serum free media a week prior to harvesting the media. Conditioned media is harvested and frozen at −20° C. until purification.

Conditioned media is purified by affinity chromatography as described below. The media is thawed and then passed through a 0.2 μm filter. A Protein G column is equilibrated with PBS at pH 7.0, and then loaded with the filtered media. The column is washed with PBS until the absorbance at $A_{280}$ reaches a baseline. B7RP-2 polypeptide is eluted from the column with 0.1 M Glycine-HCl at pH 2.7 and immediately neutralized with 1 M Tris-HCl at pH 8.5. Fractions containing B7RP-2 polypeptide are pooled, dialyzed in PBS, and stored at −70° C.

For Factor Xa cleavage of the human B7RP-2 polypeptide-Fc fusion polypeptide, affinity chromatography-purified protein is dialyzed in 50 mM Tris-HCl, 100 mM NaCl, 2 mM $CaCl_2$ at pH 8.0. The restriction protease Factor Xa is added to the dialyzed protein at 1/100 (w/w) and the sample digested overnight at room temperature.

EXAMPLE 4

In Vitro Characterization of B7RP-2 Polypeptides

Figure 9:
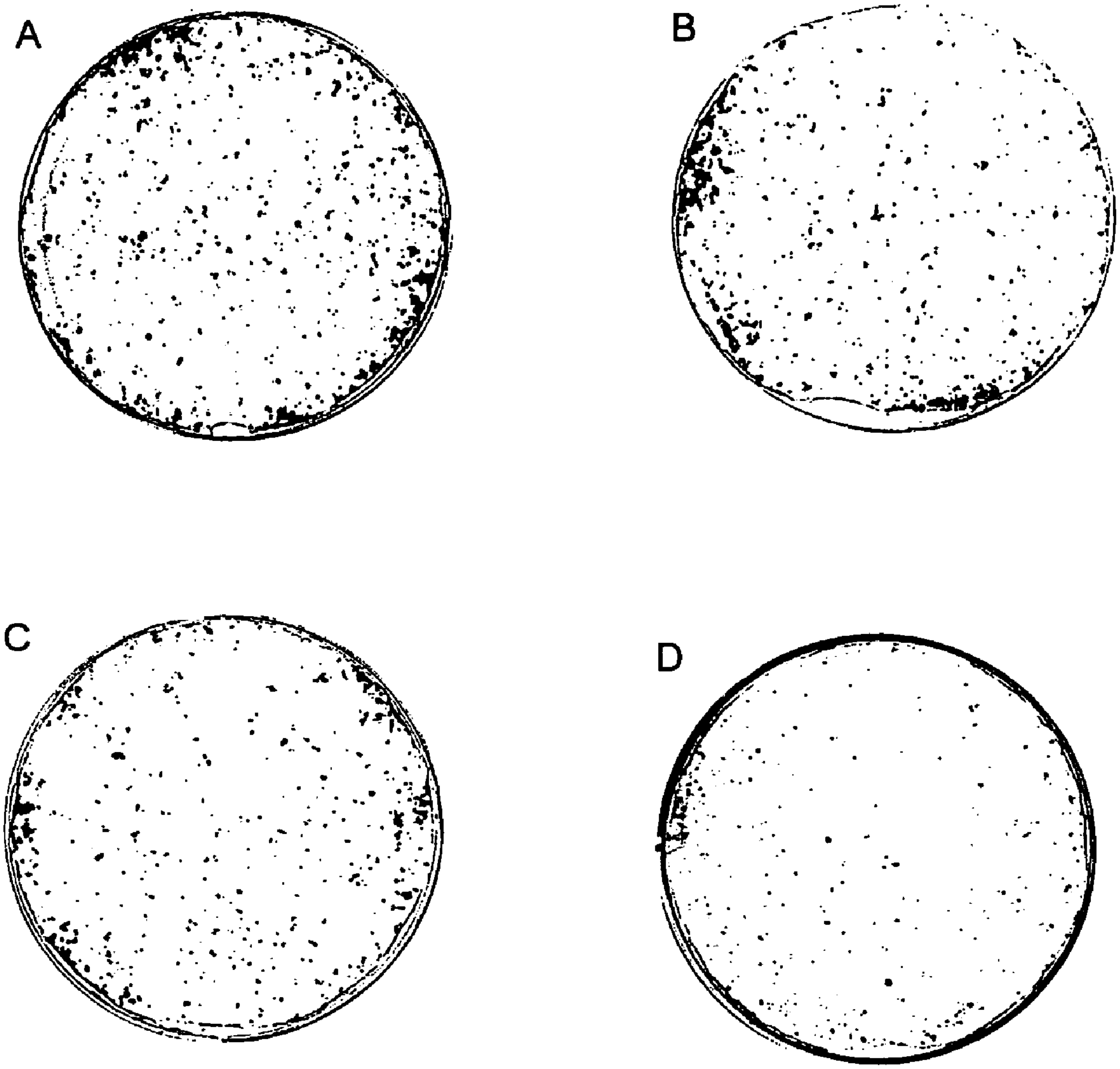
FIG. 9 illustrates the inhibition of bone mineralization by B7RP-2 polypeptide. Cells were either treated with no polypeptide (plate A), 10 μg/ml of an IgG1 isotype control (plate B), 1 μg/ml of soluble B7RP-2 polypeptide (plate C) or 10 μg/ml (plate D) of soluble B7RP-2 polypeptide.

The inhibitory activity of B7RP-2 mRNA expression during bone mineralization was examined in calvarial cells following treatment with dexamethasone, vitamin C, and β-glycerophosphate. Calvarial cells were isolated from neonatal mice (CD1 strain) and cultured in α-Minimal Essential Media containing 10% fetal calf serum, 50 μM β-mercaptoethanol, and antibiotics. Dexamethasone (10 nM) and vitamin C (50 μg/ml) were added to the media when the cells reached confluency, and the media was then renewed every other day until day 14. At day 12, β-glycerophosphate (10 mM) was also added. At day 14, the degree of bone mineralization was determined by von Kossa staining. Soluble B7RP-2 polypeptide was found to inhibit nodule formation and mineralization in a dose dependent manner in vitro (FIG. 9), indicating that B7RP-2 polypeptide might be involved in the regulation of bone formation.

Figure 10C:
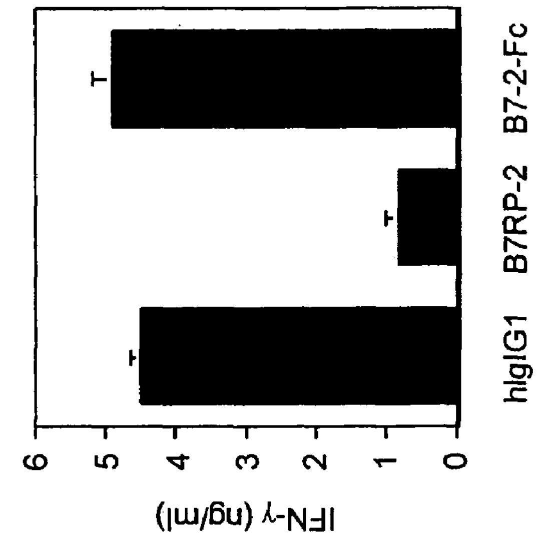
FIGS. 10A-10C illustrate the effect of B7RP-2 on T-cell proliferation, interleukin-2 production, and interferon-γ production.
Figure 10B:
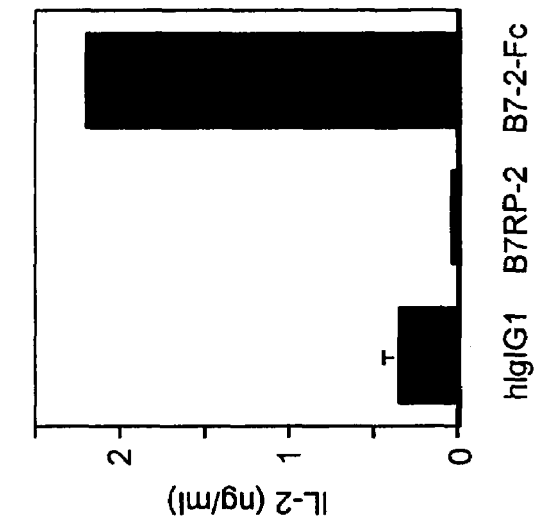
Figure 10A:
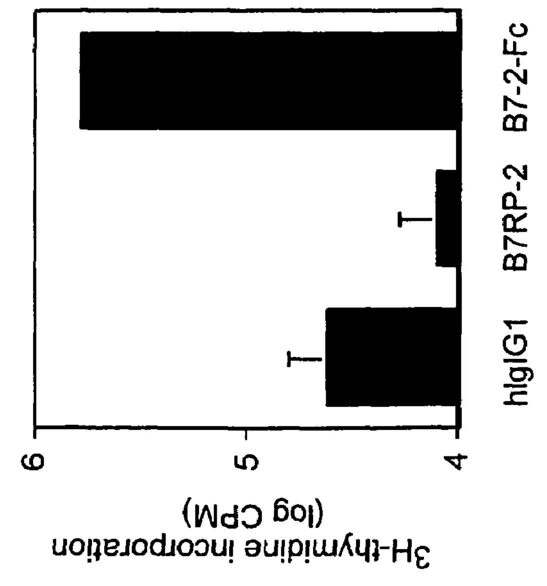

Recombinant protein comprising the two extracellular Ig domains of B7RP-2 fused in-frame to the Fc portion of human IgG1 (B7RP-2-Fc) was synthesized. Lymph node cells from C57BL/6 mice were depleted of $B220^+$ cells using magnetic beads (Dynal, Oslo, Norway). Purified lymph node T-cells were activated using plate-bound anti-CD3 (0.1 μg/ml) plus 10 μg/ml of plate-bound human IgG1 (isotype control), B7RP-2-Fc, or B7-2-Fc (positive control) in U-bottom 96-well plates. T-cell proliferation was assayed by pulsing the cells with $^3$H-thymidine during the last 8 hours of a 72-hour incubation period. The B7RP-2-Fc inhibited T-cell proliferation up to 5-fold compared to controls (FIG. 10A). Interleukin-2 (IL-2) (FIG. 10B) and interferon-γ (IFN-γ) (FIG. 10C) production in the culture supernatants was measured using ELISA. IL-2 and IFN-γ production were similarly reduced, most likely because of the decrease in T-cell proliferation (FIGS. 10B and 10C). These results indicate that B7RP-2 inhibits TCR-mediated T-cell proliferation in vitro.

EXAMPLE 5

In Vivo Characterization of B7RP-2

A. Generation of B7RP-2−/− Mice

Figure 11:
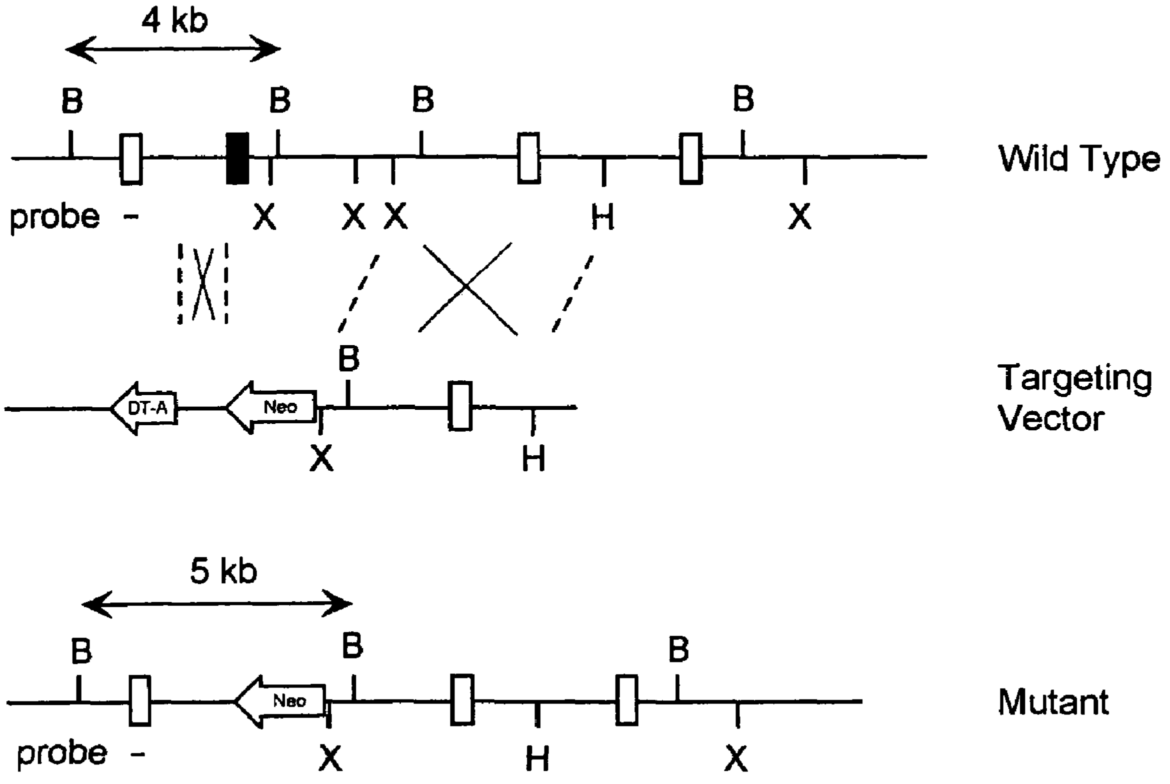
FIG. 11 illustrates the wild type murine B7RP-2 locus, targeting vector, and mutated B7RP-2 allele for generating B7RP-2–/– mice. (B, Bgl II; H, Hind III; X, Xba I)

The in vivo role of B7RP-2 was examined by generating B7RP-2 deficient mice. A murine B7RP-2 genomic clone was isolated from a 129/J phage library using the full-length rat B7RP-2 cDNA as a probe. A targeting vector was designed to replace the exon encoding the second Ig domain of B7RP-2 with a neomycin resistance cassette (FIG. 11). A ~3.2 kb genomic sequence encompassing the exon encoding the second Ig domain of B7RP-2 (filled rectangle in FIG. 11) was replaced by the PGK promoter-driven neomycin resistance gene (Neo). The diphtheria toxin A gene (DT-A) was used for negative selection. The targeting vector was introduced into E14 embryonic stem (ES) cells (129/Ola) by direct micoinjection, and ES cell clones were screened by PCR to identify clones that had undergone homologous recombination.

Selected ES clones were verified by Southern blot analysis. For Southern blotting, Bgl II-digested genomic DNA from B7RP-2+/+, +/− and −/− mice was hybridized to the 5' flanking probe shown in FIG. 11. C57BL/6 blastocysts were injected with B7RP-2+/− ES cells and implanted in pseudopregnant female mice. The resulting chimeric mice were bred with C57BL/6 mice to obtain heterozygous F1 progeny, which were interbred to generate B7RP-2−/− mice. B7RP-2−/− mice derived from two independent ES clones showed the same phenotypes.

Figure 12:
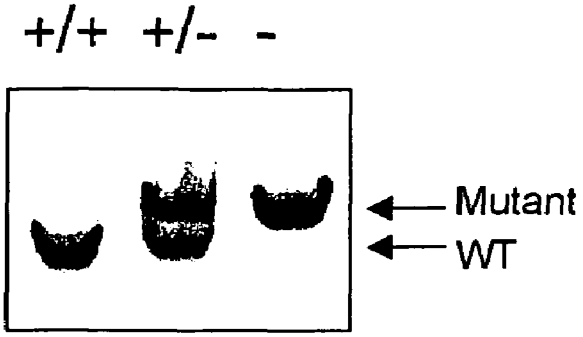
FIG. 12 depicts a Southern analysis of genomic DNA from F2 progeny verifying the disruption of the B7RP-2 gene.
Figure 13:
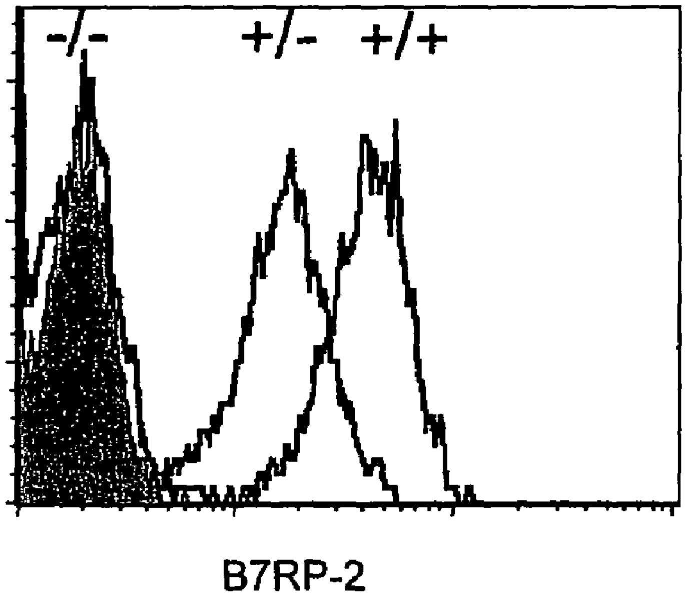
FIG. 13 depicts a flow cytometric analysis of B7RP-2 protein expression in MEF cells of the indicated genotypes.

Disruption of the B7RP-2 gene was confirmed by Southern analysis of genomic DNA from F2 progeny (FIG. 12). Anti-B7RP-2 antibodies were used to verify that the mice were not producing B7RP-2 protein. Rabbit polyclonal antibody was raised against rat B7RP-2-Fc protein. The antiserum was purified through a protein A column and anti-Fc antibodies were removed using an Fc affinity column. The flow cytometric analysis of mouse embryonic fibroblasts (MEF) from the B7RP-2−/− mice confirmed the absence of B7RP-2 protein (FIG. 13). MEF were stained with anti-B7RP-2 rabbit IgG and FITC-Conjugated Goat Anti-Rabbit IgG.

B7RP-2−/− mice were obtained at the expected Mendelian ratio, and were found to be of normal size, maturation, and fertility. T-, B-, and NK-cell populations in the bone marrow, thymus, lymph node, spleen, and peripheral blood were normal in B7RP-2−/− mice. C57BL/6×129/Ola F2 and F3 animals were used for subsequent analysis.

B. T-Cell Response In B7RP-2−/− Mice

The B7RP-2−/− mice were used to determine if the absence of B7RP-2 protein contributes to heightened T-cell-mediated hypersensitivity. Airway inflammation models driven by either Th1 or Th2 cells, and a footpad-swelling model that reflects cytotoxic T lymphocyte (CTL) response to lymphocytic choriomeningitis virus (LCMV) infection, were used to examine T-cell response. Cytokine (Th1- or Th2-polarizing) microenvironments were established in the airways of B7RP-2+/+ and B7RP-2−/− mice by transient, adenovirus-mediated intranasal expression of GM-CSF plus IL-12 (Th1) or GM-CSF alone (Th2). Intranasal expression of replication-deficient adenovirus carrying the appropriate cytokine cDNA was initiated on day (−)1. The +/+ and −/− mice were exposed to ovalbumin (OVA) aerosol (1% wt/vol in 0.9% saline) for 20 minutes on 10 consecutive days (days 0-9) to cause airway inflammation. On day 11, the mice were killed and immune cell populations in the bronchoalveolar lavage (BAL) fluids were differentially stained and counted. The remaining lung tissue was processed for histologic examination by hematoxylin and eosin (H&E) staining. In some cases, lung cells were released by collagenase treatment and analyzed by flow cytometry. Ex vivo splenocytes were cultured in the absence or presence of 400 μg/ml OVA for 5 days prior to determination of cytokine production by ELISA (R&D Systems).

Figure 15:
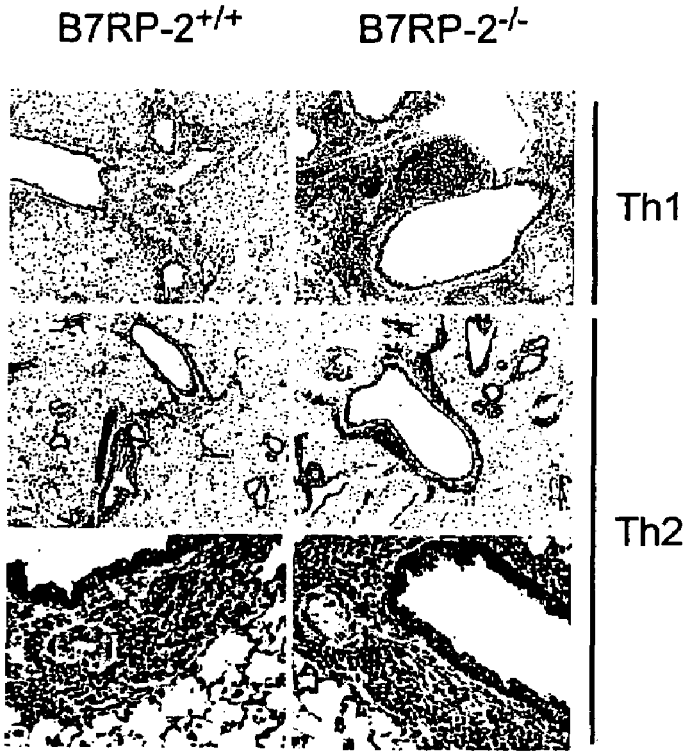
FIG. 15 depicts hematoxylin and exosin staining of lung sections from the B7RP-2–/– and +/+ mice having cytokine-induced airway inflammation.
Figure 14:
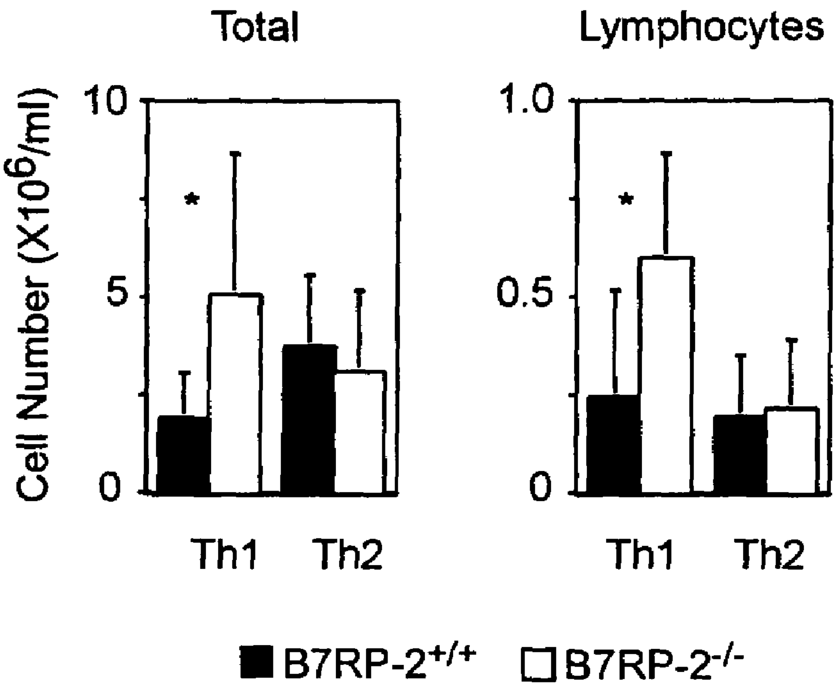
FIG. 14 shows total and lymphocyte cell counts in the bronchoalveolar lavage (BAL) fluid from the B7RP-2–/– and +/+ mice having cytokine-induced airway inflammation.
Figure 16:
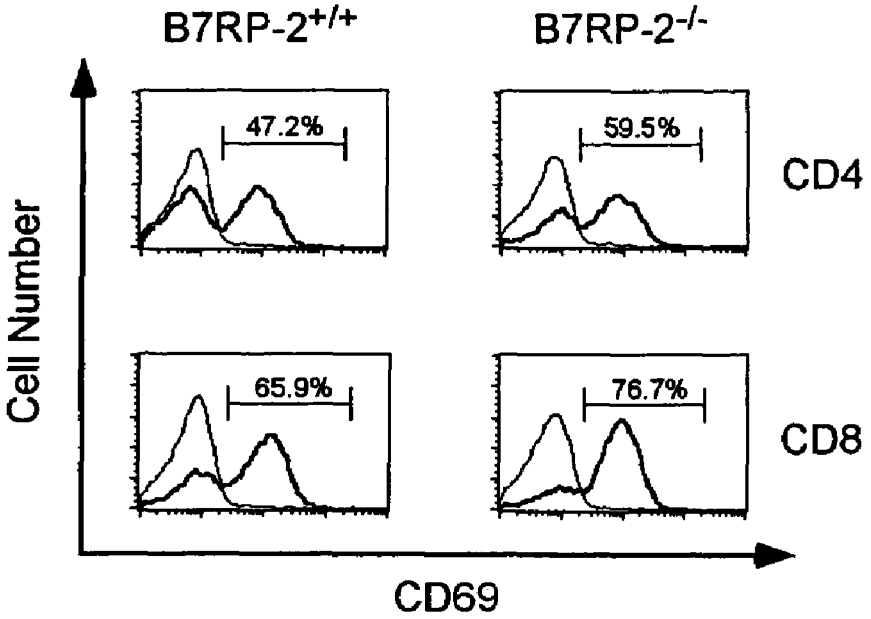
FIG. 16 depicts flow cytometric analysis of lung-infiltrating T-cells based on lung infiltrates pooled from B7RP-2–/– and +/+ mice having cytokine-induced airway inflammation (four mice in each group)

After OVA sensitization under Th1 conditions, B7RP-2−/− mice had 2.5-fold more infiltrating immune cells in the airway compared to B7RP-2+/+ (FIG. 14; Total). Lymphocyte (FIG. 14; Lymphocytes), macrophage, and neutrophil subsets were increased to a similar degree. Histological examination of lung sections confirmed infiltration of increased severity in the absence of B7RP-2 (FIG. 15; Th1). The portion of activated ($CD69^+$) cells in both $CD4^+$ and $CD8^+$ T-cell populations in lung infiltrates of B7RP-2−/− mice compared to controls (59.5% and 47.2%, respectively, among $CD4^+$ T-cells; 76.7% and 65.9% among $CD8^+$ T-cells; FIG. 16).

Splenocytes harvested from B7RP-2−/− mice sensitized under Th1 conditions produced about 60% more IFN-γ when restimulated in vitro with OVA compared to B7RP-2+/+ splenocytes. Under Th2 conditions, however, similar numbers of lung-infiltrating immune cells were found in BAL fluids and lung sections from B7RP-2+/+ and B7RP-2−/− mice (FIGS. 14 and 15; Th2). Eosinophilia, a hallmark of Th2-driven airway inflammation, was also comparable (FIG. 15; Th2; bottom panel), and OVA-stimulated B7RP-2+/+ and −/− splenocytes consistently produced similar levels of IL-4, IL-5, and IL-13. Thus, in situations of Th1- but not Th2-driven airway inflammation, B7RP-2−/− mice develop more severe disease than control mice and display augmented T-cell activation.

Figure 17:
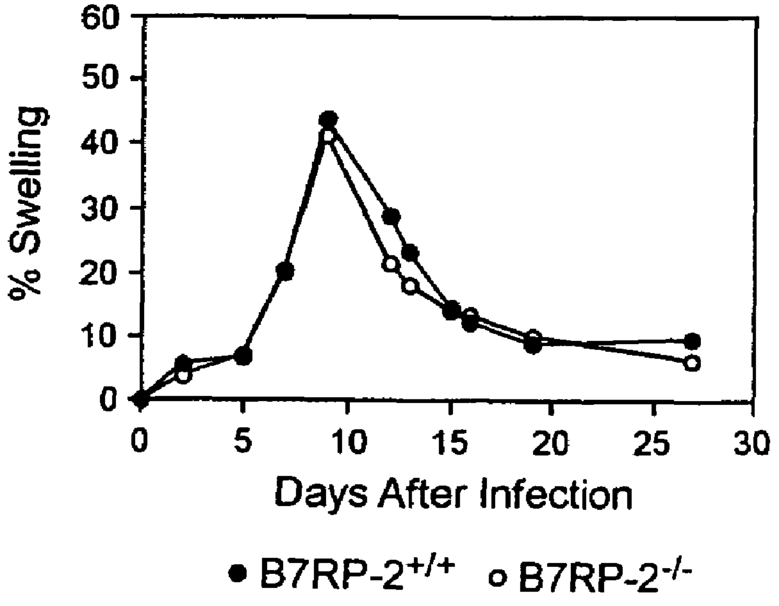
FIG. 17 depicts LCMV-induced footpad swelling of B7RP-2–/– and +/+ mice.

The role of B7RP-2 in a CTL-mediated hypersensitivity reaction was examined by injecting LCMV into the footpads of B7RP-2+/+ and −/− mice. The extent and kinetics of footpad swelling were indistinguishable between genotypes (FIG. 17). These data indicate that B7RP-2 is involved in downregulating Th1-mediated responses, but not in Th2- or CTL-mediated hypersensitivity reactions.

EXAMPLE 6

Role of B7RP-2 in Experimental Autoimmune Encephalomyelitis (EAE)

The role of B7RP-2 was also investigated in experimental autoimmune encephalomyelitis (EAE), another Th1-driven disease model. Induction and clinical scoring of EAE was performed as follows. EAE was induced by immunizing mice with the peptide antigen representing amino acids 35-55 of myelin oligodendrocyte glycoprotein (MOG) M-E-V-G-W-Y-R-S-P-F-S-R-V-V-H-L-Y-R-N-G-K (SEQ ID NO: 29). B7RP-2+/+ and −/− littermates (8-12 weeks) were injected subcutaneously (s.c.) on day 0 and day 7 with 300 μg MOG 35-55 peptide emulsified in CFA (Sigma) plus 500 μg *Mycobacterium tuberculosis*. The mice were injected intraperitoneally (i.p.) with 500 ng pertussis toxin (List Biological, Campbell, Calif.) on day 0 and day 2. EAE clinical scores were determined daily as follows (with a gradation of 0.5 for intermediate levels): 0, no clinical signs; 1, loss of tail tone; 2, wobbly gait; 3, hind limb paralysis; 4, hind and fore limb paralysis; 5, death.

Figure 18A:
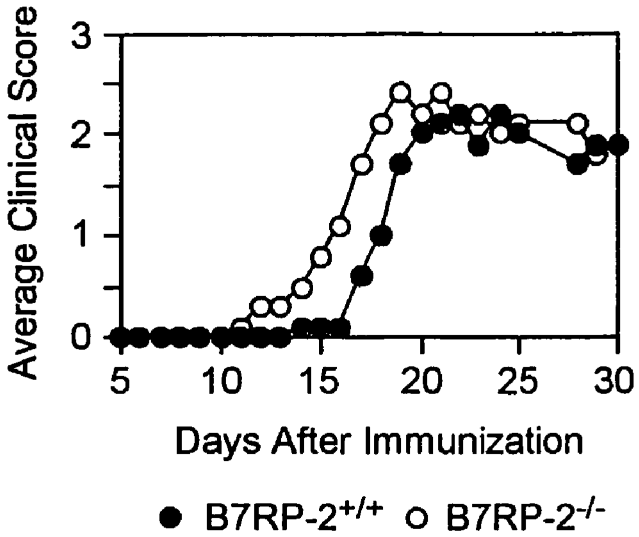
FIGS. 18A-18B depict the disease course for experimental autoimmune encephalomyelitis (EAE) in B7RP-2–/– and +/+ mice as determined by the average clinical score of all mice in a group (FIG. 16A), and the time of EAE onset compared among littermates (FIG. 16B); Ci Circles in the same row represent individual mice from the same litter; results shown are a summary of four independent experiments.
Figure 18B:
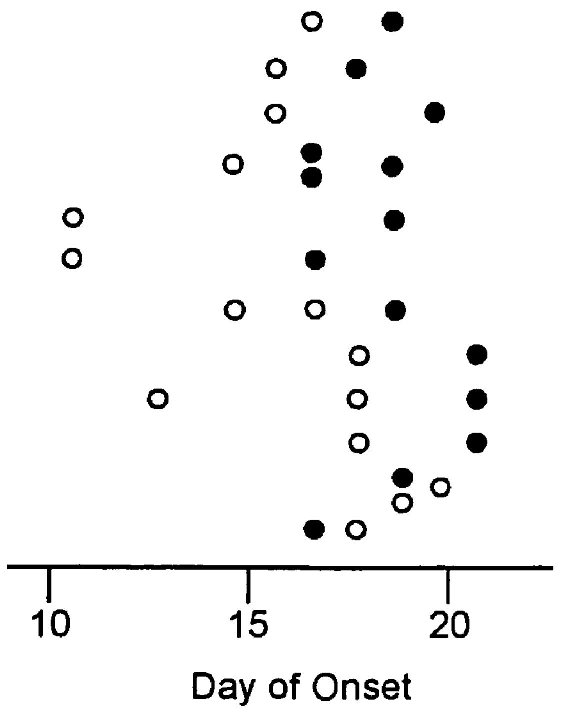

The average day of disease onset (the first day when the clinical score was higher than 1) was earlier in B7RP-2−/− mice (day 16.1; n=16) than in B7RP-2+/+ mice (day 18.4; n=14) (FIG. 18A), a trend clarified when littermates were compared (FIG. 18B). Despite the earlier onset, B7RP-2−/− mice had the same clinical scores as B7RP-2 +/+ mice by the late stages of the disease (FIG. 18A). The rates of disease incidence (14/16 in +/+ and 16/18 in −/−) or mortality (1/14 in +/+ vs. 3/16 in −/−) were also equivalent. The earlier onset of EAE in the absence of B7RP-2 provides support for the hypothesis that B7RP-2 negatively regulates Th1-driven immune responses.

EXAMPLE 7

Cytotoxic T Lymphocytes (CTL) Response in B7RP-2−/− Mice

A. Lymphocytic Choriomeningitis Virus (LCMV)-Specific CTL Response

Figure 19:
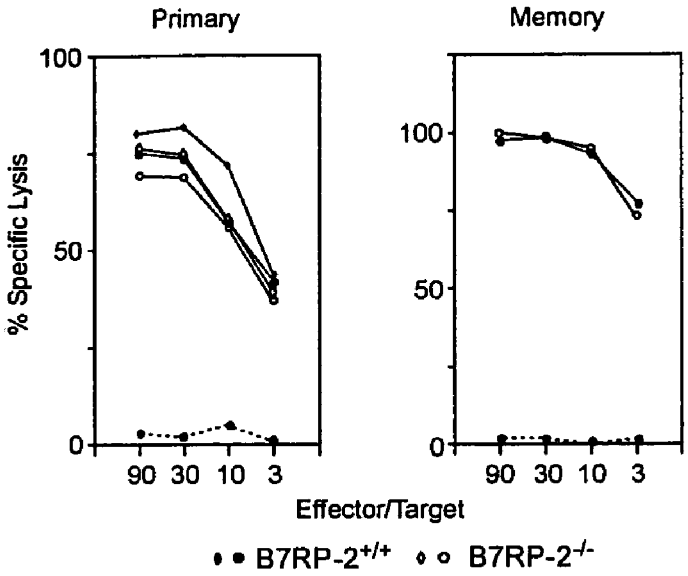
FIG. 19 illustrates the CTL response to LCMV in splenocytes from B7RP-2–/– and +/+ mice harvested 8 days post-infection, and a memory CTL response to LCMV in splenocytes from B7RP-2–/– and +/+ mice harvested 30 days post-infection and restimulated for 5 days in vitro.

The effect of B7RP-2 on the anti-viral cytotoxic T lymphocytes (CTL) responses to lymphocytic choriomeningitis virus (LCMV) or influenza virus was also examined in vivo. For primary CTL responses, B7RP-2−/− and +/+ mice were injected intravenously (i.v.) with 2000 pfu LCMV (Armstrong strain). At day 8 post-infection, splenocytes were harvested and ex vivo CTL activity was measured by a standard $^{51}$Cr release assay using $^{51}$Cr-labeled EL4 cells pulsed with LCMV glycoprotein peptide p33 (K-A-V-Y-N-F-A-T-M; SEQ ID NO: 30). The splenocytes from B7RP-2−/− mice on day 8 post-infection with LCMV showed the same level of ex vivo CTL activity as those from B7RP-2+/+ mice (FIG. 19; Primary).

The CTL memory response in B7RP-2−/− and +/+ mice was examined using the footpad swelling assays. For footpad swelling, 3000 pfu LCMV (Armstrong strain) was injected into the hind footpad of B7RP-2−/− and +/+ mice and the footpad thickness was measured with calipers. To measure memory CTL activity, the mice that were used for the footpad swelling experiments were killed at day 30 and the splenocytes were harvested. The harvested splenocytes were restimulated in vitro by culturing the cells for 5 days in the presence of 1 μM p33 peptide and rat splenocyte ConA culture supernatant. Cytotoxicity was measured as above. The levels of CTL activity detected in the splenocytes harvested from the B7RP-2−/− mice were comparable to those harvested from the B7RP +/+ mice (FIG. 19; Memory). These experiments indicate that normal primary and memory CTL responses against LCMV can be mounted in the absence of B7RP-2.

B. Influenza Virus Nucleoprotein (NP)-Specific CTL Response

Figure 20:
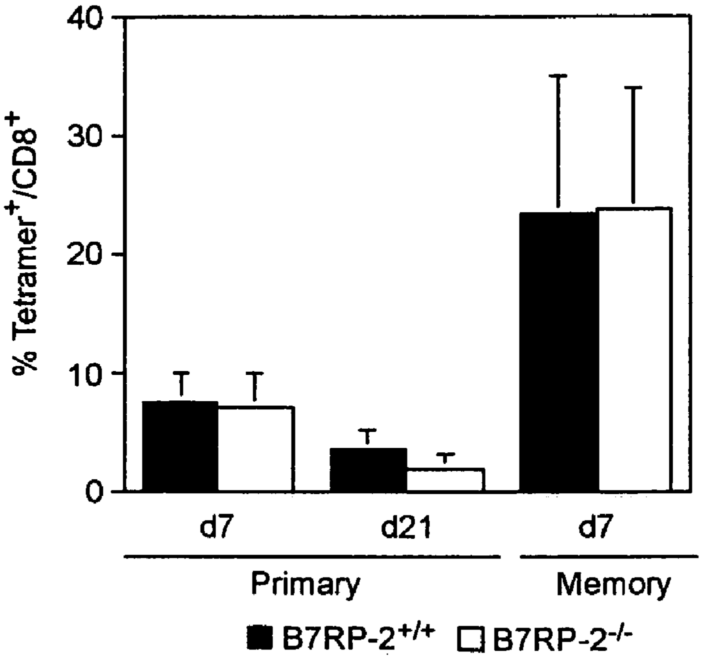
FIG. 20 illustrates the CTL response and CTL memory response to influenza virus in splenocytes harvested from B7RP-2–/– and +/+ mice.

To rule out the possibility that the strong antigenic stimulation associated with LCMV infection masked a need for costimulatory signals, CTL responses to influenza virus were examined. B7RP-2−/− and +/+ mice were infected intraperitoneally (i.p.) with 200 hemaglutinin units (HAU) of influenza A HK×31(H3N1). Expansion of influenza nucleoprotein (NP)-specific CTL was monitored by flow cytometric analysis of splenocytes stained on day 7 and day 21 post-infection with anti-CD8 mAb (ebioscience, San Diego, Calif.) and the tetramer H-2D$^b$/NP366-374 (A-S-N-E-N-M-E-T-M; SEQ ID NO: 31) (NIAID MHC Tetramer Core Facility, Atlanta, Ga.). The expansion of NP366-374/H-2Db-specific CTLs during primary and secondary influenza virus infections was indistinguishable in B7RP-2+/+ and −/− mice (FIG. 20). For memory CTL responses, B7RP-2+/+ and −/− mice (four mice/group) were infected with HK×31 and re-infected 4 weeks later with the serologically distinct influenza virus A/PR/8/34 (H1N1), which shares the same NP gene with HK×31. Splenocytes were harvested and analyzed by tetramer staining 7 days after re-infection. There were no differences in the number of IFN-γ producing cells among CD8$^+$ T-cells and the cytotoxicity of splenocytes restimulated in vitro.

EXAMPLE 8

Production of Anti-B7RP-2 Polypeptide Antibodies

Antibodies to B7RP-2 polypeptides may be obtained by immunization with purified protein or with B7RP-2 peptides produced by biological or chemical synthesis. Suitable procedures for generating antibodies include those described in Hudson and Bay, *Practical Immunology* (2nd ed., Blackwell Scientific Publications).

In one procedure for the production of antibodies, animals (typically mice or rabbits) are injected with a B7RP-2 antigen (such as a B7RP-2 polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), are first incubated in DMEM with 200 U/mL penicillin, 200 μg/mL streptomycin sulfate, and 4 mM glutamine, and are then incubated in HAT selection medium (hypoxanthine, aminopterin, and thymidine). After selection, the tissue culture supernatants are taken from each fusion well and tested for anti-B7RP-2 antibody production by ELISA.

Alternative procedures for obtaining anti-B7RP-2 antibodies may also be employed, such as the immunization of transgenic mice harboring human Ig loci for production of human antibodies, and the screening of synthetic antibody libraries, such as those generated by mutagenesis of an antibody variable domain.

EXAMPLE 9

Expression of B7RP-2 Polypeptide in Transgenic Mice

To assess the biological activity of B7RP-2 polypeptide, a construct encoding a B7RP-2 polypeptide/Fc fusion protein under the control of a liver specific ApoE promoter is prepared. The delivery of this construct is expected to cause pathological changes that are informative as to the function of B7RP-2 polypeptide. Similarly, a construct containing the full-length B7RP-2 polypeptide under the control of the beta actin promoter is prepared. The delivery of this construct is expected to result in ubiquitous expression.

To generate these constructs, PCR is used to amplify template DNA sequences encoding a B7RP-2 polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified B7RP-2 polypeptide sequences can be cloned into an expression vector under the control of the human β-actin promoter as described by Graham et al., 1997, *Nature Genetics,* 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The B7RP-2 polypeptide expression vector is purified through two rounds of CsCl density gradient centrifugation, cleaved with a suitable restriction enzyme, and the linearized fragment containing the B7RP-2 polypeptide transgene is purified by gel electrophoresis. The purified fragment is resuspended in 5 mM Tris, pH 7.4, and 0.2 mM EDTA at a concentration of 2 mg/mL.

Single-cell embryos from BDF1×BDF1 bred mice are injected as described (PCT Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (Qiagen) and transgene expression determined by RT-PCR. RNA recovered from spleens is converted to cDNA using the SuperScript™ Preamplification System (Gibco-BRL) as follows. A suitable primer, located in the expression vector sequence and 3' to the B7RP-2 polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of SuperScript II reverse transcriptase. Following incubation for 50 minutes at 42° C., the reaction is stopped by heating for 15 minutes at 72° C. and digested with 2U of RNase H for 20 minutes at 37° C. Samples are then amplified by PCR using primers specific for B7RP-2 polypeptide.

EXAMPLE 10

Biological Activity of B7RP-2 Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B-cell and T-cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately $1\times10^6$ cells from each tissue are then incubated for 10 minutes with 0.5 μg CD16/32(FcγIII/II) Fc block in a 20 μL volume. Samples are then stained for 30 minutes at 2-8° C. in a 100 μL volume of PBS (lacking $Ca^+$ and $Mg^+$), 0.1% bovine serum albumin, and 0.01% sodium azide with 0.5 μg antibody of FITC or PE-conjugated monoclonal antibodies against CD90.2 (Thy-1.2), CD45R (B220), CD11b (Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A method for inhibiting T-cell proliferation comprising administering to a patient a fusion polypeptide comprising:

the amino acid sequence as set forth in SEQ ID NO:2, with at least one conservative amino acid substitution, wherein the at least one conservative amino acid substitution is located at position 20, 29, 101, 120, 184, 260, 261, 291, or 306 of SEQ ID NO:2;

wherein the polypeptide is fused to an Fc, has T-cell proliferation inhibiting activity and is administered in an amount effective to inhibit T-cell proliferation.

2. A method for delaying onset of experimental autoimmune encephalomyelitis (EAE) comprising administering to a subject a fusion polypeptide comprising:

(a) a fragment of the amino acid sequence set forth in SEQ ID NO:2, comprising at least two extracellular Ig domains of the polypeptide of SEQ ID NO:2; or (b) the amino acid sequence as set forth in SEQ ID NO:2, with at least one conservative amino acid substitution, wherein the at least one conservative amino acid substitution is located at position 20, 29, 101, 120, 184, 260, 261, 291, or 306 of SEQ ID NO:2;

wherein the polypeptide is fused to an Fc, has T-cell proliferation inhibiting activity and is administered in an amount effective to treat, prevent or ameliorate an autoimmune disease.

3. A method for downregulating an immune response comprising administering to a patient a fusion polypeptide comprising:

the amino acid sequence as set forth in SEQ ID NO:2, with at least one conservative amino acid substitution, wherein the at least one conservative amino acid substitution is located at position 20, 29, 101, 120, 184, 260, 261, 291, or 306 of SEQ ID NO:2;

wherein the polypeptide is fused to an Fc, has T-cell proliferation inhibiting activity and is administered in an amount effective to downregulate an immune response.

4. The method of claim 3, wherein the immune response is Th-1 mediated.

5. The method of claim 4, wherein the downregulating activity of the polypeptide does not downregulate Th-2 or CTL-mediated hypersensitivity reactions.

6. The method of claim 3 wherein the polypeptide is a soluble form of the polypeptide.

7. The method of claim 1 wherein the polypeptide is a soluble form of the polypeptide.

8. The method of claim 2 wherein the polypeptide is a soluble form of the polypeptide.

* * * * *

SEQUENCE LISTING

```
<160> NUMBER OF SEQ ID NOS: 32

<210> SEQ ID NO 1
<211> LENGTH: 1337
<212> TYPE: DNA
<213> ORGANISM: Homo sapiens
<220> FEATURE:
<221> NAME/KEY: CDS
<222> LOCATION: (135)..(1082)

<400> SEQUENCE: 1

ccgggtcgac ccacgcgtcc ggcggcggcg actgagccag gctgggccgc gtccctgagt      60

cccagagtcg gcgcggcgcg gcaggggcag ccttccacca cggggagccc agctgtcagc     120

cgcctcacag gaag atg ctg cgt cgg cgg ggc agc cct ggc atg ggt gtg       170
                Met Leu Arg Arg Arg Gly Ser Pro Gly Met Gly Val
                1               5                   10

cat gtg ggt gca gcc ctg gga gca ctg tgg ttc tgc ctc aca gga gcc       218
His Val Gly Ala Ala Leu Gly Ala Leu Trp Phe Cys Leu Thr Gly Ala
        15                  20                  25

ctg gag gtc cag gtc cct gaa gac cca gtg gtg gca ctg gtg ggc acc       266
Leu Glu Val Gln Val Pro Glu Asp Pro Val Val Ala Leu Val Gly Thr
    30                  35                  40

gat gcc acc ctg tgc tgc tcc ttc tcc cct gag cct ggc ttc agc ctg       314
Asp Ala Thr Leu Cys Cys Ser Phe Ser Pro Glu Pro Gly Phe Ser Leu
45                  50                  55                  60

gca cag ctc aac ctc atc tgg cag ctg aca gat acc aaa cag ctg gtg       362
Ala Gln Leu Asn Leu Ile Trp Gln Leu Thr Asp Thr Lys Gln Leu Val
                65                  70                  75

cac agc ttt gct gag ggc cag gac cag ggc agc gcc tat gcc aac cgc       410
His Ser Phe Ala Glu Gly Gln Asp Gln Gly Ser Ala Tyr Ala Asn Arg
            80                  85                  90

acg gcc ctc ttc ccg gac ctg ctg gca caa ggc aat gca tcc ctg agg       458
Thr Ala Leu Phe Pro Asp Leu Leu Ala Gln Gly Asn Ala Ser Leu Arg
        95                  100                 105

ctg cag cgc gtg cgt gtg gcg gac gag ggc agc ttc acc tgc ttc gtg       506
Leu Gln Arg Val Arg Val Ala Asp Glu Gly Ser Phe Thr Cys Phe Val
    110                 115                 120

agc atc cgg gat ttc ggc agc gct gcc gtc agc ctg cag gtg gcc gct       554
Ser Ile Arg Asp Phe Gly Ser Ala Ala Val Ser Leu Gln Val Ala Ala
125                 130                 135                 140

ccc tac tcg aag ccc agc atg acc ctg gag ccc aac aag gac ctg cgg       602
Pro Tyr Ser Lys Pro Ser Met Thr Leu Glu Pro Asn Lys Asp Leu Arg
                145                 150                 155

cca ggg gac acg gtg acc atc acg tgc tcc agc tac cgg ggc tac cct       650
Pro Gly Asp Thr Val Thr Ile Thr Cys Ser Ser Tyr Arg Gly Tyr Pro
            160                 165                 170

gag gct gag gtg ttc tgg cag gat ggg cag ggt gtg ccc ctg act ggc       698
Glu Ala Glu Val Phe Trp Gln Asp Gly Gln Gly Val Pro Leu Thr Gly
        175                 180                 185

aac gtg acc acg tcg cag atg gcc aac gag cag ggc ttg ttt gat gtg       746
Asn Val Thr Thr Ser Gln Met Ala Asn Glu Gln Gly Leu Phe Asp Val
    190                 195                 200
```

-continued

```
cac agc gtc ctg cgg gtg gtg ctg ggt gcg aat ggc acc tac agc tgc      794
His Ser Val Leu Arg Val Val Leu Gly Ala Asn Gly Thr Tyr Ser Cys
205                 210                 215                 220

ctg gtg cgc aac ccc gtg ctg cag cag gat gcg cac ggc tct gtc acc      842
Leu Val Arg Asn Pro Val Leu Gln Gln Asp Ala His Gly Ser Val Thr
                225                 230                 235

atc aca ggg cag cct atg aca ttc ccc cca gag gcc ctg tgg gtg acc      890
Ile Thr Gly Gln Pro Met Thr Phe Pro Pro Glu Ala Leu Trp Val Thr
            240                 245                 250

gtg ggg ctg tct gtc tgt ctc att gca ctg ctg gtg gcc ctg gct ttc      938
Val Gly Leu Ser Val Cys Leu Ile Ala Leu Leu Val Ala Leu Ala Phe
        255                 260                 265

gtg tgc tgg aga aag atc aaa cag agc tgt gag gag gag aat gca gga      986
Val Cys Trp Arg Lys Ile Lys Gln Ser Cys Glu Glu Glu Asn Ala Gly
    270                 275                 280

gct gag gac cag gat ggg gag gga gaa ggc tcc aag aca gcc ctg cag     1034
Ala Glu Asp Gln Asp Gly Glu Gly Glu Gly Ser Lys Thr Ala Leu Gln
285                 290                 295                 300

cct ctg aaa cac tct gac agc aaa gaa gat gat gga caa gaa ata gcc     1082
Pro Leu Lys His Ser Asp Ser Lys Glu Asp Asp Gly Gln Glu Ile Ala
                305                 310                 315

tgaccatgag gaccagggag ctgctacccc tccctacagc tcctaccctc tggctgcaat   1142

ggggctgcac tgtgagccct gcccccaaca gatgcatcct gctctgacag gtgggctcct   1202

tctccaaagg atgcgataca cagaccactg tgcagcctta tttctccaat ggacatgatt   1262

cccaagtcat cctgctgcct tttttcttat agacacaatg aacagaccac ccacaacctt   1322

agttctctaa gtcat                                                    1337


<210> SEQ ID NO 2
<211> LENGTH: 316
<212> TYPE: PRT
<213> ORGANISM: Homo sapiens

<400> SEQUENCE: 2

Met Leu Arg Arg Arg Gly Ser Pro Gly Met Gly Val His Val Gly Ala
  1               5                  10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175
```

-continued

```
Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315


<210> SEQ ID NO 3
<211> LENGTH: 1095
<212> TYPE: DNA
<213> ORGANISM: Mus musculus
<220> FEATURE:
<221> NAME/KEY: CDS
<222> LOCATION: (73)..(1020)

<400> SEQUENCE: 3

tggtaccgag ctcggatcca ctagtaacgg ccgccagtgt gctggaattc gcccttgctg      60

tctcacagga ag atg ctt cga gga tgg ggt ggc ccc agt gtg ggt gtg tgt     111
              Met Leu Arg Gly Trp Gly Gly Pro Ser Val Gly Val Cys
              1               5                   10

gtg cgc aca gca ctg ggg gtg ctg tgc ctc tgc ctc aca gga gct gtg       159
Val Arg Thr Ala Leu Gly Val Leu Cys Leu Cys Leu Thr Gly Ala Val
     15                  20                  25

gaa gtc cag gtc tct gaa gac ccc gtg gtg gcc ctg gtg gac acg gat       207
Glu Val Gln Val Ser Glu Asp Pro Val Val Ala Leu Val Asp Thr Asp
 30                  35                  40                  45

gcc acc cta cgc tgc tcc ttt tcc cca gag cct ggc ttc agt ctg gca       255
Ala Thr Leu Arg Cys Ser Phe Ser Pro Glu Pro Gly Phe Ser Leu Ala
                 50                  55                  60

cag ctc aac ctc atc tgg cag ctg aca gac acc aaa cag ctg gtg cac       303
Gln Leu Asn Leu Ile Trp Gln Leu Thr Asp Thr Lys Gln Leu Val His
             65                  70                  75

agc ttc acg gag ggc cgg gac caa ggc agt gcc tac tcc aac cgc aca       351
Ser Phe Thr Glu Gly Arg Asp Gln Gly Ser Ala Tyr Ser Asn Arg Thr
         80                  85                  90

gcg ctc ttc cct gac ctg ttg gtg caa ggc aat gcg tcc ttg agg ctg       399
Ala Leu Phe Pro Asp Leu Leu Val Gln Gly Asn Ala Ser Leu Arg Leu
     95                 100                 105

cag cgc gtc cga gta acc gac gag ggc agc tac acc tgc ttt gtg agc       447
Gln Arg Val Arg Val Thr Asp Glu Gly Ser Tyr Thr Cys Phe Val Ser
110                 115                 120                 125

atc cag gac ttt gac agc gct gct gtt agc ctg cag gtg gcc gcc ccc       495
Ile Gln Asp Phe Asp Ser Ala Ala Val Ser Leu Gln Val Ala Ala Pro
                130                 135                 140

tac tcg aag ccc agc atg acc ctg gag ccc aac aag gac cta cgt cca       543
Tyr Ser Lys Pro Ser Met Thr Leu Glu Pro Asn Lys Asp Leu Arg Pro
```

-continued

```
            145                 150                 155

ggg aac atg gtg acc atc acg tgc tct agc tac cag ggc tat ccg gag      591
Gly Asn Met Val Thr Ile Thr Cys Ser Ser Tyr Gln Gly Tyr Pro Glu
        160                 165                 170

gcc gag gtg ttc tgg aag gat gga cag gga gtg ccc ttg act ggc aat      639
Ala Glu Val Phe Trp Lys Asp Gly Gln Gly Val Pro Leu Thr Gly Asn
    175                 180                 185

gtg acc aca tcc cag atg gcc aac gag cgg ggc ttg ttc gat gtt cac      687
Val Thr Thr Ser Gln Met Ala Asn Glu Arg Gly Leu Phe Asp Val His
190                 195                 200                 205

agc gtg ctg agg gtg gtg ctg ggt gct aac ggc acc tac agc tgc ctg      735
Ser Val Leu Arg Val Val Leu Gly Ala Asn Gly Thr Tyr Ser Cys Leu
                210                 215                 220

gta cgc aac ccg gtg ttg cag caa gat gct cac ggc tca gtc acc atc      783
Val Arg Asn Pro Val Leu Gln Gln Asp Ala His Gly Ser Val Thr Ile
            225                 230                 235

aca ggg cag ccc ctg aca ttc ccc cct gag gct ctg tgg gta acc gtg      831
Thr Gly Gln Pro Leu Thr Phe Pro Pro Glu Ala Leu Trp Val Thr Val
        240                 245                 250

ggg ctc tct gtc tgt ctt gtg gta cta ctg gtg gcc ctg gct ttc gtg      879
Gly Leu Ser Val Cys Leu Val Val Leu Leu Val Ala Leu Ala Phe Val
    255                 260                 265

tgc tgg aga aag atc aag cag agc tgc gag gag gag aat gca ggt gcc      927
Cys Trp Arg Lys Ile Lys Gln Ser Cys Glu Glu Glu Asn Ala Gly Ala
270                 275                 280                 285

gag gac cag gat gga gat gga gaa gga tcc aag aca gct cta cgg cct      975
Glu Asp Gln Asp Gly Asp Gly Glu Gly Ser Lys Thr Ala Leu Arg Pro
                290                 295                 300

ctg aaa ccc tct gaa aac aaa gaa gat gac gga caa gaa att gct         1020
Leu Lys Pro Ser Glu Asn Lys Glu Asp Asp Gly Gln Glu Ile Ala
            305                 310                 315

tgattgggag ctgctgcaag ggcgaattct gcagatatcc atcacactgg cggccgctcg   1080

agcatgcatc tagag                                                    1095


<210> SEQ ID NO 4
<211> LENGTH: 316
<212> TYPE: PRT
<213> ORGANISM: Mus musculus

<400> SEQUENCE: 4

Met Leu Arg Gly Trp Gly Gly Pro Ser Val Gly Val Cys Val Arg Thr
  1               5                  10                  15

Ala Leu Gly Val Leu Cys Leu Cys Leu Thr Gly Ala Val Glu Val Gln
             20                  25                  30

Val Ser Glu Asp Pro Val Val Ala Leu Val Asp Thr Asp Ala Thr Leu
         35                  40                  45

Arg Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Thr
 65                  70                  75                  80

Glu Gly Arg Asp Gln Gly Ser Ala Tyr Ser Asn Arg Thr Ala Leu Phe
                 85                  90                  95

Pro Asp Leu Leu Val Gln Gly Asn Ala Ser Leu Arg Leu Gln Arg Val
            100                 105                 110

Arg Val Thr Asp Glu Gly Ser Tyr Thr Cys Phe Val Ser Ile Gln Asp
        115                 120                 125

Phe Asp Ser Ala Ala Val Ser Leu Gln Val Ala Ala Pro Tyr Ser Lys
```

-continued

```
    130                 135                 140

Pro Ser Met Thr Leu Glu Pro Asn Lys Asp Leu Arg Pro Gly Asn Met
145                 150                 155                 160

Val Thr Ile Thr Cys Ser Ser Tyr Gln Gly Tyr Pro Glu Ala Glu Val
                165                 170                 175

Phe Trp Lys Asp Gly Gln Gly Val Pro Leu Thr Gly Asn Val Thr Thr
            180                 185                 190

Ser Gln Met Ala Asn Glu Arg Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Leu Thr Phe Pro Pro Glu Ala Leu Trp Val Thr Val Gly Leu Ser
                245                 250                 255

Val Cys Leu Val Val Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Asp Gly Glu Gly Ser Lys Thr Ala Leu Arg Pro Leu Lys Pro
    290                 295                 300

Ser Glu Asn Lys Glu Asp Asp Gly Gln Glu Ile Ala
305                 310                 315


<210> SEQ ID NO 5
<211> LENGTH: 2797
<212> TYPE: DNA
<213> ORGANISM: Rattus norvegicus
<220> FEATURE:
<221> NAME/KEY: CDS
<222> LOCATION: (137)..(1084)

<400> SEQUENCE: 5

cctcgcggct gctctaccga cggtggcggc gattgtgctg cgccccgccg cgtccccgag      60

tcccgggagt cggcgcggcg cggcaggagc agccatccgc cacggagagt ccagctgtca     120

gctgtctcac aggaag atg ctt cga gga tgg ggt ggc ccc agt gtg ggt gtg     172
                  Met Leu Arg Gly Trp Gly Gly Pro Ser Val Gly Val
                  1               5                   10

tct atg ggc acg gca ctg gga gtg ttg tgc ctc tgc ctt aca gga gct       220
Ser Met Gly Thr Ala Leu Gly Val Leu Cys Leu Cys Leu Thr Gly Ala
        15                  20                  25

gtg gag gtc caa gtc tct gaa gac cct gtg gtg gcc cta gtg gat acg       268
Val Glu Val Gln Val Ser Glu Asp Pro Val Val Ala Leu Val Asp Thr
    30                  35                  40

gat gcc acc cta cgc tgc tcc ttc tcc cca gag cct ggc ttc agc ctg       316
Asp Ala Thr Leu Arg Cys Ser Phe Ser Pro Glu Pro Gly Phe Ser Leu
45                  50                  55                  60

aga cag ctc aac ctc atc tgg cag ctg aca gac acc aaa cag ctg gtg       364
Arg Gln Leu Asn Leu Ile Trp Gln Leu Thr Asp Thr Lys Gln Leu Val
                65                  70                  75

cac agc ttc act gag ggc cgg gac caa ggc agt gcc tat gcc aac cgc       412
His Ser Phe Thr Glu Gly Arg Asp Gln Gly Ser Ala Tyr Ala Asn Arg
            80                  85                  90

acg gcg ctc ttc cct gac ttg ttg gtg cag ggc aat gca tcc ctg agg       460
Thr Ala Leu Phe Pro Asp Leu Leu Val Gln Gly Asn Ala Ser Leu Arg
        95                  100                 105

ctg cag cgt gtc cga gta acc gac gag ggc agc tac acc tgc ttt gtg       508
```

-continued

```
Leu Gln Arg Val Arg Val Thr Asp Glu Gly Ser Tyr Thr Cys Phe Val
    110                 115                 120

agc atc cag gac ttt gac agc gct gct gtt agc ctg cag gtg gcc gcc      556
Ser Ile Gln Asp Phe Asp Ser Ala Ala Val Ser Leu Gln Val Ala Ala
125                 130                 135                 140

ccc tac tca aag ccc agc atg acc ctg gag ccc aac aag gac ctg cgt      604
Pro Tyr Ser Lys Pro Ser Met Thr Leu Glu Pro Asn Lys Asp Leu Arg
                145                 150                 155

cca ggg gac atg gtg acc atc acg tgc tcc agc tac cag ggc tat ccc      652
Pro Gly Asp Met Val Thr Ile Thr Cys Ser Ser Tyr Gln Gly Tyr Pro
            160                 165                 170

gag gct gag gtg ttc tgg aag gac gga cag gga ttg ccc ttg act ggc      700
Glu Ala Glu Val Phe Trp Lys Asp Gly Gln Gly Leu Pro Leu Thr Gly
        175                 180                 185

aat gtg acc aca tcc cag atg gcc aac gag cgg ggc ctg ttc gat gtt      748
Asn Val Thr Thr Ser Gln Met Ala Asn Glu Arg Gly Leu Phe Asp Val
    190                 195                 200

cac agt gtg ctg agg gtg gtg ctg ggt gct aat ggc acc tac agc tgc      796
His Ser Val Leu Arg Val Val Leu Gly Ala Asn Gly Thr Tyr Ser Cys
205                 210                 215                 220

ctg gtc cgc aac ccg gtg ttg cag caa gat gct cat ggc tcg gtc acc      844
Leu Val Arg Asn Pro Val Leu Gln Gln Asp Ala His Gly Ser Val Thr
                225                 230                 235

atc aca ggg cag ccc atg aca ttc ccc cct gag gct cta tgg gtg act      892
Ile Thr Gly Gln Pro Met Thr Phe Pro Pro Glu Ala Leu Trp Val Thr
            240                 245                 250

gtg ggg ctc tct gtc tgt ctt gtg ata ctg ctg gtg gcc ctg gcc ttc      940
Val Gly Leu Ser Val Cys Leu Val Ile Leu Leu Val Ala Leu Ala Phe
        255                 260                 265

gtg tgc tgg aga aag atc aag cag agc tgt gaa gag gag aat gca ggt      988
Val Cys Trp Arg Lys Ile Lys Gln Ser Cys Glu Glu Glu Asn Ala Gly
    270                 275                 280

gct gag gac cag gat ggg gat gga gaa gga tcc aag aca gct ctt cgg     1036
Ala Glu Asp Gln Asp Gly Asp Gly Glu Gly Ser Lys Thr Ala Leu Arg
285                 290                 295                 300

cct ctg aaa cac tct gaa aac aaa gaa gat gac gga caa gaa ata gct     1084
Pro Leu Lys His Ser Glu Asn Lys Glu Asp Asp Gly Gln Glu Ile Ala
                305                 310                 315

tgactggaag ctgctgccct tccctggtgg gggggcccac cctctggctg tattgagcct   1144

caatgtgagc cctgccccca atgaatgggt tttgttccac agatctaccc attctttaga   1204

ggacgtggtt tacaggctac ccacagcctt attttcccaa tggacttaat tcccatcatc   1264

ctgaagcctc ctttctccag tgacacgata cacgaaccat cctgcggcct tatttcttac   1324

ggactcgaca caaagagttc tccacctcag tgtccctcca gagtcatccg gtggccttgt   1384

gatactacac ggaccttcct tctgccttac tttaatagat atacacaaac catccccatg   1444

tccttgtgcc tccaaagcca tgcagagact gtattactgc tactattctc caaggcacat   1504

gctattcaga tgaacccctg ccttattcct ctgaagacag atgcttagtt acctcttggt   1564

tctttctccc atggccctga catatcttag tcacccatca acgatgggat cccatctctc   1624

agcaagtcct caacctgact ccctgccctc atctggccct ggctttggtt ttctccctcc   1684

ctaagtgaga tggggcacac tccccatcca cacacatggg tcacagctgt gcgtgctgga   1744

tcgcgtacat acttgccttg catggtctcc tctggctgcc ctgggctgtg ccctttctcg   1804

cctcaggaag caggtgctgg tcggcctggt tctcagggcc cctcagggag tcagccttca   1864

accctgtgct tcccgtgttg gaaatctttg ttacttttcc tttcttagta aattaacatc   1924
```

-continued

```
tgttgaacaa ccacagcgtc caacaggact ttcacagacc ctgccagcta gattaaataa   1984

tgatacagaa gtttattaat tattttaaag cttaggtttt tttgccggga ggtatcccaa   2044

atactctatc ccgactaatc ctggcactat gtcccaccac atggccaggc ctacctctgc   2104

tccactctga atcatccacc tctgtgtccg ccgacaaatc tcccatgatt cagttcttct   2164

cccagcgtcc ctatctctgc ccggaagtac gacctttgac ttcctgacca actattggcc   2224

gtcaactctt tgttaaaggt gatcagatat aattttgcct taggcacgtg aggaagaaac   2284

atatttataa aatacgagac cagagatggg ccatggaaat aacaccagat tctgacagcc   2344

tttagccctc tgctggtaca aattaacaat tgaatatata gagacacacc ttcacacagt   2404

gcaccccaac aacaggggtg agcattgtgc tgggtactag ggtcctgctg aaatcagaga   2464

ccttaactcc agctggggaa tggccttgct ccctgctgtg cccacagctt ccaacactgt   2524

ccctgacccc agggtagggg tggaaacctg gagaaggcac agccccttac cataccttga   2584

gaactgggta tttttcagag tctatatgtg tgcactggaa ggcaggtggc cacagccatg   2644

cagacctggg tagggtcaga agcctatgcc acgctgggac ctcctcaaca gctgaagtct   2704

gaggacaaga agggccttct tactgtggtg ctattctgga gctggggtat atacctggct   2764

tgtctctgac agccctggct tttggcagaa ctt                                2797


<210> SEQ ID NO 6
<211> LENGTH: 316
<212> TYPE: PRT
<213> ORGANISM: Rattus norvegicus

<400> SEQUENCE: 6

Met Leu Arg Gly Trp Gly Gly Pro Ser Val Gly Val Ser Met Gly Thr
1               5                   10                  15

Ala Leu Gly Val Leu Cys Leu Cys Leu Thr Gly Ala Val Glu Val Gln
            20                  25                  30

Val Ser Glu Asp Pro Val Val Ala Leu Val Asp Thr Asp Ala Thr Leu
        35                  40                  45

Arg Cys Ser Phe Ser Pro Glu Pro Gly Phe Ser Leu Arg Gln Leu Asn
    50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ala Asn Arg Thr Ala Leu Phe
                85                  90                  95

Pro Asp Leu Leu Val Gln Gly Asn Ala Ser Leu Arg Leu Gln Arg Val
            100                 105                 110

Arg Val Thr Asp Glu Gly Ser Tyr Thr Cys Phe Val Ser Ile Gln Asp
        115                 120                 125

Phe Asp Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Met
145                 150                 155                 160

Val Thr Ile Thr Cys Ser Ser Tyr Gln Gly Tyr Pro Glu Ala Glu Val
                165                 170                 175

Phe Trp Lys Asp Gly Gln Gly Leu Pro Leu Thr Gly Asn Val Thr Thr
            180                 185                 190

Ser Gln Met Ala Asn Glu Arg Gly Leu Phe Asp Val His Ser Val Leu
        195                 200                 205

Arg Val Val Leu Gly Ala Asn Gly Thr Tyr Ser Cys Leu Val Arg Asn
    210                 215                 220
```

-continued

```
Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Val Ile Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Asp Gly Glu Gly Ser Lys Thr Ala Leu Arg Pro Leu Lys His
    290                 295                 300

Ser Glu Asn Lys Glu Asp Asp Gly Gln Glu Ile Ala
305                 310                 315


<210> SEQ ID NO 7
<211> LENGTH: 526
<212> TYPE: PRT
<213> ORGANISM: Homo sapiens

<400> SEQUENCE: 7

Met Ala Val Phe Pro Ser Ser Gly Leu Pro Arg Cys Leu Leu Thr Leu
  1               5                  10                  15

Ile Leu Leu Gln Leu Pro Lys Leu Asp Ser Ala Pro Phe Asp Val Ile
             20                  25                  30

Gly Pro Pro Glu Pro Ile Leu Ala Val Val Gly Glu Asp Ala Glu Leu
         35                  40                  45

Pro Cys Arg Leu Ser Pro Asn Ala Ser Ala Glu His Leu Glu Leu Arg
     50                  55                  60

Trp Phe Arg Lys Lys Val Ser Pro Ala Val Leu Val His Arg Asp Gly
 65                  70                  75                  80

Arg Glu Gln Glu Ala Glu Gln Met Pro Glu Tyr Arg Gly Arg Ala Thr
                 85                  90                  95

Leu Val Gln Asp Gly Ile Ala Lys Gly Arg Val Ala Leu Arg Ile Arg
            100                 105                 110

Gly Val Arg Val Ser Asp Asp Gly Glu Tyr Thr Cys Phe Phe Arg Glu
        115                 120                 125

Asp Gly Ser Tyr Glu Glu Ala Leu Val His Leu Lys Val Ala Ala Leu
    130                 135                 140

Gly Ser Asp Pro His Ile Ser Met Gln Val Gln Glu Asn Gly Glu Ile
145                 150                 155                 160

Cys Leu Glu Cys Thr Ser Val Gly Trp Tyr Pro Glu Pro Gln Val Gln
                165                 170                 175

Trp Arg Thr Ser Lys Gly Glu Lys Phe Pro Ser Thr Ser Glu Ser Arg
            180                 185                 190

Asn Pro Asp Glu Glu Gly Leu Phe Thr Val Ala Ala Ser Val Ile Ile
        195                 200                 205

Arg Asp Thr Ser Thr Lys Asn Val Ser Cys Tyr Ile Gln Asn Leu Leu
    210                 215                 220

Leu Gly Gln Glu Lys Lys Val Glu Ile Ser Ile Pro Ala Ser Ser Leu
225                 230                 235                 240

Pro Arg Leu Thr Pro Trp Ile Val Ala Val Ala Val Ile Leu Met Val
                245                 250                 255

Leu Gly Leu Leu Thr Ile Gly Ser Ile Phe Phe Thr Trp Arg Leu Tyr
            260                 265                 270

Asn Glu Arg Pro Arg Glu Arg Arg Asn Glu Phe Ser Ser Lys Glu Arg
```

-continued

```
        275                 280                 285

Leu Leu Glu Glu Leu Lys Trp Lys Lys Ala Thr Leu His Ala Val Asp
    290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
                325                 330                 335

Lys Thr Glu Arg Phe Asp Ser Trp Pro Cys Val Leu Gly Arg Glu Thr
            340                 345                 350

Phe Thr Ser Gly Arg His Tyr Trp Glu Val Glu Val Gly Asp Arg Thr
        355                 360                 365

Asp Trp Ala Ile Gly Val Cys Arg Glu Asn Val Met Lys Lys Gly Phe
    370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
                405                 410                 415

Gly Pro Pro Arg Arg Val Gly Ile Phe Leu Asp Tyr Glu Ser Gly Asp
            420                 425                 430

Ile Ser Phe Tyr Asn Met Asn Asp Gly Ser Asp Ile Tyr Thr Phe Ser
        435                 440                 445

Asn Val Thr Phe Ser Gly Pro Leu Arg Pro Phe Phe Cys Leu Trp Ser
    450                 455                 460

Ser Gly Lys Lys Pro Leu Thr Ile Cys Pro Ile Ala Asp Gly Pro Glu
465                 470                 475                 480

Arg Val Thr Val Ile Ala Asn Ala Gln Asp Leu Ser Lys Glu Ile Pro
                485                 490                 495

Leu Ser Pro Met Gly Glu Glu Ser Ala Pro Arg Asp Ala Asp Thr Leu
            500                 505                 510

His Ser Lys Leu Ile Pro Thr Gln Pro Ser Gln Gly Ala Pro
        515                 520                 525


<210> SEQ ID NO 8
<211> LENGTH: 526
<212> TYPE: PRT
<213> ORGANISM: Bos taurus

<400> SEQUENCE: 8

Met Ala Val Phe Pro Asn Ser Cys Leu Ala Gly Cys Leu Leu Ile Phe
  1               5                  10                  15

Ile Leu Leu Gln Leu Pro Lys Leu Asp Ser Ala Pro Phe Asp Val Ile
             20                  25                  30

Gly Pro Gln Glu Pro Ile Leu Ala Val Val Gly Glu Asp Ala Glu Leu
         35                  40                  45

Pro Cys Arg Leu Ser Pro Asn Val Ser Ala Lys Gly Met Glu Leu Arg
     50                  55                  60

Trp Phe Arg Glu Lys Val Ser Pro Ala Val Phe Val Ser Arg Glu Gly
 65                  70                  75                  80

Gln Glu Gln Glu Gly Glu Glu Met Ala Glu Tyr Arg Gly Arg Val Ser
                 85                  90                  95

Leu Val Glu Asp His Ile Ala Glu Gly Ser Val Ala Val Arg Ile Gln
            100                 105                 110

Glu Val Lys Ala Ser Asp Asp Gly Glu Tyr Arg Cys Phe Phe Arg Gln
        115                 120                 125
```

-continued

```
Asp Glu Asn Tyr Glu Glu Ala Ile Val His Leu Lys Val Ala Ala Leu
    130                 135                 140

Gly Ser Asp Pro His Ile Ser Met Lys Val Gln Glu Ser Gly Glu Ile
145                 150                 155                 160

Gln Leu Glu Cys Thr Ser Val Gly Trp Tyr Pro Glu Pro Gln Val Gln
                165                 170                 175

Trp Arg Thr His Arg Gly Glu Glu Phe Pro Ser Met Ser Glu Ser Arg
            180                 185                 190

Asn Pro Asp Glu Glu Gly Leu Phe Thr Val Arg Ala Ser Val Ile Ile
        195                 200                 205

Arg Asp Ser Ser Met Lys Asn Val Ser Cys Cys Ile Arg Asn Leu Leu
    210                 215                 220

Leu Gly Gln Glu Lys Glu Val Glu Val Ser Ile Pro Ala Ser Phe Phe
225                 230                 235                 240

Pro Arg Leu Thr Pro Trp Met Val Ala Val Ala Val Ile Leu Val Val
                245                 250                 255

Leu Gly Leu Leu Thr Ile Gly Ser Ile Phe Phe Thr Trp Arg Leu Tyr
            260                 265                 270

Lys Glu Arg Ser Arg Gln Arg Arg Asn Glu Phe Ser Ser Lys Glu Lys
        275                 280                 285

Leu Leu Glu Glu Leu Lys Trp Lys Arg Ala Thr Leu His Ala Val Asp
    290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
                325                 330                 335

Lys Pro Glu Arg Phe Asp Ser Trp Pro Cys Val Met Gly Arg Glu Ala
            340                 345                 350

Phe Thr Ser Gly Arg His Tyr Trp Glu Val Glu Val Gly Asp Arg Thr
        355                 360                 365

Asp Trp Ala Ile Gly Val Cys Arg Glu Asn Val Met Lys Lys Gly Phe
    370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
                405                 410                 415

Gly Pro Pro Arg Arg Val Gly Val Phe Leu Asp Tyr Glu Ser Gly Asp
            420                 425                 430

Ile Phe Phe Tyr Asn Met Thr Asp Gly Ser His Ile Tyr Thr Phe Ser
        435                 440                 445

Lys Ala Ser Phe Ser Gly Pro Leu Arg Pro Phe Phe Cys Leu Trp Ser
    450                 455                 460

Cys Gly Lys Lys Pro Leu Thr Ile Cys Pro Val Thr Asp Gly Leu Glu
465                 470                 475                 480

Gly Val Met Val Val Ala Asp Ala Lys Asp Ile Ser Lys Glu Ile Pro
                485                 490                 495

Leu Ser Pro Met Gly Glu Asp Ser Ala Ser Gly Asp Ile Glu Thr Leu
            500                 505                 510

His Ser Lys Leu Ile Pro Leu Gln Pro Ser Gln Gly Val Pro
        515                 520                 525
```

<210> SEQ ID NO 9
<211> LENGTH: 524
<212> TYPE: PRT

-continued

<213> ORGANISM: Mus musculus

<400> SEQUENCE: 9

```
Met Ala Val Pro Thr Asn Ser Cys Leu Leu Val Cys Leu Leu Thr Leu
  1               5                  10                  15

Thr Val Leu Gln Leu Pro Thr Leu Asp Ser Ala Ala Pro Phe Asp Val
             20                  25                  30

Thr Ala Pro Gln Glu Pro Val Leu Ala Leu Val Gly Ser Asp Ala Glu
         35                  40                  45

Leu Thr Cys Gly Phe Ser Pro Asn Ala Ser Ser Glu Tyr Met Glu Leu
     50                  55                  60

Leu Trp Phe Arg Gln Thr Arg Ser Thr Ala Val Leu Leu Tyr Arg Asp
 65                  70                  75                  80

Gly Gln Glu Gln Glu Gly Gln Gln Met Thr Glu Tyr Arg Gly Arg Ala
                 85                  90                  95

Thr Leu Ala Thr Ala Gly Leu Leu Asp Gly Arg Ala Thr Leu Leu Ile
            100                 105                 110

Arg Asp Val Arg Val Ser Asp Gln Gly Glu Tyr Arg Cys Leu Phe Lys
        115                 120                 125

Asp Asn Asp Asp Phe Glu Glu Ala Ala Val Tyr Leu Lys Val Ala Ala
    130                 135                 140

Val Gly Ser Asp Pro Gln Ile Ser Met Thr Val Gln Glu Asn Gly Glu
145                 150                 155                 160

Met Glu Leu Glu Cys Thr Ser Ser Gly Trp Tyr Pro Glu Pro Gln Val
                165                 170                 175

Gln Trp Arg Thr Gly Asn Arg Glu Met Leu Pro Ser Thr Ser Glu Ser
            180                 185                 190

Lys Lys His Asn Glu Glu Gly Leu Phe Thr Val Ala Val Ser Met Met
        195                 200                 205

Ile Arg Asp Ser Ser Ile Lys Asn Met Ser Cys Cys Ile Gln Asn Ile
    210                 215                 220

Leu Leu Gly Gln Gly Lys Glu Val Glu Ile Ser Leu Pro Ala Pro Phe
225                 230                 235                 240

Val Pro Arg Leu Thr Pro Trp Ile Val Ala Val Ala Ile Ile Leu Leu
                245                 250                 255

Ala Leu Gly Phe Leu Thr Ile Gly Ser Ile Phe Phe Thr Trp Lys Leu
            260                 265                 270

Tyr Lys Glu Arg Ser Ser Leu Arg Lys Lys Glu Phe Gly Ser Lys Glu
        275                 280                 285

Arg Leu Leu Glu Glu Leu Arg Cys Lys Lys Thr Val Leu His Glu Val
    290                 295                 300

Asp Val Thr Leu Asp Pro Asp Thr Ala His Pro His Leu Phe Leu Tyr
305                 310                 315                 320

Glu Asp Ser Lys Ser Val Arg Leu Glu Asp Ser Arg Gln Ile Leu Pro
                325                 330                 335

Asp Arg Pro Glu Arg Phe Asp Ser Trp Pro Cys Val Leu Gly Arg Glu
            340                 345                 350

Thr Phe Thr Ser Gly Arg His Tyr Trp Glu Val Glu Val Gly Asp Arg
        355                 360                 365

Thr Asp Trp Ala Ile Gly Val Cys Arg Glu Asn Val Val Lys Lys Gly
    370                 375                 380

Phe Asp Pro Met Thr Pro Asp Asn Gly Phe Trp Ala Val Glu Leu Tyr
385                 390                 395                 400
```

-continued

```
Gly Asn Gly Tyr Trp Ala Leu Thr Pro Leu Arg Thr Ser Leu Arg Leu
                405                 410                 415

Ala Gly Pro Pro Arg Arg Val Gly Val Phe Leu Asp Tyr Asp Ala Gly
            420                 425                 430

Asp Ile Ser Phe Tyr Asn Met Ser Asn Gly Ser Leu Ile Tyr Thr Phe
        435                 440                 445

Pro Ser Ile Ser Phe Ser Gly Pro Leu Arg Pro Phe Phe Cys Leu Trp
    450                 455                 460

Ser Cys Gly Lys Lys Pro Leu Thr Ile Cys Ser Thr Ala Asn Gly Pro
465                 470                 475                 480

Glu Lys Val Thr Val Ile Ala Asn Val Gln Asp Asp Ile Pro Leu Ser
                485                 490                 495

Pro Leu Gly Glu Gly Cys Thr Ser Gly Asp Lys Asp Thr Leu His Ser
            500                 505                 510

Lys Leu Ile Pro Phe Ser Pro Ser Gln Ala Ala Pro
        515                 520


<210> SEQ ID NO 10
<211> LENGTH: 527
<212> TYPE: PRT
<213> ORGANISM: Homo sapiens

<400> SEQUENCE: 10

Met Glu Ser Ala Ala Ala Leu His Phe Ser Arg Pro Ala Ser Leu Leu
  1               5                  10                  15

Leu Leu Leu Leu Ser Leu Cys Ala Leu Val Ser Ala Gln Phe Ile Val
            20                  25                  30

Val Gly Pro Thr Asp Pro Ile Leu Ala Thr Val Gly Glu Asn Thr Thr
        35                  40                  45

Leu Arg Cys His Leu Ser Pro Glu Lys Asn Ala Glu Asp Met Glu Val
     50                  55                  60

Arg Trp Phe Arg Ser Gln Phe Ser Pro Ala Val Phe Val Tyr Lys Gly
 65                  70                  75                  80

Gly Arg Glu Arg Thr Glu Glu Gln Met Glu Glu Tyr Arg Gly Arg Thr
                 85                  90                  95

Thr Phe Val Ser Lys Asp Ile Ser Arg Gly Ser Val Ala Leu Val Ile
            100                 105                 110

His Asn Ile Thr Ala Gln Glu Asn Gly Thr Tyr Arg Cys Tyr Phe Gln
        115                 120                 125

Glu Gly Arg Ser Tyr Asp Glu Ala Ile Leu His Leu Val Val Ala Gly
    130                 135                 140

Leu Gly Ser Lys Pro Leu Ile Ser Met Arg Gly His Glu Asp Gly Gly
145                 150                 155                 160

Ile Arg Leu Glu Cys Ile Ser Arg Gly Trp Tyr Pro Lys Pro Leu Thr
                165                 170                 175

Val Trp Arg Asp Pro Tyr Gly Gly Val Ala Pro Ala Leu Lys Glu Val
            180                 185                 190

Ser Met Pro Asp Ala Asp Gly Leu Phe Met Val Thr Thr Ala Val Ile
        195                 200                 205

Ile Arg Asp Lys Ser Val Arg Asn Met Ser Cys Ser Ile Asn Asn Thr
    210                 215                 220

Leu Leu Gly Gln Lys Lys Glu Ser Val Ile Phe Ile Pro Glu Ser Phe
225                 230                 235                 240

Met Pro Ser Val Ser Pro Cys Ala Val Ala Leu Pro Ile Ile Val Val
                245                 250                 255
```

-continued

Ile Leu Met Ile Pro Ile Ala Val Cys Ile Tyr Trp Ile Asn Lys Leu
260 265 270

Gln Lys Glu Lys Lys Ile Leu Ser Gly Glu Lys Glu Phe Glu Arg Glu
275 280 285

Thr Arg Glu Ile Ala Leu Lys Glu Leu Glu Lys Glu Arg Val Gln Lys
290 295 300

Glu Glu Glu Leu Gln Val Lys Glu Lys Leu Gln Glu Glu Leu Arg Trp
305 310 315 320

Arg Arg Thr Phe Leu His Ala Val Asp Val Val Leu Asp Pro Asp Thr
325 330 335

Ala His Pro Asp Leu Phe Leu Ser Glu Asp Arg Arg Ser Val Arg Arg
340 345 350

Cys Pro Phe Arg His Leu Gly Glu Ser Val Pro Asp Asn Pro Glu Arg
355 360 365

Phe Asp Ser Gln Pro Cys Val Leu Gly Arg Glu Ser Phe Ala Ser Gly
370 375 380

Lys His Tyr Trp Glu Val Glu Val Glu Asn Val Ile Glu Trp Thr Val
385 390 395 400

Gly Val Cys Arg Asp Ser Val Glu Arg Lys Gly Glu Val Leu Leu Ile
405 410 415

Pro Gln Asn Gly Phe Trp Thr Leu Glu Met His Lys Gly Gln Tyr Arg
420 425 430

Ala Val Ser Ser Pro Asp Arg Ile Leu Pro Leu Lys Glu Ser Leu Cys
435 440 445

Arg Val Gly Val Phe Leu Asp Tyr Glu Ala Gly Asp Val Ser Phe Tyr
450 455 460

Asn Met Arg Asp Arg Ser His Ile Tyr Thr Cys Pro Arg Ser Ala Phe
465 470 475 480

Ser Val Pro Val Arg Pro Phe Phe Arg Leu Gly Cys Glu Asp Ser Pro
485 490 495

Ile Phe Ile Cys Pro Ala Leu Thr Gly Ala Asn Gly Val Thr Val Pro
500 505 510

Glu Glu Gly Leu Thr Leu His Arg Val Gly Thr His Gln Ser Leu
515 520 525

<210> SEQ ID NO 11
<211> LENGTH: 359
<212> TYPE: PRT
<213> ORGANISM: Homo sapiens

<400> SEQUENCE: 11

Met Lys Met Ala Ser Ser Leu Ala Phe Leu Leu Leu Asn Phe His Val
1 5 10 15

Ser Leu Leu Leu Val Gln Leu Leu Thr Pro Cys Ser Ala Gln Phe Ser
20 25 30

Val Leu Gly Pro Ser Gly Pro Ile Leu Ala Met Val Gly Glu Asp Ala
35 40 45

Asp Leu Pro Cys His Leu Phe Pro Thr Met Ser Ala Glu Thr Met Glu
50 55 60

Leu Lys Trp Val Ser Ser Ser Leu Arg Gln Val Val Asn Val Tyr Ala
65 70 75 80

Asp Gly Lys Glu Val Glu Asp Arg Gln Ser Ala Pro Tyr Arg Gly Arg
85 90 95

Thr Ser Ile Leu Arg Asp Gly Ile Thr Ala Gly Lys Ala Ala Leu Arg

-continued

```
            100                 105                 110

Ile His Asn Val Thr Ala Ser Asp Ser Gly Lys Tyr Leu Cys Tyr Phe
        115                 120                 125

Gln Asp Gly Asp Phe Tyr Glu Lys Ala Leu Val Glu Leu Lys Val Ala
    130                 135                 140

Ala Leu Gly Ser Asn Leu His Val Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175

Ile Gln Trp Ser Asn Ala Lys Gly Glu Asn Ile Pro Ala Val Glu Ala
            180                 185                 190

Pro Val Val Ala Asp Gly Val Gly Leu Tyr Glu Val Ala Ala Ser Val
        195                 200                 205

Ile Met Arg Gly Gly Ser Gly Glu Gly Val Ser Cys Ile Ile Arg Asn
    210                 215                 220

Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
                245                 250                 255

Pro Ile Leu Leu Leu Leu Leu Ala Gly Ala Ser Tyr Phe Leu Trp Arg
            260                 265                 270

Gln Gln Lys Glu Ile Thr Ala Leu Ser Ser Glu Ile Glu Ser Glu Gln
        275                 280                 285

Glu Met Lys Glu Met Gly Tyr Ala Ala Thr Glu Arg Glu Ile Ser Leu
    290                 295                 300

Arg Glu Ser Leu Gln Glu Glu Leu Lys Arg Lys Lys Ile Gln Tyr Leu
305                 310                 315                 320

Thr Arg Gly Glu Glu Ser Ser Ser Asp Thr Asn Lys Ser Ala Leu Met
                325                 330                 335

Leu Lys Trp Lys Lys Ala Leu Leu Lys Pro Gly Glu Glu Met Leu Gln
            340                 345                 350

Met Arg Leu His Leu Val Lys
        355


<210> SEQ ID NO 12
<211> LENGTH: 319
<212> TYPE: PRT
<213> ORGANISM: Homo sapiens

<400> SEQUENCE: 12

Met Lys Met Ala Ser Ser Leu Ala Phe Leu Leu Leu Asn Phe His Val
  1               5                  10                  15

Ser Leu Leu Leu Val Gln Leu Leu Thr Pro Cys Ser Ala Gln Phe Ser
             20                  25                  30

Val Leu Gly Pro Ser Gly Pro Ile Leu Ala Met Val Gly Glu Asp Ala
         35                  40                  45

Asp Leu Pro Cys His Leu Phe Pro Thr Met Ser Ala Glu Thr Met Glu
     50                  55                  60

Leu Lys Trp Val Ser Ser Ser Leu Arg Gln Val Val Asn Val Tyr Ala
 65                  70                  75                  80

Asp Gly Lys Glu Val Glu Asp Arg Gln Ser Ala Pro Tyr Arg Gly Arg
                 85                  90                  95

Thr Ser Ile Leu Arg Asp Gly Ile Thr Ala Gly Lys Ala Ala Leu Arg
            100                 105                 110
```

-continued

```
Ile His Asn Val Thr Ala Ser Asp Ser Gly Lys Tyr Leu Cys Tyr Phe
        115                 120                 125

Gln Asp Gly Asp Phe Tyr Glu Lys Ala Leu Val Glu Leu Lys Val Ala
    130                 135                 140

Ala Leu Gly Ser Asn Leu His Val Glu Val Lys Gly Tyr Glu Asp Gly
145                 150                 155                 160

Gly Ile His Leu Glu Cys Arg Ser Thr Gly Trp Tyr Pro Gln Pro Gln
                165                 170                 175

Ile Gln Trp Ser Asn Ala Lys Gly Glu Asn Ile Pro Ala Val Glu Ala
            180                 185                 190

Pro Val Val Ala Asp Gly Val Gly Leu Tyr Glu Val Ala Ala Ser Val
        195                 200                 205

Ile Met Arg Gly Gly Ser Gly Glu Gly Val Ser Cys Ile Ile Arg Asn
    210                 215                 220

Ser Leu Leu Gly Leu Glu Lys Thr Ala Ser Ile Ser Ile Ala Asp Pro
225                 230                 235                 240

Phe Phe Arg Ser Ala Gln Pro Trp Ile Ala Ala Leu Ala Gly Thr Leu
                245                 250                 255

Pro Ile Leu Leu Leu Leu Leu Ala Gly Ala Ser Tyr Phe Leu Trp Arg
            260                 265                 270

Gln Gln Lys Glu Ile Thr Ala Leu Ser Ser Glu Ile Glu Ser Glu Gln
        275                 280                 285

Glu Met Lys Glu Met Gly Tyr Ala Ala Thr Glu Arg Glu Ile Ser Leu
    290                 295                 300

Arg Glu Ser Leu Gln Glu Glu Leu Lys Arg Lys Lys Ser Ser Thr
305                 310                 315


<210> SEQ ID NO 13
<211> LENGTH: 280
<212> TYPE: PRT
<213> ORGANISM: Grus americana

<400> SEQUENCE: 13

Met Gln Met Trp Leu Pro Ala Ser Pro Arg Gly Leu Leu Ser Tyr Leu
  1               5                  10                  15

Val Thr Leu His Val Leu Arg Leu Gly Ser Ala Asn Phe Ser Val Val
            20                  25                  30

Gly Pro Gly His Pro Leu Arg Val Thr Val Gly Gln Asp Val Met Leu
        35                  40                  45

Pro Cys His Leu Ser Pro Ser Met Glu Ala Arg Ser Leu Asp Ile Arg
     50                  55                  60

Trp Ile Arg His Gln Val Ser Glu Ile Val His Arg Tyr Arg Asn Gly
 65                  70                  75                  80

Glu Asp Leu Tyr Gly Asp Gln Met Glu Glu Tyr Val Gly Arg Thr Glu
                 85                  90                  95

Leu Val Arg Asp Gly Leu Ser Arg Gly Arg Leu Asp Leu Arg Ile Ser
            100                 105                 110

Gly Leu Arg Pro Ser Asp Asp Gly Gln Tyr Val Cys Thr Val Arg Asp
        115                 120                 125

Gly Ser Ser Tyr Gly Glu Ala Thr Val Asp Leu Glu Val Ser Ala Thr
    130                 135                 140

Gly Ser Gly Pro Gln Leu Ser Leu Glu Ala Tyr Glu Asp Gly Gly Ile
145                 150                 155                 160

Arg Val Val Cys Arg Ser Ala Gly Trp Tyr Pro Arg Pro Glu Val Leu
                165                 170                 175
```

-continued

```
Trp Lys Asp Pro Gly Gly Gln His Leu Pro Ser Val Ser Gln Arg Tyr
            180                 185                 190

Ser Phe Asp Glu Arg Gly Leu Phe Asp Thr Glu Asp Val Ile Ile Val
        195                 200                 205

Thr Asp Gly Asn Arg Asp Gly Lys Trp Ser Cys Val Val Arg Asn Ser
    210                 215                 220

His Leu Asn Gln Glu Gln Glu Thr Ser Leu His Ile Ser Ala Pro Phe
225                 230                 235                 240

Phe His Asn Ala Arg Pro Trp Met Val Gly Val Gln Val Leu Leu Val
                245                 250                 255

Leu Ser Gly Val Leu Leu Gly Leu Gly Ala Tyr Leu Trp Arg Arg Lys
            260                 265                 270

Val Leu Gln Ser Arg Glu Leu Glu
        275                 280


<210> SEQ ID NO 14
<211> LENGTH: 11
<212> TYPE: PRT
<213> ORGANISM: Human immunodeficiency virus type 1

<400> SEQUENCE: 14

Tyr Gly Arg Lys Lys Arg Arg Gln Arg Arg Arg
  1               5                  10


<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:
      internalizing domain derived from HIV tat protein

<400> SEQUENCE: 15

Gly Gly Gly Gly Tyr Gly Arg Lys Lys Arg Arg Gln Arg Arg Arg
  1               5                  10                  15


<210> SEQ ID NO 16
<211> LENGTH: 792
<212> TYPE: DNA
<213> ORGANISM: Homo sapiens
<220> FEATURE:
<221> NAME/KEY: unsure
<222> LOCATION: (125)
<223> OTHER INFORMATION: "n" is a, g, c, or t
<220> FEATURE:
<221> NAME/KEY: unsure
<222> LOCATION: (128)
<223> OTHER INFORMATION: "n" is a, g, c, or t
<220> FEATURE:
<221> NAME/KEY: unsure
<222> LOCATION: (137)
<223> OTHER INFORMATION: "n" is a, g, c, or t
<220> FEATURE:
<221> NAME/KEY: unsure
<222> LOCATION: (692)
<223> OTHER INFORMATION: "n" is a, g, c, or t
<220> FEATURE:
<221> NAME/KEY: unsure
<222> LOCATION: (716)
<223> OTHER INFORMATION: "n" is a, g, c, or t
<220> FEATURE:
<221> NAME/KEY: unsure
<222> LOCATION: (762)
<223> OTHER INFORMATION: "n" is a, g, c, or t
<220> FEATURE:
<221> NAME/KEY: unsure
<222> LOCATION: (787)
```

-continued

<223> OTHER INFORMATION: "n" is a, g, c, or t

<400> SEQUENCE: 16
tctggcagga tgggcagggt gtgcccatga ctggcaacgt gaccacgtcg cagatggcca 60
acgagcaggg cttgtttgat gtgcacagcg tcctgcgggt ggtgctgggt gcgaatggca 120
ctacngcntg cctgttncgc aaccccgtgc tgcagcagga tgcgcacggc tctgtcacca 180
tcacagggca gcctatgaca ttccccccag aggccctgtg gtgaccgtgg ggctgtctgt 240
ctgtctcatt gcactgctgg tggccctggc tttcgtgtgc tggagaaaga tcaaacagag 300
ctgtgaggag gagaatgcag gagctgagga ccaggatggg gagggagaag gctccaagac 360
agccctgcag cctctgaaac actctgacag caaagaagat gatggacaag aaatagcctg 420
accatgagga ccagggagct gctacccctc cctacagctc ctaccctctg gctgcaatgg 480
ggctgcactg tgagccctgc ccccaacaga tgcatcctgc tctgacaggt gggctccttc 540
tccaaaggat gcgatacaca gaccactgtg cagccttatt tctccaatgg acatgattcc 600
caagtcatcc tgctgccttt tttcttatag acacaatgaa cagaccaccc acaaccttga 660
gttctgtaaa gtcatcctgg cctgctggcc tntattttca cagttacata catttnttta 720
gggggacaca gttacattga accacattta accacctttt tnttttccag ttgttgcgtg 780
gggaccnttt gg 792

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
oligonucleotide; PCR primer 2245-71

<400> SEQUENCE: 17
caacgagcag ggcttgtttg 20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:
oligonucleotide; PCR primer 2245-72

<400> SEQUENCE: 18
ggtctgtgta tcgcatcctt tgg 23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
oligonucleotide; PCR primer 1071-80

<400> SEQUENCE: 19
tgcaggtacc ggtccggaat 20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:
oligonucleotide; PCR primer 2279-24

-continued

<400> SEQUENCE: 20
tgtcagagca ggatgcatct gt 22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:
oligonucleotide; PCR primer 2279-22

<400> SEQUENCE: 21
tgcattgcct tgtgccagca ggt 23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:
oligonucleotide; PCR primer 2279-21

<400> SEQUENCE: 22
ctgtcagctg ccagatgagg ttg 23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:
oligonucleotide; PCR primer 2318-34

<400> SEQUENCE: 23
gcgtccctga gtcccagag 19

<210> SEQ ID NO 24
<211> LENGTH: 23
<212> TYPE: DNA
<213> ORGANISM: Artificial Sequence
<220> FEATURE:
<223> OTHER INFORMATION: Description of Artificial
Sequence:oligonucleotide; PCR primer 2318-35

<400> SEQUENCE: 24
gtgtatcgca tcctttggag aag 23

<210> SEQ ID NO 25
<211> LENGTH: 1998
<212> TYPE: DNA
<213> ORGANISM: Homo sapiens
<220> FEATURE:
<221> NAME/KEY: CDS
<222> LOCATION: (152)..(1099)
<220> FEATURE:
<221> NAME/KEY: UNSURE
<222> LOCATION: (233)
<223> OTHER INFORMATION: "Xaa" is Ser or Ala

<400> SEQUENCE: 25

```
cgggccgccc ccggccccca ttcgggccgg gcctcgctgc ggcggcgact gagccaggct     60

gggccgcgtc cctgagtccc agagtcggcg cggcgcggca ggggcagcct tccaccacgg    120

ggagcccagc tgtcagccgc ctcacaggaa g atg ctg cgt cgg cgg ggc agc       172
                                   Met Leu Arg Arg Arg Gly Ser
                                    1               5
```

-continued

```
cct ggc atg ggt gtg cat gtg ggt gca gcc ctg gga gca ctg tgg ttc      220
Pro Gly Met Gly Val His Val Gly Ala Ala Leu Gly Ala Leu Trp Phe
        10                  15                  20

tgc ctc aca gga gcc ctg gag gtc cag gtc cct gaa gac cca gtg gtg      268
Cys Leu Thr Gly Ala Leu Glu Val Gln Val Pro Glu Asp Pro Val Val
    25                  30                  35

gca ctg gtg ggc acc gat gcc acc ctg tgc tgc tcc ttc tcc cct gag      316
Ala Leu Val Gly Thr Asp Ala Thr Leu Cys Cys Ser Phe Ser Pro Glu
 40                  45                  50                  55

cct ggc ttc agc ctg gca cag ctc aac ctc atc tgg cag ctg aca gat      364
Pro Gly Phe Ser Leu Ala Gln Leu Asn Leu Ile Trp Gln Leu Thr Asp
                60                  65                  70

acc aaa cag ctg gtg cac agc ttt gct gag ggc cag gac cag ggc agc      412
Thr Lys Gln Leu Val His Ser Phe Ala Glu Gly Gln Asp Gln Gly Ser
            75                  80                  85

gcc tat gcc aac cgc acg gcc ctc ttc ccg gac ctg ctg gca cag ggc      460
Ala Tyr Ala Asn Arg Thr Ala Leu Phe Pro Asp Leu Leu Ala Gln Gly
        90                  95                  100

aac gca tcc ctg agg ctg cag cgc gtg cgt gtg gcg gac gag ggc agc      508
Asn Ala Ser Leu Arg Leu Gln Arg Val Arg Val Ala Asp Glu Gly Ser
    105                 110                 115

ttc acc tgc ttc gtg agc atc cgg gat ttc ggc agc gct gcc gtc agc      556
Phe Thr Cys Phe Val Ser Ile Arg Asp Phe Gly Ser Ala Ala Val Ser
120                 125                 130                 135

ctg cag gtg gcc gct ccc tac tcg aag ccc agc atg acc ctg gag ccc      604
Leu Gln Val Ala Ala Pro Tyr Ser Lys Pro Ser Met Thr Leu Glu Pro
                140                 145                 150

aac aag gac ctg cgg cca ggg gac acg gtg acc atc acg tgc tcc agc      652
Asn Lys Asp Leu Arg Pro Gly Asp Thr Val Thr Ile Thr Cys Ser Ser
            155                 160                 165

tac cag ggc tac cct gag gct gag gtg ttc tgg cag gat ggg cag ggt      700
Tyr Gln Gly Tyr Pro Glu Ala Glu Val Phe Trp Gln Asp Gly Gln Gly
        170                 175                 180

gtg ccc ctg act ggc aac gtg acc acg tcg cag atg gcc aac gag cag      748
Val Pro Leu Thr Gly Asn Val Thr Thr Ser Gln Met Ala Asn Glu Gln
    185                 190                 195

ggc ttg ttt gat gtg cac agc gtc ctg cgg gtg gtg ctg ggt gcg aat      796
Gly Leu Phe Asp Val His Ser Val Leu Arg Val Val Leu Gly Ala Asn
200                 205                 210                 215

ggc acc tac agc tgc ctg gtg cgc aac ccc gtg ctg cag cag gat gcg      844
Gly Thr Tyr Ser Cys Leu Val Arg Asn Pro Val Leu Gln Gln Asp Ala
                220                 225                 230

cac rgc tct gtc acc atc aca ggg cag cct atg aca ttc ccc cca gag      892
His Xaa Ser Val Thr Ile Thr Gly Gln Pro Met Thr Phe Pro Pro Glu
            235                 240                 245

gcc ctg tgg gtg acc gtg ggg ctg tct gtc tgt ctc att gca ctg ctg      940
Ala Leu Trp Val Thr Val Gly Leu Ser Val Cys Leu Ile Ala Leu Leu
        250                 255                 260

gtg gcc ctg gct ttc gtg tgc tgg aga aag atc aaa cag agc tgt gag      988
Val Ala Leu Ala Phe Val Cys Trp Arg Lys Ile Lys Gln Ser Cys Glu
    265                 270                 275

gag gag aat gca gga gct gag gac cag gat ggg gag gga gaa ggc tcc     1036
Glu Glu Asn Ala Gly Ala Glu Asp Gln Asp Gly Glu Gly Glu Gly Ser
280                 285                 290                 295

aag aca gcc ctg cag cct ctg aaa cac tct gac agc aaa gaa gat gat     1084
Lys Thr Ala Leu Gln Pro Leu Lys His Ser Asp Ser Lys Glu Asp Asp
                300                 305                 310

gga caa gaa ata gcc tgaccatgag gaccagggag ctgctacccc tccctacagc     1139
Gly Gln Glu Ile Ala
```

-continued

```
          315

tcctaccctc tggctgcaat ggggctgcac tgtgagccct gcccccaaca gatgcatcct   1199

gctctgacag gtgggctcct tctccaaagg atgcgataca cagaccactg tgcagcctta   1259

tttctccaat ggacatgatt cccaagtcat cctgctgcct tttttcttat agacacaatg   1319

aacagaccac ccacaacctt agttctctaa gtcatcctgc ctgctgcctt atttcacagt   1379

acatacattt cttagggaca cagtacactg accacatcac caccctcttc ttccagtgct   1439

gcgtggacca tctggctgcc ttttttctcc aaaagatgca atattcagac tgactgaccc   1499

cctgccttat ttcaccaaag acacgatgca tagtcacccc ggccttgttt ctccaatggc   1559

cgtgatacac tagtgatcat gttcagccct gcttccacct gcatagaatc ttttcttctc   1619

agacagggac agtgcggcct caacatctcc tggagtctag aagctgtttc ctttcccctc   1679

cttcctccct gccccaagtg aagacagggc agggccagga atgctttggg gacaccgagg   1739

ggactgcccc ccaccccccac catggtgcta ttctggggct ggggcagtct tttcctggct   1799

tgcctctggc cagctcctgg cctctggtag agtgagactt cagacgttct gatgccttcc   1859

ggatgtcatc tctccctgcc ccaggaatgg aagatgtgag gacttctaat ttaaatgtgg   1919

gactcggagg gattttgtaa actgggggta tattttgggg aaaataaatg tctttgtaaa   1979

aaaaaaaaaa aaaaaaaaa                                                1998


<210> SEQ ID NO 26
<211> LENGTH: 316
<212> TYPE: PRT
<213> ORGANISM: Homo sapiens
<220> FEATURE:
<221> NAME/KEY: UNSURE
<222> LOCATION: (233)
<223> OTHER INFORMATION: “Xaa” is Ser or Ala

<400> SEQUENCE: 26

Met Leu Arg Arg Arg Gly Ser Pro Gly Met Gly Val His Val Gly Ala
  1               5                  10                  15

Ala Leu Gly Ala Leu Trp Phe Cys Leu Thr Gly Ala Leu Glu Val Gln
             20                  25                  30

Val Pro Glu Asp Pro Val Val Ala Leu Val Gly Thr Asp Ala Thr Leu
         35                  40                  45

Cys Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190
```

-continued

```
Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Xaa Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315


<210> SEQ ID NO 27
<211> LENGTH: 951
<212> TYPE: DNA
<213> ORGANISM: Homo sapiens
<220> FEATURE:
<221> NAME/KEY: CDS
<222> LOCATION: (1)..(948)

<400> SEQUENCE: 27

atg ctg cgt cgg cgg ggc agc cct ggc atg ggt gtg cat gtg ggt gca       48
Met Leu Arg Arg Arg Gly Ser Pro Gly Met Gly Val His Val Gly Ala
  1               5                  10                  15

gcc ctg gga gca ctg tgg ttc tgc ctc aca gga gcc ctg gag gtc cag       96
Ala Leu Gly Ala Leu Trp Phe Cys Leu Thr Gly Ala Leu Glu Val Gln
             20                  25                  30

gtc cct gaa gac cca gtg gtg gca ctg gtg ggc acc gat gcc acc ctg      144
Val Pro Glu Asp Pro Val Val Ala Leu Val Gly Thr Asp Ala Thr Leu
         35                  40                  45

tgc tgc tcc ttc tcc cct gag cct ggc ttc agc ctg gca cag ctc aac      192
Cys Cys Ser Phe Ser Pro Glu Pro Gly Phe Ser Leu Ala Gln Leu Asn
     50                  55                  60

ctc atc tgg cag ctg aca gat acc aaa cag ctg gtg cac agc ttt gct      240
Leu Ile Trp Gln Leu Thr Asp Thr Lys Gln Leu Val His Ser Phe Ala
 65                  70                  75                  80

gag ggc cag gac cag ggc agc gcc tat gcc aac cgc acg gcc ctc ttc      288
Glu Gly Gln Asp Gln Gly Ser Ala Tyr Ala Asn Arg Thr Ala Leu Phe
                 85                  90                  95

ccg gac ctg ctg gca cag ggc aac gca tcc ctg agg ctg cag cgc gtg      336
Pro Asp Leu Leu Ala Gln Gly Asn Ala Ser Leu Arg Leu Gln Arg Val
            100                 105                 110

cgt gtg gcg gac gag ggc agc ttc acc tgc ttc gtg agc atc cgg gat      384
Arg Val Ala Asp Glu Gly Ser Phe Thr Cys Phe Val Ser Ile Arg Asp
        115                 120                 125

ttc ggc agc gct gcc gtc agc ctg cag gtg gcc gct ccc tac tcg aag      432
Phe Gly Ser Ala Ala Val Ser Leu Gln Val Ala Ala Pro Tyr Ser Lys
    130                 135                 140

ccc agc atg acc ctg gag ccc aac aag gac ctg cgg cca ggg gac acg      480
Pro Ser Met Thr Leu Glu Pro Asn Lys Asp Leu Arg Pro Gly Asp Thr
145                 150                 155                 160

gtg acc atc acg tgc tcc agc tac cgg ggc tac cct gag gct gag gtg      528
Val Thr Ile Thr Cys Ser Ser Tyr Arg Gly Tyr Pro Glu Ala Glu Val
                165                 170                 175
```

-continued

```
ttc tgg cag gat ggg cag ggt gtg ccc ctg act ggc aac gtg acc acg      576
Phe Trp Gln Asp Gly Gln Gly Val Pro Leu Thr Gly Asn Val Thr Thr
            180                 185                 190

tcg cag atg gcc aac gag cag ggc ttg ttt gat gtg cac agc gtc ctg      624
Ser Gln Met Ala Asn Glu Gln Gly Leu Phe Asp Val His Ser Val Leu
        195                 200                 205

cgg gtg gtg ctg ggt gcg aat ggc acc tac agc tgc ctg gtg cgc aac      672
Arg Val Val Leu Gly Ala Asn Gly Thr Tyr Ser Cys Leu Val Arg Asn
    210                 215                 220

ccc gtg ctg cag cag gat gcg cac ggc tct gtc acc atc aca ggg cag      720
Pro Val Leu Gln Gln Asp Ala His Gly Ser Val Thr Ile Thr Gly Gln
225                 230                 235                 240

cct atg aca ttc ccc cca gag gcc ctg tgg gtg acc gtg ggg ctg tct      768
Pro Met Thr Phe Pro Pro Glu Ala Leu Trp Val Thr Val Gly Leu Ser
                245                 250                 255

gtc tgt ctc att gca ctg ctg gtg gcc ctg gct ttc gtg tgc tgg aga      816
Val Cys Leu Ile Ala Leu Leu Val Ala Leu Ala Phe Val Cys Trp Arg
            260                 265                 270

aag atc aaa cag agc tgt gag gag gag aat gca gga gct gag gac cag      864
Lys Ile Lys Gln Ser Cys Glu Glu Glu Asn Ala Gly Ala Glu Asp Gln
        275                 280                 285

gat ggg gag gga gaa ggc tcc aag aca gcc ctg cag cct ctg aaa cac      912
Asp Gly Glu Gly Glu Gly Ser Lys Thr Ala Leu Gln Pro Leu Lys His
    290                 295                 300

tct gac agc aaa gaa gat gat gga caa gaa ata gcc tga                  951
Ser Asp Ser Lys Glu Asp Asp Gly Gln Glu Ile Ala
305                 310                 315


<210> SEQ ID NO 28
<211> LENGTH: 316
<212> TYPE: PRT
<213> ORGANISM: Homo sapiens

<400> SEQUENCE: 28

Met Leu Arg Arg Arg Gly Ser Pro Gly Met Gly Val His Val Gly Ala
  1               5                  10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
```

-continued

```
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315


<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Myelin
      oligodendrocyte glycoprotein peptide antigen

<400> SEQUENCE: 29

Met Glu Val Gly Trp Tyr Arg Ser Pro Phe Ser Arg Val Val His Lys
  1               5                  10                  15

Tyr Arg Asn Gly Lys
             20


<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: LCMV
      glycoprotein peptide p33

<400> SEQUENCE: 30

Lys Ala Val Tyr Asn Phe Ala Thr Met
  1               5


<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: tetramer
      H-2Db/NP366-374

<400> SEQUENCE: 31

Ala Ser Asn Glu Asn Met Glu Thr Met
  1               5


<210> SEQ ID NO 32
<211> LENGTH: 316
<212> TYPE: PRT
<213> ORGANISM: Artificial Sequence
<220> FEATURE:
<223> OTHER INFORMATION: Description of Artificial Sequence: artificial
      B7RP-2 amino acid sequence
```

-continued

<220> FEATURE:
<221> NAME/KEY: UNSURE
<222> LOCATION: (4)
<223> OTHER INFORMATION: "Xaa" can be any naturally occurring amino acid
<220> FEATURE:
<221> NAME/KEY: UNSURE
<222> LOCATION: (5)
<223> OTHER INFORMATION: "Xaa" can be any naturally occurring amino acid
<220> FEATURE:
<221> NAME/KEY: UNSURE
<222> LOCATION: (7)
<223> OTHER INFORMATION: "Xaa" can be any naturally occurring amino acid
<220> FEATURE:
<221> NAME/KEY: UNSURE
<222> LOCATION: (9)
<223> OTHER INFORMATION: "Xaa" can be any naturally occurring amino acid
<220> FEATURE:
<221> NAME/KEY: UNSURE
<222> LOCATION: (10)
<223> OTHER INFORMATION: "Xaa" can be any naturally occurring amino acid
<220> FEATURE:
<221> NAME/KEY: UNSURE
<222> LOCATION: (13)
<223> OTHER INFORMATION: "Xaa" can be any naturally occurring amino acid
<220> FEATURE:
<221> NAME/KEY: UNSURE
<222> LOCATION: (14)
<223> OTHER INFORMATION: "Xaa" can be any naturally occurring amino acid
<220> FEATURE:
<221> NAME/KEY: UNSURE
<222> LOCATION: (15)
<223> OTHER INFORMATION: "Xaa" can be any naturally occurring amino acid
<220> FEATURE:
<221> NAME/KEY: UNSURE
<222> LOCATION: (16)
<223> OTHER INFORMATION: "Xaa" can be any naturally occurring amino acid
<220> FEATURE:
<221> NAME/KEY: UNSURE
<222> LOCATION: (22)
<223> OTHER INFORMATION: "Xaa" can be any naturally occurring amino acid
<220> FEATURE:
<221> NAME/KEY: UNSURE
<222> LOCATION: (23)
<223> OTHER INFORMATION: "Xaa" can be any naturally occurring amino acid
<220> FEATURE:
<221> NAME/KEY: UNSURE
<222> LOCATION: (34)
<223> OTHER INFORMATION: "Xaa" can be any naturally occurring amino acid
<220> FEATURE:
<221> NAME/KEY: UNSURE
<222> LOCATION: (43)
<223> OTHER INFORMATION: "Xaa" can be any naturally occurring amino acid
<220> FEATURE:
<221> NAME/KEY: UNSURE
<222> LOCATION: (49)
<223> OTHER INFORMATION: "Xaa" can be any naturally occurring amino acid
<220> FEATURE:
<221> NAME/KEY: UNSURE
<222> LOCATION: (80)
<223> OTHER INFORMATION: "Xaa" can be any naturally occurring amino acid
<220> FEATURE:
<221> NAME/KEY: UNSURE
<222> LOCATION: (83)
<223> OTHER INFORMATION: "Xaa" can be any naturally occurring amino acid
<220> FEATURE:
<221> NAME/KEY: UNSURE
<222> LOCATION: (90)
<223> OTHER INFORMATION: "Xaa" can be any naturally occurring amino acid
<220> FEATURE:
<221> NAME/KEY: UNSURE
<222> LOCATION: (115)
<223> OTHER INFORMATION: "Xaa" can be any naturally occurring amino acid
<220> FEATURE:
<221> NAME/KEY: UNSURE
<222> LOCATION: (127)
<223> OTHER INFORMATION: "Xaa" can be any naturally occurring amino acid
<220> FEATURE:
<221> NAME/KEY: UNSURE
<222> LOCATION: (130)

-continued

```
<223> OTHER INFORMATION: "Xaa" can be any naturally occurring amino acid
<220> FEATURE:
<221> NAME/KEY: UNSURE
<222> LOCATION: (159)
<223> OTHER INFORMATION: "Xaa" can be any naturally occurring amino acid
<220> FEATURE:
<221> NAME/KEY: UNSURE
<222> LOCATION: (160)
<223> OTHER INFORMATION: "Xaa" can be any naturally occurring amino acid
<220> FEATURE:
<221> NAME/KEY: UNSURE
<222> LOCATION: (169)
<223> OTHER INFORMATION: "Xaa" can be any naturally occurring amino acid
<220> FEATURE:
<221> NAME/KEY: UNSURE
<222> LOCATION: (179)
<223> OTHER INFORMATION: "Xaa" can be any naturally occurring amino acid
<220> FEATURE:
<221> NAME/KEY: UNSURE
<222> LOCATION: (199)
<223> OTHER INFORMATION: "Xaa" can be any naturally occurring amino acid
<220> FEATURE:
<221> NAME/KEY: UNSURE
<222> LOCATION: (242)
<223> OTHER INFORMATION: "Xaa" can be any naturally occurring amino acid
<220> FEATURE:
<221> NAME/KEY: UNSURE
<222> LOCATION: (300)
<223> OTHER INFORMATION: "Xaa" can be any naturally occurring amino acid
<220> FEATURE:
<221> NAME/KEY: UNSURE
<222> LOCATION: (304)
<223> OTHER INFORMATION: "Xaa" can be any naturally occurring amino acid
<220> FEATURE:
<221> NAME/KEY: UNSURE
<222> LOCATION: (307)
<223> OTHER INFORMATION: "Xaa" can be any naturally occurring amino acid

<400> SEQUENCE: 32

Met Leu Arg Xaa Xaa Gly Xaa Pro Xaa Xaa Gly Val Xaa Xaa Xaa Xaa
  1               5                  10                  15

Ala Leu Gly Ala Leu Xaa Xaa Cys Leu Thr Gly Ala Leu Glu Val Gln
             20                  25                  30

Val Xaa Glu Asp Pro Val Val Ala Leu Val Xaa Thr Asp Ala Thr Leu
         35                  40                  45

Xaa Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Xaa
 65                  70                  75                  80

Glu Gly Xaa Asp Gln Gly Ser Ala Tyr Xaa Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Xaa Asp Glu Gly Ser Phe Thr Cys Phe Val Ser Ile Xaa Asp
        115                 120                 125

Phe Xaa Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Xaa Xaa
145                 150                 155                 160

Val Thr Ile Thr Cys Ser Ser Tyr Xaa Gly Tyr Pro Glu Ala Glu Val
                165                 170                 175

Phe Trp Xaa Asp Gly Gln Gly Val Pro Leu Thr Gly Asn Val Thr Thr
            180                 185                 190

Ser Gln Met Ala Asn Glu Xaa Gly Leu Phe Asp Val His Ser Val Leu
        195                 200                 205
```

-continued

```
Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Xaa Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Xaa Pro Leu Lys Xaa
    290                 295                 300

Ser Asp Xaa Lys Glu Asp Asp Gly Gln Glu Ile Ala
305                 310                 315
```